(12) United States Patent
Concino et al.

(10) Patent No.: US 11,065,307 B2
(45) Date of Patent: *Jul. 20, 2021

(54) THERAPEUTIC FUSION PROTEIN COMPRISING AN ALPHA-N-ACETYLGLUCOSAMINIDASE AND A LYSOSOMAL TARGETING MOIETY

(71) Applicant: Shire Human Genetic Therapies, Inc., Lexington, MA (US)

(72) Inventors: Michael F. Concino, Bolton, MA (US); Pericles Calias, Melrose, MA (US); Jing Pan, Boxborough, MA (US); Kevin Holmes, Belmont, MA (US); Paolo Martini, Boston, MA (US); Alla Romashko, Lexington, MA (US); Muthuraman Meiyappan, Jamaica Plain, MA (US); Bohong Zhang, Newton, MA (US); Andrea Iskenderian, Arlington, MA (US); Dianna Lundberg, Brentwood, NH (US); Angela Norton, Reading, MA (US); Bettina Strack-Logue, Somerville, MA (US); Huang Yan, Billerica, MA (US); Mary Alessandrini, Clinton, MA (US); Richard Pfeifer, North Granby, CT (US)

(73) Assignee: Shire Human Genetic Therapies, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/715,748

(22) Filed: Sep. 26, 2017

(65) Prior Publication Data
US 2018/0085438 A1   Mar. 29, 2018

Related U.S. Application Data

(63) Continuation of application No. 13/892,076, filed on May 10, 2013, now Pat. No. 9,814,764, which is a continuation of application No. 13/168,969, filed on Jun. 25, 2011, now abandoned.

(60) Provisional application No. 61/495,268, filed on Jun. 9, 2011, provisional application No. 61/476,210, filed on Apr. 15, 2011, provisional application No. 61/449,225, filed on Mar. 4, 2011, provisional
(Continued)

(51) Int. Cl.
| A61K 8/66 | (2006.01) |
| C12N 9/24 | (2006.01) |
| A61K 38/47 | (2006.01) |
| A61K 35/76 | (2015.01) |
| A61K 35/761 | (2015.01) |
| A61K 9/19 | (2006.01) |
| A61K 9/00 | (2006.01) |
| A61K 38/46 | (2006.01) |
| C07K 14/65 | (2006.01) |
| C12N 9/42 | (2006.01) |
| A61K 9/08 | (2006.01) |
| A61K 47/02 | (2006.01) |
| A61K 47/26 | (2006.01) |

(52) U.S. Cl.
CPC .......... *A61K 38/47* (2013.01); *A61K 9/0019* (2013.01); *A61K 9/0085* (2013.01); *A61K 9/08* (2013.01); *A61K 9/19* (2013.01); *A61K 35/76* (2013.01); *A61K 35/761* (2013.01); *A61K 38/46* (2013.01); *A61K 38/465* (2013.01); *A61K 47/02* (2013.01); *A61K 47/26* (2013.01); *C07K 14/65* (2013.01); *C12N 9/2402* (2013.01); *C12N 9/2437* (2013.01); *C12Y 301/06008* (2013.01); *C12Y 301/06013* (2013.01); *C12Y 302/0105* (2013.01); *C12Y 302/01045* (2013.01); *C12Y 302/01046* (2013.01); *C12Y 310/01001* (2013.01)

(58) Field of Classification Search
None
See application file for complete search history.

(56) References Cited

U.S. PATENT DOCUMENTS

| 3,133,001 A | 5/1964 | Muset |
| 4,743,265 A | 5/1988 | Whitehouse et al. |
(Continued)

FOREIGN PATENT DOCUMENTS

| JP | 2005-506340 A | 3/2005 |
| JP | 2007-504166 A | 3/2007 |
(Continued)

OTHER PUBLICATIONS

Altschul et al., Basic logic alignment search tool, J. Mol. Biol., 215(3): 403-410, 1990.
(Continued)

*Primary Examiner* — David Steadman
(74) *Attorney, Agent, or Firm* — Proskauer Rose LLP; Fangli Chen

(57) ABSTRACT

Among other things, the present invention provides methods and compositions of treating Sanfilippo syndrome type B (Sanfilippo B) by, e.g., intrathecal (IT) administration of a Naglu protein. A suitable Naglu protein can be a recombinant, gene-activated or natural protein. In some embodiments, a suitable Naglu protein is a recombinant Naglu protein. In some embodiments, a recombinant Naglu protein is a fusion protein containing a Naglu domain and a lysosomal targeting moiety. In some embodiments, the lysosomal targeting domain is an IGF-II moiety.

8 Claims, 38 Drawing Sheets

Specification includes a Sequence Listing.

Related U.S. Application Data application No. 61/442,115, filed on Feb. 11, 2011, provisional application No. 61/435,710, filed on Jan. 24, 2011, provisional application No. 61/387,862, filed on Sep. 29, 2010, provisional application No. 61/360,786, filed on Jul. 1, 2010, provisional application No. 61/358,857, filed on Jun. 25, 2010.

(56) References Cited

U.S. PATENT DOCUMENTS

| | | | |
|---|---|---|---|
| 5,972,333 | A | 10/1999 | Hopwood et al. |
| 6,118,045 | A | 9/2000 | Reuser et al. |
| 6,217,552 | B1 | 4/2001 | Barbut et al. |
| 6,255,096 | B1 | 7/2001 | Hopwood et al. |
| 6,534,300 | B1 | 3/2003 | Canfield |
| 6,537,785 | B1 | 3/2003 | Canfield |
| 7,351,410 | B2 | 4/2008 | van Bree et al. |
| 7,396,811 | B2 | 7/2008 | LeBowitz et al. |
| 7,442,372 | B2 | 10/2008 | Kakkis |
| 7,560,424 | B2 | 7/2009 | LeBowitz et al. |
| 7,629,309 | B2 | 12/2009 | LeBowitz et al. |
| 8,545,837 | B2 | 10/2013 | Zhu et al. |
| 8,580,922 | B2 * | 11/2013 | Martini .................. A61K 38/30 530/326 |
| 9,206,235 | B2 * | 12/2015 | Martini .................. A61K 38/30 |
| 9,283,181 | B2 | 3/2016 | Calias et al. |
| 9,814,764 | B2 * | 11/2017 | Concino .............. A61K 9/0085 |
| 9,932,568 | B2 * | 4/2018 | Martini ................ A61K 38/465 |
| 2002/0052311 | A1 | 5/2002 | Solomon et al. |
| 2002/0099025 | A1 | 7/2002 | Heywood |
| 2003/0072761 | A1 | 4/2003 | LeBowitz |
| 2003/0082176 | A1 | 5/2003 | LeBowitz et al. |
| 2004/0005309 | A1 | 1/2004 | LeBowitz et al. |
| 2004/0006008 | A1 | 1/2004 | LeBowitz et al. |
| 2004/0172665 | A1 | 9/2004 | Reuser et al. |
| 2004/0243058 | A1 | 12/2004 | Barbut et al. |
| 2004/0248262 | A1 | 12/2004 | Koeberl et al. |
| 2005/0042227 | A1 | 2/2005 | Zankel et al. |
| 2005/0048047 | A1 | 3/2005 | Kakkis |
| 2005/0208090 | A1 | 9/2005 | Keimel et al. |
| 2005/0244400 | A1 | 11/2005 | LeBowitz et al. |
| 2005/0281805 | A1 | 12/2005 | LeBowitz et al. |
| 2006/0029656 | A1 | 2/2006 | O'Donnell et al. |
| 2006/0153829 | A1 | 7/2006 | Fan |
| 2006/0177433 | A1 | 8/2006 | Treco et al. |
| 2008/0003211 | A1 | 1/2008 | Fogh et al. |
| 2008/0299640 | A1 | 12/2008 | LeBowitz et al. |
| 2009/0017005 | A1 | 1/2009 | Kakkis |
| 2009/0041741 | A1 | 2/2009 | Sly et al. |
| 2009/0130079 | A1 | 5/2009 | Dodge et al. |
| 2009/0191178 | A1 | 7/2009 | Zankel et al. |
| 2009/0192087 | A1 * | 7/2009 | Glass .................... C07K 14/50 514/9.3 |
| 2009/0226948 | A1 | 9/2009 | Reichert |
| 2009/0246187 | A1 | 10/2009 | Nilsson |
| 2009/0291062 | A1 | 11/2009 | Fraunhofer et al. |
| 2009/0297592 | A1 | 12/2009 | Sakuraba et al. |
| 2010/0068195 | A1 | 3/2010 | Vellard et al. |
| 2010/0249021 | A1 * | 9/2010 | Gao ..................... A61K 38/162 514/3.7 |
| 2010/0260706 | A1 | 10/2010 | Bogin et al. |
| 2011/0105560 | A1 | 5/2011 | Wustman |
| 2011/0318323 | A1 | 12/2011 | Zhu et al. |
| 2011/0318324 | A1 | 12/2011 | Salamat-Miller et al. |
| 2011/0318327 | A1 | 12/2011 | Concino et al. |
| 2012/0003202 | A1 | 1/2012 | Calias et al. |
| 2012/0009171 | A1 | 1/2012 | Salamat-Miller et al. |
| 2012/0014936 | A1 | 1/2012 | Natoli et al. |
| 2012/0148558 | A1 | 6/2012 | Kakkis |
| 2012/0213762 | A1 | 8/2012 | LeBowitz et al. |
| 2013/0168961 | A1 | 7/2013 | Stahlkopf et al. |
| 2013/0295071 | A1 | 11/2013 | Salamat-Miller et al. |
| 2013/0295077 | A1 | 11/2013 | Concino et al. |
| 2014/0271598 | A1 | 9/2014 | Zhu et al. |

FOREIGN PATENT DOCUMENTS

| | | | |
|---|---|---|---|
| JP | 2007-519404 A | 7/2007 | |
| JP | 2011-521627 A | 7/2011 | |
| RU | 2209080 C2 | 7/2003 | |
| WO | WO-94/17819 | 8/1994 | |
| WO | WO-2002/087510 A2 | 11/2002 | |
| WO | WO-2003/032727 A1 | 4/2003 | |
| WO | WO-2003/032913 A2 | 4/2003 | |
| WO | WO-2003/102583 A1 | 12/2003 | |
| WO | WO-2005/002515 A2 | 1/2005 | |
| WO | WO-2005/021064 A2 | 3/2005 | |
| WO | WO-2005/078077 A2 | 8/2005 | |
| WO | WO-2007/141346 A2 | 12/2007 | |
| WO | WO-2008/070769 A1 | 6/2008 | |
| WO | WO-2009/017005 A1 | 2/2009 | |
| WO | WO-2009062348 A1 * | 5/2009 | ........... A61K 38/162 |
| WO | WO-2009/073569 A2 | 6/2009 | |
| WO | WO-2009/131698 A2 | 10/2009 | |
| WO | WO-2009/137721 A2 | 11/2009 | |
| WO | WO-2011/163647 A2 | 12/2011 | |
| WO | WO-2011/163648 A1 | 12/2011 | |
| WO | WO-2011/163649 A2 | 12/2011 | |
| WO | WO-2011/163650 A2 | 12/2011 | |
| WO | WO-2011/163651 A2 | 12/2011 | |
| WO | WO-2011/163652 A2 | 12/2011 | |
| WO | WO-2012/023623 A2 | 2/2012 | |

OTHER PUBLICATIONS

Altschul et al., Gapped BLAST and PSI-BLAST: a new generation of protein database search programs, Nucleic Acids Res. 25: 3389-3402, 1997.

Altschul et al., Local alignment statistics, 266:460-80, Methods in Enzymology., 1996.

Ammaya et al., Subcutaneous Reservoir and Pump for Sterile Access to Ventricular Cerebrospinal Fluid, Lancet 2(7315): 983-984, 1963.

Anonymous, TKT to Present Research on Intrathecal Delivery of I2S for Hunter Syndrome at ASHG, PRNewswire, 1 (2004).

Anonymous, TKT's Research Findings on Intrathecal Delivery of I2S Presented at ASHG, Evaluate Ltd, 1 (2004).

Baskin, G. et al., Genetic galactocerebrosidase deficiency (globoid cell leukodystrophy, Krabbe disease) in rhesus monkeys (*Macaca mulatta*), Lab Anim. Sci., 48(5): 476-482, 1998.

Baum, H. et al., The assay of arylsulphatases A and B in human urine, Clin Chim Acta. 4(3): 453-455, 1959.

Begley et al., Lysosomal storage diseases and the blood-brain barrier, Curr Pharm Des 14(16): 1566-1580, 2008.

Belichenko et al., Penetration, diffusion, and uptake of recombinant human alpha-L-iduronidase after intraventricular injection into the rat brain, Mol. Genet. Metab., 86(1-2): 141-149, 2005.

Beniaminovitz et al., Prevention of rejection in cardiac transplantation by blockage of the interleukin-2 receptor with a monoclonal antibody, N. Engl. J. Med. 342(9): 613-619, 2000.

Berard et al., A review of interleukin-2 receptor antagonists in solid organ transplantation, Pharmacotherapy 19(10): 1127-1137, 1999.

Bielicki et al., Recombinant human sulphamidase: expression, amplification, purification and characterization, Journal of Biochemistry, 329(Pt 1): 145-150, 1998.

Biswas, S. et al., Substrate reduction intervention by L-cycloserine in twitcher mice (globoid cell leukodystrophy) on a B6; CAST/Ei background, Neurosci. Lett., 347(1): 33-36, 2003.

Blasberg, R.G. et al., Intrathecal chemotherapy: brain tissue profiles after ventriculocisternal perfusion, J Pharmacol Exp Ther. 195(1): 73-83, 1975.

Bobo et al., Convection-enhanced delivery of macromolecules in the brain, Proc. Natl. Acad. Sci. U.S.A. 91(6), 2076-2080, 1994.

Bowman, R.H., Inhibition of citrate metabolism by sodium fluoroacetate in the perfused rat heart and the effect on phosphofructokinase activity and glucose utilization, 93(2): 13C-15C, 1964.

Branco et al., Selective deletion of antigen-specific, activated T cells by a humanized MAB to CD2 (MEDI-507) is mediated by NK cells, Transplantation 68(10): 1588-1596, 1999.

(56) References Cited

OTHER PUBLICATIONS

Butt, M.T., Morphologic changes associated with intrathecal catheters for direct delivery to the central nervous system im preclinical studies, Toxicol. Pathol., 39(1): 213-219, 2011.

Cabrera-Salazar, M.A. et al., Intracerebroventricular delivery of glucocerebrosidase reduces substrates and increases lifespan in a mouse model of neuronopathic Gaucher disease, Exp Neurol. 225(2): 436-444, 2010.

Champion K. J. et al., Identification and characterization of a novel homozygous deletion in the x-N-acetylglucosaminidase gene in a patient with Sanfilippo type B syndrome (mucopolysaccharidosis IIIB), Molecular Genetics and Metabolism, 100: 51-56 (2010).

Chirmule et al., Readministration of adenovirus vector in nonhuman primate lungs by blockage of CD4O-CD40 ligand interactions, J. Virol. 74(7): 3345-3352, 2000.

Chiro et al., Spinal descent of cerebrospinal fluid in man, Neurology 26(1): 1-8, 1976.

Clarke, L. A., Idursulfase for the treatment of mucopolysaccharidosis II, Expert Opin. Pharmacother., 9(2):311-317 (2008).

Cressent, A. et al., Improved Behavior and Neuropathology in the Mouse Model of Sanfilippo Type IIIB Disease after Adeno-Associated Virus-Mediated Gene Transfer in the Striatum, The Journal of Neuroscience, 24(45): 10229-10239 (2004).

Dekaban, A.S., Changes in brain weights during the span of human life: relation of brain weights to body heights and body weights, Ann Neurol 4: 345-356, 1978.

Descartes, M. et al., Enzyme Replacement Therapy for MPS II: Developing a Pre-Medication Protocol, University of Alabama and Children's Hospital of Alabama, 1 (2007).

Desnick, R.J., Enzyme replacement and enhancement therapies for lysosomal diseases, J. Inherit. Metab. Dis., 27(3): 385-410, 2004.

Dickson, P.I., Novel Treatments and Future Perspectives: Outcomes of Intrathecal Drug Delivery, International Journal of Clinical Pharmacology and Therapeutics, 47:1 S124-127 (2009).

Eckhoff et al., The safety and efficacy of a two-dose daclizumab (zenapax) induction therapy in liver transplant recipients, Transplantation 69(9): 1867-1872, 2000.

Ekberg et al., Daclizumab prevents acute rejection and improves patient survival post transplantation: 1 year pooled analysis, Transpl. Int. 13(2): 151-159, 2000.

Elaprase (idursulfase), REV 5, 2011.

Elaprase idursulface, European Medicines Agency—Science, Medicines, Health, XP-002716697, pp. 1-3 (2007).

Esposito, S. et al, Heparan N-sulfatase gene: two novel mutations and transient expression of 15 defects, Biochimica et Biophysica Acta 1501, 1-11: 1 (2000).

European Search Report for EP, 11799034.1, 8 pages (dated Mar. 12, 2014).

Extended European Search Report for EP11799035.8, 7 pages, dated Dec. 16, 2013.

Extended European Search Report for 11799039.0, 12 pages (dated Jun. 10, 2014).

Felice, B.R. et al., Safety Evaluation of Chronic Intrathecal Administration of Idursulfase-IT in Cynomolgus Monkeys, Toxicology Pathology, 39:879-892 (2011).

Fenstermacher et al., Drug diffusion within the brain, Ann NY Acad Sci 531: 29-39, 1988.

Ficko-Blean, E. et al., Structural and mechanistic insight into the basis of mucopolysaccharidosis IIIB, PNAS, 105(18): 6560-6565, 2008.

Fishwild et al., Differential effects of administration of a human anti-CD4 monoclonal antibody, HM6G, in nonhuman primates, Clin. Immunol. 92(2): 138-152, 1999.

Fu, H. et al., Restoration of Central Nervous System a-N-Acetylglucosaminidase Activity and Therapeutic Benefits in Mucopolysaccharidosis IIIB Mice by a Single Intracisternal Recombinant Adeno—Associated Viral Type 2 Vector Delivery, The Journal of Gene Medicine, 12:624-633 (2010).

Fu, H. et al., Significantly Increased Lifespan and Improved Behavioral Performances by rAAV Gene Delivery in Adult Mucopolysaccharidosis IIIB Mice, Gene Therapy 14:1065-1077 (2007).

Garbuzova-Davis, S. et al., Transplantation of Human Umbilical Cord Blood Cells Benefits an Animal Model of Sanfilippo Syndrome Type B, Stem Cells and Development, 14:384-394 (2005).

Garcia, A.R. et al., Intrathecal Delivery of Iduronate 2-Sulfatase to the CNS of Cynomolgous Monkeys, Shire Human Genetic Therapies, 1 (2007).

Gaziev et al., Chronic graft-versus-host disease: is there an alternative to the conventional treatment?, Bone Marrow Transplant, 25(7): 689-696, 2000.

GenBank accession No. NM000263, *Homo Sapiens* N-Acetylglucosaminidase, Alpha (NAGLU) mRNA, 1-4 (accessed May 3, 2014).

GeneCards, Galactosylceramidase, 2012.

Ghersi-Egea, J.F. et al, Rapid distribution of intraventricularly administered sucrose into cerebrospinal fluid cisterns via subarachnoid velae in rat, Neuroscience 75(4): 1271-1288, 1996.

Graham et al., Characteristics of a human cell line transformed by DNA from human adenovirus type 5, J. Gen Virol., 36(1): 59-74, 1977.

Greene, et al., Metachromatic Leukodystrophy Treatment with Arylsulfatase-A, Arch Neurol, vol. 20, pp. 147-153, Feb. 1969.

Grubb, J.H. et al., New strategies for enzyme replacement therapy for lysosomal storage diseases, Rejuvenation Research 13(2-3): 229-236, 2010.

Gummert et al., Newer immunosuppressive drugs: a review, J. Am. Soc. Nephrol, 10(6): 1366-1380, 1999.

Hashimoto, R., N-terminal deletion mutants of insulin-like growth factor-II (IGF-II) show Thr7 and Leu8 important for binding to insulin and IGF-I receptors and Leu8 critical for all IGF-II functions, J Biol Chem., 270(30); 18013-18018, 1995.

Hemsley, Kim M. et al., Injection of recombinant human sulfamidase into the CSF via the cerebellomedullary cistern in MPS IIIA mice, Mol Genet Metab. 90(3): 313-328, 2007.

Hemsley, et al., Effect of High Dose, Repeated Intra-Cerebrospinal Fluid Injection of Sulphamidase on Neuropathology in Mucopolysaccharidosis Type IIIA Mice, Genes, Brain and Behavior (2008) 7:740-753.

Henry, M.L., Cyclosporine and tacrolimus (FK506): a comparison of efficacy and safety profiles, Clin. Transplant, 13(3): 209-220, 1999.

Hong et al., Immunosuppressive agents in organ transplantation: past, present, and future, Semin. Nephrol. 20(2): 108-125, 2000.

Hood, R.D., Development and Reproductive Toxicology: A practical approach, 276, 2006.

Hoogerbrugge, P.M., et al., Effect of bone marrow transplantation on enzyme levels and clinical course in the neurologically affected, J. Clin. Invest., 81(6): 1790-1794, 1988.

Hovland, D.N. et al., Six-month continuous intraputamenal infusion toxicity study of recombinant methionyl human glial cell line-derived neurotrophic factor (r-metHuGDNF in rhesus monkeys, Toxicol. Pathol., 35(7): 1013-1029, 2007.

Ideguchi et al., Local adenovirus-mediated CFLA40immunoglobulin expression suppresses the immune responses to adenovirus vectors in the brain, Neuroscience 95(1): 217-226, 2000.

International Preliminary Report on Patentability for PCT/US11/41928, 36 pages (dated Mar. 29, 2013).

International Search Report for PCT/US11/41922, dated Feb. 14, 2012.

International Search Report for PCT/US11/41924, dated Nov. 7, 2011.

International Search Report for PCT/US11/41925, dated Feb. 14, 2012.

International Search Report for PCT/US11/41926, 5 pages (dated May 13, 2013).

International Search Report for PCT/US11/41927, dated Mar. 9, 2012.

International Search Report for PCT/US2011/041928,4 pages (dated Sep. 26, 2012).

(56) References Cited

OTHER PUBLICATIONS

Ito et al., Induction of CTL responses by simultaneous administration of liposomal peptide vaccine with anti-CD40 and anti-CTLA-4 mAb, J. Immunol. 164(3): 1230-1235, 2000.
Johanson, C.E. et al., Multiplicity of cerebrospinal fluid functions: New challenges in health and disease, Cerebrospinal Fluid Res., 14(5): 10, 2008.
Johnson, K., Globoid leukodystrophy in the cat, J. Am. Vet. Med. Assoc., 157(12): 2057-2064, 1970.
Joshi, S. et al., Targeting the brain: rationalizing the novel methods of drug delivery to the central nervous system, Neurocrit Care 6(3): 200-212, 2007.
Kakkis, E. et al., Intrathecal enzyme replacement therapy reduces lysosomal storage in the brain and meninges of the canine model of MPS I, Molecular Genetics and Metabolism 83:163-174 (2004).
Kang, H. et al., Significantly increased lifespan and improved behavioral performances by rAAV gene delivery in adult mucopolysaccharidosis IIIB mice, Gene Therapy, 14:1066-1077 (2007).
Kerwin, J. Pharm. Sci., 97: 2924-2935 (2008).
Kobayashi, T. et al., The Twitcher mouse: an enzymatically authentic model of human globoid cell leukodystrophy (Krabbe disease), Brain Res., 202(2): 479-483, 1980.
Krewson, C.E. et al., Distribution of nerve growth factor following direct delivery to brain interstitium, Brain Res. 680(1-2): 196-206, 1995.
Kurlberg et al., Blockage of the B7-CD28 pathway by CTLA4-Ig counteracts rejection and prolongs survival in small bowel transplantation, Scand. J. Immunol, 51(3): 224-230, 2000.
Lamsa, J.C et al., Delivery of I2S to the Canine CNS: Comparison of Intracisternal, Intralumbar and Intraventricular Dose Routes as Potential Treatents for Severe MPS II, Shire HGT, 1 (2006).
Lamsa, J.C. et al., Intrathecal Delivery of Iduronate 2-Sulfatase for MPS II to the Canine CNS, ASHG Annual Meeting, 1 (2004).
Lazorthes et al., Advances in Drug Delivery Systems and Application in Neurosurgery, 18: 143-192, 1991.
Lee et al., Single-dose intracerebroventricular administration of galactocerebrosidase improves survival in a mouse model of globoid cell leukodystrophy, FASEB Journal, 21(10): 2520-2527, 2007.
Levine, S. et al., L-cycloserine slows the clinical and pathological course in mice with globoid cell leukodystrophy (twitcher mice), J. Neurosci. Res., 60(2): 231-236, 2000.
Li et al., Attenuated plasticity in neurons and astrocytes in the mouse model of Sanfilippo syndrome type B, J Neurosci Res, 69(1): 30-8, 2002.
Li, H.H. et al., Mouse model of Sanfilippo syndrome type B produced by targeted disruption of the gene encoding alpha-N-acetylglucosaminidase, PNAS 96(25): 14505-14510, 1999.
Lin, D., et al., Central nervous system-directed AAV2/5-mediated gene therapy synergizes with bone marrow transplantation in the murine model of globoid-cell leukodystrophy, Mol. Ther., 15(1): 44-52, 2007.
Lu, Y. et al., Direct Brain Delivery of Iduronate 2-Sulfastase Reduces Glycosaminoglycan Accumulation and Improves Histopathology in the CNS and Peripheral Tissue of Hunter Mice, Shire HGT, 1 (2007).
Luca, Tonia, Axons mediate the distribution of arylsulfatase A within the mouse hippocampus upon gene delivery, Mol Ther. 12(4): 669-679, 2005.
Marinova-Mutafchieva et al., A comparative study into the mechanisms of action of anti-tumor necrosis factor alpha, anti-CD4, and combined anti-tumor necrosis factor alpha/anti-CD4 treatment in early collagen-induced arthritis, Arthritis Rheum 43: 638-644, 2000.
Mather et al., Culture of testicular cells in hormone-supplemented serum-free medium, Ann N.Y. Acad. Sci., 383: 44-68, 1982.
Mather, Establishment and characterization of two distinct mouse testicular epithelial cell lines, Biol. Reprod., 23: 243-251, 1980.
Matheus, M.G. et al., Brain MRI findings in patients with mucopolysaccharidosis types I and II and mild clinical presentation, Neuroradiology 46(8): 666-672, 2004.

Matzner, U. et al., Enzyme replacement improves nervous system pathology and function in a mouse model for metachromatic leukodystrophy, Human Molecular Genetics, 14(9):1139-1152 (2005).
Meikle et al., Diagnosis of lysosomal storage disorders: evaluation of lysosome-associated membrane protein LAMP-1 as a diagnostic marker, Clin Chem., 43(8 Pt 1): 1325-1335, 1997.
Middaugh et al., Determination of the apparent thermodynamic activities of saturated protein solutions, J. Biol. Chem. 254(2): 367-370, 1979.
Moder, K.G., New medications for use in patients with rheumatoid arthritis, Ann. Allergy Asthma Immunol. 84(3): 280-284, 2000.
Nagaraja, T.N. et al., In normal rat, intraventricularly administered insulin-like growth factor-1 is rapidly cleared from CSF with limited distribution into brain, Cerebrospinal Fluid Res. 2: 1-15, 2005.
Nail, S.L. et al., Fundamentals of freeze-drying, in Development and manufacture of protein pharmaceuticals, Nail S.L. editor New York: Kluwer Academic/Plenum Publishers, 281-353, 2002.
Neufeld, E.F., Enzyme Replacement therapy. Lysosomal disorders of the Brain, ed. F.M.A.W. Platt, S.V. 2004: Oxford University Press: 327-338, 2004.
Neufeld, E.F., Muenzer J., The mucopolysaccharidoses, In: Scriver CR, Beaudet Al, Sly WS, et al, eds. The Metabolic and Molecular Bases of Inherited Disease. www.ommbid.com 8th ed. New York, NY: McGraw-Hill; 2001:3421-3452.
Nevins, T.E., Overview of new immunosuppressive therapies, Curr. Opin. Pediatr. 12(2): 146-150, 2000.
Nguyen et al., Convective distribution of macromolecules in the primate brain demonstrated using computerized tomography and magnetic resonance imaging, J. Neurosurg. 98(3), 584-590, 2003.
Ohmi et al., Activated microglia in cortex of mouse models of mucopolysaccharidoses I and IIIB, Proc Natl Acad Sci, 100(4): 1902-7, 2002.
Okuyama, T. et al., Japan Elaprase® Treatment (JET) study: Idursulfase enzyme replacement therapy in adult patients with attenuated Hunter syndrome (Mucopolysaccharidosis II, MPS II), Molecular Genetics and Metabolism, 99:18-25 (2010).
Ommaya et al., Implantable devices for chronic access and drug delivery to the central nervous system, Cancer Drug Delivery, 1(2): 169-179, 1984.
Pardridge, W.M., Drug transport in brain via the cerebrospinal fluid, Fluids Barriers CNS, 8(1): 7, 2011.
Passini, M.A. et al., Distribution of a lysosomal enzyme in the adult brain by axonal transport and by cells of the rostral migratory stream, J Neurosci 22(15): 6437-6446, 2002.
Penn, R.D. et al., Intrathecal ciliary neurotrophic factor delivery for treatment of amyotrophic lateral sclerosis (phase I trial), Neurosurgery 40(1): 94-99, 1997.
Phosphate Buffer Calculation, Dec. 31, 2000, accessed Aug. 28, 2012.
Ponce, R.P., et al., Immunogenicity of biologically-derived therapeutics: assessment and interpretation of nonclinical safety studies, Regul. Toxicol. Pharmacol., 54(2): 164-182, 2009.
Ponticelli et al., Promising new agents in the prevention of transplant rejection, Drugs R.D. 1(1), 55-60, 1999.
Potter et al., Review—the use of immunosuppressive agents to prevent neutralizing antibodies against a transgene product, Ann. N.Y. Acad. Sci. 875: 159-174, 1999.
Pritchard, D. et al., Globoid cell leucodystrophy in polled Dorset sheet, Vet. Pathol., 17(4): 399-405, 1980.
Przepiorka et al., A phase II study of BTI-322, a monoclonal anti-CD2 antibody, for treatment of steroid-resistant acute graft-versus-host disease, Blood 92(11): 4066-4071, 1998.
Qi et al., Effect of tacrolimus (FK506) and sirolimus (rapamycin) mono- and combination therapy in prolongation of renal allograft survival in the monkey, Transplantation 69(7), 1275-1283, 2000.
Rangel-Yagui, Carlota O., Micellar solubilization of ibuprofen—influence of surfactant head groups on the extent of solubilization, Brazilian Journal of Pharmaceutical Sciences, 2005, vol. 41, No. 2, pp. 237-246.
Rieselbach, R.E. et al., Subarachnoid distribution of drugs after lumbar injection, N Engl J Med. 267(25): 1273-1278, 1962.

(56) References Cited

OTHER PUBLICATIONS

Savas et al., Intracerebral injection of sulfamidase delays neuropathology in murine MPS-IIIA, Mol Genet Metab., 82(4): 273-285, 2004.
Schlessingerman, A., Mass of an Adult, obtained from hypertextbook.com/facts/2003/AlexSchlessingerman.shtml, 2003, 2 pages.
Schramm, L. L, Surfactants: fundamental and application in the petroleum industry, Cambridge University Press, 2000, p. 5.
Scientific Discussion—Elaprase, XP00271916, pp. 1-43 (2007).
Shahrokh et al., Intrathecal delivery of protein therapeutics to treat genetic diseases involving the CNS, in: Injectable Drug Delivery 2010: Formulations Focus, ONdrugDelivery, pp. 16-20, 2010.
Shire Human Genetic Therapies, Intrathecal Delivery of Protein Therapeutics to Treat Genetic Diseases Involving the CNS, www.ondrugdelivery.com, pp. 16-20, (Publically available on Jun. 30, 2010).
Simard, J.M. et al., Brain oedema in focal ischaemia: molecular pathophysiology and theoretical implications, Lancet Neurol. 6(3): 258-268, 2007.
Sinow, C.S., Construction of an IGF-NAGLU Fusion Protein for Treatment of Sanfilippo B Syndrome, California State Sciene Fair, 1 (2008).
Sjoberg, M. et al., Long-term Intrathecal Morphine and Bupivacaine in Patients with Refractory Cancer Pain, Anesthesiology, 80:284-297 (1994).
Slavik et al., CD28/CTLA-4 and CD80/CD86 families: signaling and function, Immunol Res. 19(1): 1-24, 1999.
Stamatovic S.M., et al., Brain endothelial cell-cell junctions: how to open the blood brain barrier, Curr. Neuropharmacol., 6(3): 179-192, 2008.
Stroobants S. et al., Intracerebroventricular enzyme infusion corrects central nervous system pathology and dysfunction in a mouse model of metachromatic leukodystrophy, Hum Mol Genet. 20(14): 2760-2769, 2011.
Sturk et al., Combined Intracerebroventricular Intraperitoneal Enzyme Replacement Therapy Improves Survival and Reduces Brain Psychosine in a Mouse Model of Krabbe Disease, European Task Force on Brain and Neurogenerative Lysosomal Storage Diseases, http://www.brains4brain.eu/assets/files/abstract-francoforte-2009.pdf p. 42, 2009.
Tang, X. et al., Design of freeze-drying processes for pharmaceuticals: Practical advice, Pharm. Res., 21(2): 191-200, 2004.
Tippin, B. et al., Insulin-like Growth Factor-2 Peptide Fusion Enables Uptake and Lysosomal Delivery of N-Acetylglucosamindidase to Mucopolysaccharidosis IIIB Fibrboblasts, MPS Scientific Program: Plenary Papers, entire document: p. 100 (Jun. 26, 2010).
Toyoshima, E. et al., Nerve conduction studies in the Twitcher mouse (murine globoid cell leukodystrophy), J. Neurol. Sci., 74(2-3): 307-318, 1986.
Urlaub and Chasin, Isolation of Chinese hamster cell mutants deficient in dihydrofolate reductase activity, Proc. Natl. Acad. Sci. USA, 77(7): 4216-4220, 1980.
Vedolin, L. et al., Correlation of MR imaging and MR spectroscopy findings with cognitive impairment in mucopolysaccharidosis II, AJNR Am J Neuroradial 28(6): 1029-1033, 2007.
Vertemati, T. et al., Multidisciplinary Evaluation in 12 Mucopolysaccharidose Type II or Hunter Syndrome Patients Prior Enzyme Replacement Therapy, CREIM, UNIFESP, 1 (2007).
Vite, Charles H. et al., Biodistribution and pharmacodynamics of recombinant human alpha-L-iduronidase (rhIDU) in mucopolysaccharidosis type I-affected cats following multiple intrathecal administrations, Mol Genet Metab 103(3): 268-274, 2011.
Vogler, C. et al., Overcoming the blood-brain barrier with high-dose enzyme replacement therapy in murine mucopolysaccharidosis VII, Proc Natl Acad Sci USA 102(41): 14777-14782, 2005.
Waheed, A. et al., Purification of mammalian arylsulfatase A enzymes by subunit affinity chromatography, Int J Pept Protein Res., 26(4): 362-372, 1985.
Walkley, Cell Pathology of lysosomal storage disorders, Brain Pathol., 8, 175-93, 1998.
Wang et al., Lyophilization and development of solid protein pharmaceuticals, Int. J. Pharm., 203(1-2): 1-60, 2000.
Wang et al., Treatment reduces or stabilizes brain imaging abnormalities in patients with MPS I and II, Molecular Genetics and Metabolism, 98(4): 406-11, 2009.
Wang, W. and Roberts, C., Aggregation of Therapeutic Proteins, published by John Wiley & Sons, Inc., Hoboken, New Jersey (2010).
Watson et al., Intrathecal administration of AAV vectors for the treatment of lysosomal storage in the brains of MPS I mice, Gene Ther., 13(11): 917-925, 2006.
Weber, B. et al., Novel Mutations in Sanfilippo A syndrome: Implications for Enzyme function, Hum. Mol. Genet., 6(9): 1573-1579 (1997).
Wenger, D.A. et al., Galactosylceramide Lipidosis: Globoid Cell Leukodystrophy (Krabbe Disease), in the Metabolic and Molecular Bases of Inherited Disease, C.R. Scriver, Beaudet, A., Sly, W.S. and Valle, D. Editor 2001 McGraw-Hill, 3669-3687, 2001.
Wenger, D.A., Murine, canine and non-human primate models of Krabbe disease, Mol. Med. Today, 6(11): 449-451, 2000.
Williams N.A. et al., The lyophilization of pharmaceuticals; A literature review. J. Parenter Sci. Technol., 38(2): 48-59, 1984.
Wiseman et al., Daclizumab: a review of its use in the prevention of acute rejection in renal transplant recipients, Drugs 58(6): 1029-1042, 1999.
Won, C., Stabilizers against heat-induced aggregation of RPR 114849, an acidic fibroblast growth factor (aFGF), International Journal of Pharmaceutics, 167:25-36 (1998).
Wraith, J.E. et al., Mucopolysaccharidosis type II (Hunter syndrome): a clinical review and recommendations for treatment in the era of enzyme replacement therapy, Eur. J. Pediatr., 167: 247-277 (2008).
Written Opinion for PCT/US11/41922, dated Feb. 14, 2012.
Written Opinion for PCT/US11/41924, dated Nov. 7, 2011.
Written Opinion for PCT/US11/41925, dated Feb. 14, 2012.
Written Opinion for PCT/US11/41926, 8 pages (dated May 13, 2013).
Written Opinion for PCT/US11/41927, dated Mar. 9, 2012.
Written Opinion for PCT/US2011/041928,13 pages (dated Sep. 26, 2012).
Yan, Q. et al., Distribution of intracerebral ventricularly administered neurotrophins in rat brain and its correlation with trk receptor expression, Exp Neurol. 127(1): 23-36, 1994.
Yeager, A. et al., Prolonged survival and remyelination after hematopoietic cell transplantation in the twitcher mouse, Science, 225(4666): 1052-1054, 1984.
Dickson, P. et al, Intrathecal enzyme replacement therapy: Successful treatment of brain disease via the cerebrospinal fluid, Molecular Genetics & Metabolism, 91(1):61-68(2007).
Kroin JS, "Intrathecal Drug Administration Present Use and Future Trends," Clin Pharmacokinet, 22(5):319-326 (1992).

* cited by examiner

| Protein Name | Structure | no. of aa / theori mw | POC outcome |
|---|---|---|---|
| PerT-Naglu | NAGLU | 720 / 80.2 kDa | failed (BBB) |
| Naglu-ApoE | NAGLU — Myc tag — LINKER — ApoE | 769 / 86.0 kDa | In progress (BBB) |

*Fig. 2*

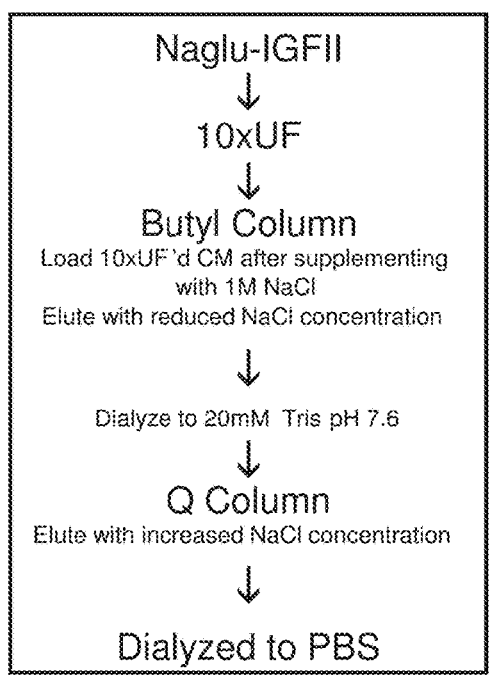 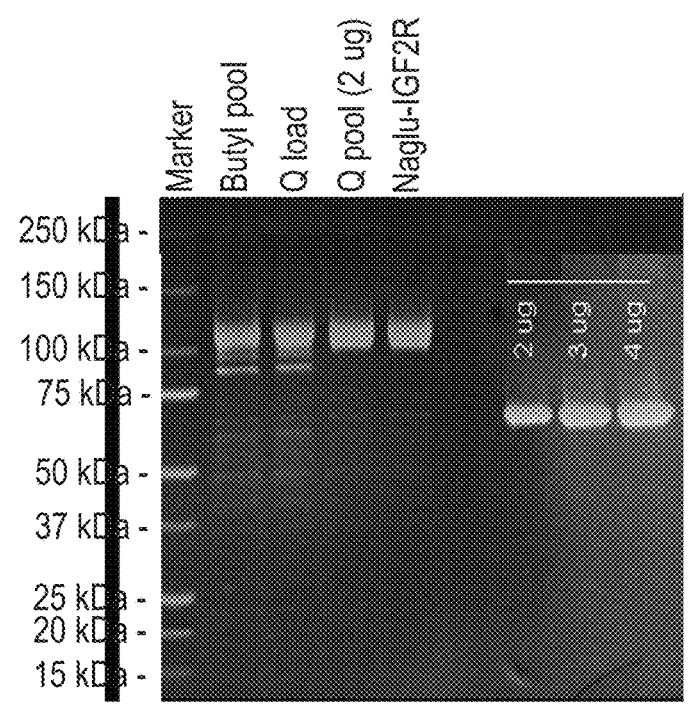
Fig. 7A    Fig. 7B
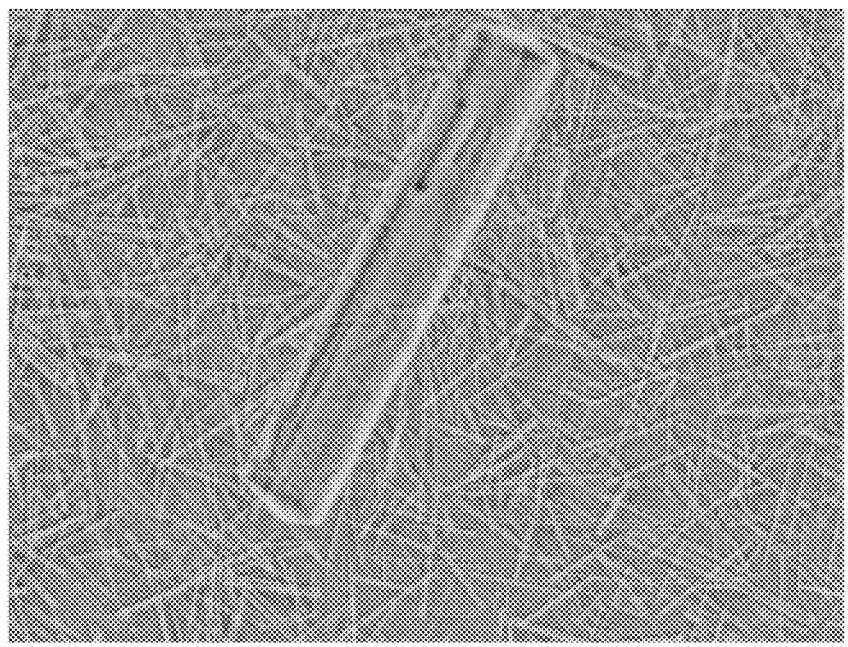
Fig. 8

Port-A-Cath Low Profile Intrathecal Implantable Access System

ID NO: 5)-IGFII

SEQUENCE LISTING

```
<160> NUMBER OF SEQ ID NOS: 7

<210> SEQ ID NO 1
<211> LENGTH: 720
<212> TYPE: PRT
<213> ORGANISM: Homo sapiens

<400> SEQUENCE: 1

Asp Glu Ala Arg Glu Ala Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
        35                  40                  45

Ala Ala Arg Val Arg Val Arg Gly Ser Thr Gly Val Ala Ala Ala Ala
    50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Tyr Gln Asn Val
```

```
              100                 105                 110
Cys Thr Gln Ser Tyr Ser Phe Val Trp Trp Asp Trp Ala Arg Trp Glu
              115                 120                 125

Arg Glu Ile Asp Trp Met Ala Leu Asn Gly Ile Asn Leu Ala Leu Ala
130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
              165                 170                 175

Ala Trp Gly Arg Met Gly Asn Leu His Thr Trp Asp Gly Pro Leu Pro
              180                 185                 190

Pro Ser Trp His Ile Lys Gln Leu Tyr Leu Gln His Arg Val Leu Asp
              195                 200                 205

Gln Met Arg Ser Phe Gly Met Thr Pro Val Leu Pro Ala Phe Ala Gly
              210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                    245                 250                 255

Leu Leu Ala Pro Glu Asp Pro Ile Phe Pro Ile Ile Gly Ser Leu Phe
              260                 265                 270

Leu Arg Glu Leu Ile Lys Glu Phe Gly Thr Asp His Ile Tyr Gly Ala
              275                 280                 285

Asp Thr Phe Asn Glu Met Gln Pro Pro Ser Ser Glu Pro Ser Tyr Leu
              290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
                    325                 330                 335

Phe Trp Gly Pro Ala Gln Ile Arg Ala Val Leu Gly Ala Val Pro Arg
              340                 345                 350

Gly Arg Leu Leu Val Leu Asp Leu Phe Ala Glu Ser Gln Pro Val Tyr
              355                 360                 365

Thr Arg Thr Ala Ser Phe Gln Gly Gln Pro Phe Ile Trp Cys Met Leu
              370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
              405                 410                 415

Gly Thr Gly Met Ala Pro Glu Gly Ile Ser Gln Asn Glu Val Val Tyr
              420                 425                 430

Ser Leu Met Ala Glu Leu Gly Trp Arg Lys Asp Pro Val Pro Asp Leu
              435                 440                 445

Ala Ala Trp Val Thr Ser Phe Ala Ala Arg Arg Tyr Gly Val Ser His
              450                 455                 460

Pro Asp Ala Gly Ala Ala Trp Arg Leu Leu Leu Arg Ser Val Tyr Asn
465                 470                 475                 480

Cys Ser Gly Glu Ala Cys Arg Gly His Asn Arg Ser Pro Leu Val Arg
                    485                 490                 495

Arg Pro Ser Leu Gln Met Asn Thr Ser Ile Trp Tyr Asn Arg Ser Asp
              500                 505                 510

Val Phe Glu Ala Trp Arg Leu Leu Leu Thr Ser Ala Pro Ser Leu Ala
              515                 520                 525
```

Thr Ser Pro Ala Phe Arg Tyr Asp Leu Leu Asp Leu Thr Arg Gln Ala
        530                 535                 540

Val Gln Glu Leu Val Ser Leu Tyr Tyr Glu Glu Ala Arg Ser Ala Tyr
545                 550                 555                 560

Leu Ser Lys Glu Leu Ala Ser Leu Leu Arg Ala Gly Gly Val Leu Ala
                565                 570                 575

Tyr Glu Leu Leu Pro Ala Leu Asp Glu Val Leu Ala Ser Asp Ser Arg
                580                 585                 590

Phe Leu Leu Gly Ser Trp Leu Glu Gln Ala Arg Ala Ala Ala Val Ser
            595                 600                 605

Glu Ala Glu Ala Asp Phe Tyr Gln Gln Asn Ser Arg Tyr Gln Leu Thr
610                 615                 620

Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
                660                 665                 670

Gln Phe Asp Lys Asn Val Phe Gln Leu Glu Gln Ala Phe Val Leu Ser
            675                 680                 685

Lys Gln Arg Tyr Pro Ser Gln Pro Arg Gly Asp Thr Val Asp Leu Ala
690                 695                 700

Lys Lys Ile Phe Leu Lys Tyr Tyr Pro Arg Trp Val Ala Gly Ser Trp
705                 710                 715                 720

<210> SEQ ID NO 2
<211> LENGTH: 743
<212> TYPE: PRT
<213> ORGANISM: Homo sapiens

<400> SEQUENCE: 2

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
            20                  25                  30

Arg Ala Leu Val Ala Arg Leu Leu Gly Pro Gly Pro Ala Ala Asp Phe
        35                  40                  45

Ser Val Ser Val Glu Arg Ala Leu Ala Ala Lys Pro Gly Leu Asp Thr
    50                  55                  60

Tyr Ser Leu Gly Gly Gly Gly Ala Ala Arg Val Arg Val Arg Gly Ser
65                  70                  75                  80

Thr Gly Val Ala Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe

```
            180                 185                 190
Phe Thr Gly Pro Ala Phe Leu Ala Trp Gly Arg Met Gly Asn Leu His
            195                 200                 205
Thr Trp Asp Gly Pro Leu Pro Pro Ser Trp His Ile Lys Gln Leu Tyr
            210                 215                 220
Leu Gln His Arg Val Leu Asp Gln Met Arg Ser Phe Gly Met Thr Pro
225                 230                 235                 240
Val Leu Pro Ala Phe Ala Gly His Val Pro Glu Ala Val Thr Arg Val
                    245                 250                 255
Phe Pro Gln Val Asn Val Thr Lys Met Gly Ser Trp Gly His Phe Asn
            260                 265                 270
Cys Ser Tyr Ser Cys Ser Phe Leu Leu Ala Pro Glu Asp Pro Ile Phe
            275                 280                 285
Pro Ile Ile Gly Ser Leu Phe Leu Arg Glu Leu Ile Lys Glu Phe Gly
            290                 295                 300
Thr Asp His Ile Tyr Gly Ala Asp Thr Phe Asn Glu Met Gln Pro Pro
305                 310                 315                 320
Ser Ser Glu Pro Ser Tyr Leu Ala Ala Ala Thr Thr Ala Val Tyr Glu
                    325                 330                 335
Ala Met Thr Ala Val Asp Thr Glu Ala Val Trp Leu Leu Gln Gly Trp
                    340                 345                 350
Leu Phe Gln His Gln Pro Gln Phe Trp Gly Pro Ala Gln Ile Arg Ala
            355                 360                 365
Val Leu Gly Ala Val Pro Arg Gly Arg Leu Leu Val Leu Asp Leu Phe
            370                 375                 380
Ala Glu Ser Gln Pro Val Tyr Thr Arg Thr Ala Ser Phe Gln Gly Gln
385                 390                 395                 400
Pro Phe Ile Trp Cys Met Leu His Asn Phe Gly Gly Asn His Gly Leu
                    405                 410                 415
Phe Gly Ala Leu Glu Ala Val Asn Gly Gly Pro Glu Ala Ala Arg Leu
            420                 425                 430
Phe Pro Asn Ser Thr Met Val Gly Thr Gly Met Ala Pro Glu Gly Ile
            435                 440                 445
Ser Gln Asn Glu Val Val Tyr Ser Leu Met Ala Glu Leu Gly Trp Arg
            450                 455                 460
Lys Asp Pro Val Pro Asp Leu Ala Ala Trp Val Thr Ser Phe Ala Ala
465                 470                 475                 480
Arg Arg Tyr Gly Val Ser His Pro Asp Ala Gly Ala Ala Trp Arg Leu
                    485                 490                 495
Leu Leu Arg Ser Val Tyr Asn Cys Ser Gly Glu Ala Cys Arg Gly His
            500                 505                 510
Asn Arg Ser Pro Leu Val Arg Arg Pro Ser Leu Gln Met Asn Thr Ser
            515                 520                 525
Ile Trp Tyr Asn Arg Ser Asp Val Phe Glu Ala Trp Arg Leu Leu Leu
            530                 535                 540
Thr Ser Ala Pro Ser Leu Ala Thr Ser Pro Ala Phe Arg Tyr Asp Leu
545                 550                 555                 560
Leu Asp Leu Thr Arg Gln Ala Val Gln Glu Leu Val Ser Leu Tyr Tyr
                    565                 570                 575
Glu Glu Ala Arg Ser Ala Tyr Leu Ser Lys Glu Leu Ala Ser Leu Leu
                    580                 585                 590
Arg Ala Gly Gly Val Leu Ala Tyr Glu Leu Leu Pro Ala Leu Asp Glu
            595                 600                 605
```

-continued

Val Leu Ala Ser Asp Ser Arg Phe Leu Leu Gly Ser Trp Leu Glu Gln
            610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
            690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp
            740

<210> SEQ ID NO 3
<211> LENGTH: 67
<212> TYPE: PRT
<213> ORGANISM: Homo sapiens

<400> SEQUENCE: 3

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 4
<211> LENGTH: 13
<212> TYPE: PRT
<213> ORGANISM: Artificial Sequence
<220> FEATURE:
<223> OTHER INFORMATION: Synthetic linker peptide

<400> SEQUENCE: 4

Gly Gly Gly Gly Gly Ala Ala Ala Ala Gly Gly Gly Gly
1               5                   10

<210> SEQ ID NO 5
<211> LENGTH: 51
<212> TYPE: PRT
<213> ORGANISM: Artificial Sequence
<220> FEATURE:
<223> OTHER INFORMATION: synthetic linker peptide

<400> SEQUENCE: 5

Gly Ala Pro Gly Gly Gly Gly Ala Ala Ala Ala Gly Gly Gly Gly
1               5                   10                  15

Gly Ala Pro Gly Gly Gly Gly Ala Ala Ala Ala Gly Gly Gly Gly
            20                  25                  30

```
Gly Ala Pro Gly Gly Gly Gly Ala Ala Ala Gly Gly Gly Gly
        35                  40                  45

Gly Ala Pro
    50

<210> SEQ ID NO 6
<211> LENGTH: 837
<212> TYPE: PRT
<213> ORGANISM: Artificial Sequence
<220> FEATURE:
<223> OTHER INFORMATION: Protein Sequence of Recombinant Naglu-IGFII
      Fusion Protein

<400> SEQUENCE: 6

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
                20                  25                  30

Leu Ala Ala Lys Pro Gly Leu Asp Thr Tyr Ser Leu Gly Gly Gly Gly
            35                  40                  45

Ala Ala Arg Val Arg Val Arg Gly Ser Thr Gly Val Ala Ala Ala
50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Gln Asn Val
            100                 105                 110

Cys Thr Gln Ser Tyr Ser Phe Val Trp Trp Asp Trp Ala Arg Trp Glu
            115                 120                 125

Arg Glu Ile Asp Trp Met Ala Leu Asn Gly Ile Asn Leu Ala Leu Ala
130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
            180                 185                 190

Pro Ser Trp His Ile Lys Gln Leu Tyr Leu Gln His Arg Val Leu Asp
        195                 200                 205

Gln Met Arg Ser Phe Gly Met Thr Pro Val Leu Pro Ala Phe Ala Gly
    210                 215                 220

His Val Pro Glu Ala Val Thr Arg Val Phe Pro Gln Val Asn Val Thr
225                 230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
            260                 265                 270

Leu Arg Glu Leu Ile Lys Glu Phe Gly Thr Asp His Ile Tyr Gly Ala
        275                 280                 285

Asp Thr Phe Asn Glu Met Gln Pro Pro Ser Ser Glu Pro Ser Tyr Leu
    290                 295                 300

Ala Ala Ala Thr Thr Ala Val Tyr Glu Ala Met Thr Ala Val Asp Thr
305                 310                 315                 320

Glu Ala Val Trp Leu Leu Gln Gly Trp Leu Phe Gln His Gln Pro Gln
```

```
                    325                 330                 335
Phe Trp Gly Pro Ala Gln Ile Arg Ala Val Leu Gly Ala Val Pro Arg
                340                 345                 350

Gly Arg Leu Leu Val Leu Asp Leu Phe Ala Glu Ser Gln Pro Val Tyr
            355                 360                 365

Thr Arg Thr Ala Ser Phe Gln Gly Gln Pro Phe Ile Trp Cys Met Leu
        370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
                420                 425                 430

Ser Leu Met Ala Glu Leu Gly Trp Arg Lys Asp Pro Val Pro Asp Leu
            435                 440                 445

Ala Ala Trp Val Thr Ser Phe Ala Ala Arg Arg Tyr Gly Val Ser His
        450                 455                 460

Pro Asp Ala Gly Ala Ala Trp Arg Leu Leu Leu Arg Ser Val Tyr Asn
465                 470                 475                 480

Cys Ser Gly Glu Ala Cys Arg Gly His Asn Arg Ser Pro Leu Val Arg
                485                 490                 495

Arg Pro Ser Leu Gln Met Asn Thr Ser Ile Trp Tyr Asn Arg Ser Asp
                500                 505                 510

Val Phe Glu Ala Trp Arg Leu Leu Leu Thr Ser Ala Pro Ser Leu Ala
            515                 520                 525

Thr Ser Pro Ala Phe Arg Tyr Asp Leu Leu Asp Leu Thr Arg Gln Ala
        530                 535                 540

Val Gln Glu Leu Val Ser Leu Tyr Tyr Glu Ala Arg Ser Ala Tyr
545                 550                 555                 560

Leu Ser Lys Glu Leu Ala Ser Leu Leu Arg Ala Gly Gly Val Leu Ala
                565                 570                 575

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Ala Val Ser
        595                 600                 605

Glu Ala Glu Ala Asp Phe Tyr Glu Gln Asn Ser Arg Tyr Gln Leu Thr
610                 615                 620

Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
            660                 665                 670

Gln Phe Asp Lys Asn Val Phe Gln Leu Glu Gln Ala Phe Val Leu Ser
        675                 680                 685

Lys Gln Arg Tyr Pro Ser Gln Pro Arg Gly Asp Thr Val Asp Leu Ala
    690                 695                 700

Lys Lys Ile Phe Leu Lys Tyr Tyr Pro Arg Trp Val Ala Gly Ser Trp
705                 710                 715                 720

Gly Ala Pro Gly Gly Gly Gly Ala Ala Ala Ala Gly Gly
                725                 730                 735

Gly Gly Gly Ala Pro Gly Gly Gly Gly Ala Ala Ala Ala Gly
            740                 745                 750
```

```
Gly Gly Gly Gly Gly Ala Pro Gly Gly Gly Gly Ala Ala Ala Ala
            755             760             765

Ala Gly Gly Gly Gly Gly Ala Pro Leu Cys Gly Gly Glu Leu Val
    770             775             780

Asp Thr Leu Gln Phe Val Cys Gly Asp Arg Gly Phe Tyr Phe Ser Arg
785             790             795                     800

Pro Ala Ser Arg Val Ser Arg Arg Ser Arg Gly Ile Val Glu Glu Cys
                805             810                 815

Cys Phe Arg Ser Cys Asp Leu Ala Leu Leu Glu Thr Tyr Cys Ala Thr
                820             825             830

Pro Ala Lys Ser Glu
        835

<210> SEQ ID NO 7
<211> LENGTH: 6
<212> TYPE: PRT
<213> ORGANISM: Artificial Sequence
<220> FEATURE:
<223> OTHER INFORMATION: synthetic linker peptide

<400> SEQUENCE: 7

Gly Gly Gly Gly Gly Pro
1               5
```

THERAPEUTIC FUSION PROTEIN COMPRISING AN ALPHA-N-ACETYLGLUCOSAMINIDASE AND A LYSOSOMAL TARGETING MOIETY

CROSS REFERENCE TO RELATED APPLICATIONS

This application is a continuation of U.S. patent application Ser. No. 13/892,076, filed on May 10, 2013, now U.S. Pat. No. 9,814,764, which is a continuation of U.S. patent application Ser. No. 13/168,969 filed on Jun. 25, 2011, which claims priority to U.S. Provisional Patent Application Ser. Nos. 61/495,268 filed on Jun. 9, 2011; 61/476,210, filed Apr. 15, 2011; 61/449,225, filed Mar. 4, 2011; 61/442,115, filed Feb. 11, 2011; 61/435,710, filed Jan. 24, 2011; 61/387,862, filed Sep. 29, 2010; 61/360,786, filed Jul. 1, 2010; and 61/358,857 filed Jun. 25, 2010; the entirety of each of which is hereby incorporated by reference.

This application relates to US applications entitled "CNS Delivery of Therapeutic Agents;" filed on Jun. 25, 2011; "Methods and Compositions for CNS Delivery of Heparan N-Sulfatase," filed on Jun. 25, 2011; "Methods and Compositions for CNS Delivery of Iduronate-2-Sulfatase," filed on Jun. 25, 2011; "Methods and Compositions for CNS Delivery of β-Galactocerebrosidase," filed on Jun. 25, 2011; "Methods and Compositions for CNS Delivery of Arylsulfatase A," filed on Jun. 25, 2011; the entirety of each of which is hereby incorporated by reference.

SEQUENCE LISTING

In accordance with 37 C.F.R. § 1.52(e)(5), a Sequence Listing in the form of a text file (entitled "Sequence Listing", identified as U.S. Ser. No. 15/811,545_ST25.txt, created on May 30, 2018 of 93,330 bytes) is incorporated herein by reference in its entirety.

(4) In paragraph [0237], under the heading Table 7: Linker Sequence, please amend as follows:
Naglu-GAPGGGGGAAAAGGGGGAPGGGG-
GAAAAGGGGGAPGGGGGAAAAGGGGGAP (SEQ ID NO: 5)-IGFII

BACKGROUND

Enzyme replacement therapy (ERT) involves the systemic administration of natural or recombinantly-derived proteins and/or enzymes to a subject. Approved therapies are typically administered to subjects intravenously and are generally effective in treating the somatic symptoms of the underlying enzyme deficiency. As a result of the limited distribution of the intravenously administered protein and/or enzyme into the cells and tissues of the central nervous system (CNS), the treatment of diseases having a CNS etiology has been especially challenging because the intravenously administered proteins and/or enzymes do not adequately cross the blood-brain barrier (BBB).

The blood-brain barrier (BBB) is a structural system comprised of endothelial cells that functions to protect the central nervous system (CNS) from deleterious substances in the blood stream, such as bacteria, macromolecules (e.g., proteins) and other hydrophilic molecules, by limiting the diffusion of such substances across the BBB and into the underlying cerebrospinal fluid (CSF) and CNS.

There are several ways of circumventing the BBB to enhance brain delivery of a therapeutic agent including direct intra-cranial injection, transient permeabilization of the BBB, and modification of the active agent to alter tissue distribution. Direct injection of a therapeutic agent into brain tissue bypasses the vasculature completely, but suffers primarily from the risk of complications (infection, tissue damage, immune responsive) incurred by intra-cranial injections and poor diffusion of the active agent from the site of administration. To date, direct administration of proteins into the brain substance has not achieved significant therapeutic effect due to diffusion barriers and the limited volume of therapeutic that can be administered. Convection-assisted diffusion has been studied via catheters placed in the brain parenchyma using slow, long-term infusions (Bobo, et al., Proc. Natl. Acad. Sci. U.S.A. 91, 2076-2080 (1994); Nguyen, et al. J. Neurosurg. 98, 584-590 (2003)), but no approved therapies currently use this approach for long-term therapy. In addition, the placement of intracerebral catheters is very invasive and less desirable as a clinical alternative.

Intrathecal (IT) injection, or the administration of proteins to the cerebrospinal fluid (CSF), has also been attempted but has not yet yielded therapeutic success. A major challenge in this treatment has been the tendency of the active agent to bind the ependymal lining of the ventricle very tightly which prevented subsequent diffusion. Currently, there are no approved products for the treatment of brain genetic disease by administration directly to the CSF.

In fact, many believed that the barrier to diffusion at the brain's surface, as well as the lack of effective and convenient delivery methods, were too great an obstacle to achieve adequate therapeutic effect in the brain for any disease.

Sanfilippo syndrome, or mucopolysaccharidosis III (MPS III), is a rare genetic disorder characterized by the deficiency of enzymes involved in the degradation of glycosaminoglycans (GAG). In the absence of enzyme, partially degraded GAG molecules cannot be cleared from the body and accumulate in lysosomes of various tissues, resulting in progressive widespread somatic dysfunction (Neufeld and Muenzer, 2001).

Four distinct forms of MPS III, designated MPS IIIA, B, C, and D, have been identified. Each represents a deficiency in one of four enzymes involved in the degradation of the GAG heparan sulfate. All forms include varying degrees of the same clinical symptoms, including coarse facial features, hepatosplenomegaly, corneal clouding and skeletal deformities. Most notably, however, is the severe and progressive loss of cognitive ability, which is tied not only to the accumulation of heparan sulfate in neurons, but also the subsequent elevation of the gangliosides GM2, GM3 and GD2 caused by primary GAG accumulation (Walkley 1998).

Mucopolysaccharidosis type IIIB (MPS IIIB; Sanfilippo B disease) is an autosomal recessive disorder that is characterized by a deficiency of the enzyme alpha-N-acetylglucosaminidase (Naglu). In the absence of this enzyme, GAG heparan sulfate accumulates in lysosomes of neurons and glial cells, with lesser accumulation outside the brain. To date, no CNS symptoms resulting from Sanfilippo B disease has successfully been treated by any means available.

Thus, there remains a great need to effectively deliver therapeutic agents to the brain. More particularly, there is a great need for more effective delivery of therapeutic agents to the central nervous system for the treatment of Sanfilippo B disease.

SUMMARY

The present invention provides compositions and methods for effective treatment of Sanfilippo B disease. The present invention is, in part, based on the discovery that intrathecal administration of an alpha-N-acetylglucosaminidase (Naglu) protein (e.g., a Naglu-IGFII fusion protein) to an animal disease model is unexpectedly effective in treating (e.g., ameliorating, inhibiting, or delaying onset of) various symptoms of Sanfilippo B disease, including massive GAG accumulation in various brain tissues.

Prior to the present invention, it was reported that a recombinantly produced Naglu protein lacks mannose-6-phosphate (M6P) which is typically required for lysosomal targeting. Therefore, the enzyme replacement therapy for Sanfilippo B disease presents a unique challenge because of the predominant manifestation in the CNS and the lack of M6P residues. As discussed below, the present inventors have demonstrated that intrathecal injections of Naglu-IGFII has resulted in surprisingly effective reduction of GAG accumulation in the brain, reversal of lysosomal storage in brain tissue, and penetration of Naglu-IGFII into the brain parenchyma. Without wishing to be bound by any particular theory, it is contemplated that a lysosomal targeting moiety such as an IGF-II moiety may overcome the lack of mannose-6-phosphate (M6P), resulting in M6P-independent lysosomal targeting in the target tissues. These results indicate that IT administration of an Naglu-protein, such as, a Naglu-IGFII fusion protein, can be used to effectively treat the Sanfilippo B disease. Thus, the present invention represents a significant breakthrough in the Sanfilippo B enzyme replacement therapy.

Although IT administration is described in the Examples below, It is contemplated that a Naglu fusion protein according to the present invention delivered to the CNS directly or indirectly via various techniques and routes including, but not limited to, intraparenchymal, intracerebral, intraventricular cerebral (ICV), intrathecal (e.g., IT-Lumbar, IT-cisterna magna) administrations and any other techniques and routes for injection directly or indirectly to the CNS and/or CSF.

In one aspect, the present invention provides methods of treating Sanfilippo syndrome type B (San B) disease including a step of administering intrathecally to a subject in need of treatment a alpha-N-acetylglucosaminidase (Naglu) protein. As used herein, a suitable Naglu protein can be a synthetic, recombinant, gene-activated or natural protein.

In some embodiments, a suitable Naglu protein is a recombinant Naglu protein. In some embodiments, the recombinant Naglu protein is a fusion protein comprising a Naglu domain and a lysosomal targeting moiety. In certain embodiments, the Naglu domain comprises an amino acid sequence at least 70% (e.g., at least 75%, 80%, 85%, 90%, 95%, or 98%) identical to SEQ ID NO:1 (mature human Naglu protein). In some embodiments, the Naglu domain comprises an amino acid sequence at least 95% identical to SEQ ID NO:1 (mature human Naglu protein). In some embodiments, the Naglu domain comprises an amino acid sequence identical to SEQ ID NO:1 (mature human Naglu protein).

In some embodiments, the lysosomal targeting moiety is an IGF-II moiety. In certain embodiments, the IGF-II moiety comprises an amino acid sequence at least 70% (e.g., at least 75%, 80%, 85%, 90%, 95%, or 98%) identical to mature human IGF-II (SEQ ID NO:3). In certain embodiments, the IGF-II moiety comprises an amino acid sequence at least 80% identical to mature human IGF-II (SEQ ID NO:3). In certain embodiments, the IGF-II moiety comprises an amino acid sequence at least 90% identical to mature human IGF-II (SEQ ID NO:3). In some embodiments, the IGF-II moiety comprises an amino acid sequence including residues 8-67 of mature human IGF-II (SEQ ID NO:3).

In some embodiments, the fusion protein further comprises a linker between the Naglu domain and the lysosomal targeting moiety. In certain embodiments, the linker comprises one or more amino acid sequences of GGGG-GAAAAGGGG (SEQ ID NO:4). In certain embodiments, the amino acid sequence of GGGGGAAAAGGGG (SEQ ID NO:4) is present in tandem repeats.

In some embodiments, the linker further comprises one or more GAP sequences. In certain embodiments, the linker comprises amino acid sequence of GAPGGGG-GAAAAGGGGGAPGGGGGAAAAGGGGGAPGGGG-GAAAAGGGGGAP (SEQ ID NO:5).

In some embodiments, the lysosomal targeting moiety is fused directly or via the linker to the C-terminus of the Naglu domain. In some embodiments, the lysosomal targeting moiety is fused directly or via the linker to the N-terminus of the Naglu domain.

In some embodiments, the recombinant protein is produced from human cells. In some embodiments, the recombinant protein is produced from CHO cells.

In some embodiments, the intrathecal administration results in delivery of the Naglu protein in one or more target brain tissues. In certain embodiments, the one or more target brain tissues are selected from the group consisting of tissues from gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof.

In some embodiments, the Naglu protein is delivered to neurons, glial cells, perivascular cells and/or meningeal cells. In some embodiments, the Naglu protein is further delivered to the neurons in the spinal cord.

In some embodiments, the intrathecal administration further results in systemic delivery of the Naglu protein in peripheral target tissues. In certain embodiments, the peripheral target tissues are selected from liver, kidney, spleen, and/or heart.

In some embodiments, the intrathecal administration results in lysosomal localization in brain target tissues, spinal cord neurons and/or peripheral target tissues.

In some embodiments, the intrathecal administration results in reduction of lysosomal storage (e.g., accumulated enzyme substrate) in the brain target tissues, spinal cord neurons and/or peripheral target tissues. In certain embodiments, the lysosomal storage is determined by LAMP-1 staining. In some embodiments, the lysosomal storage is reduced by at least 20%, 40%, 50%, 60%, 80%, 90%, 1-fold, 1.5-fold, or 2-fold as compared to a control.

In some embodiments, the intrathecal administration results in reduced vacuolization in neurons. In certain embodiments, the neurons comprises Purkinje cells.

In some embodiments, the intrathecal administration results in increased Naglu enzymatic activity in the brain target tissues, spinal cord neurons and/or peripheral target tissues. In certain embodiments, the Naglu enzymatic activity is increased by at least 1-fold, 2-fold, 3-fold, 4-fold, 5-fold, 6-fold, 7-fold, 8-fold, 9-fold or 10-fold as compared to a control (e.g., the pre-treatment endogenous enzymatic activity in the subject). In certain embodiments, the increased Naglu enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg. As used herein, nmol/hr/mg defines the specific activity of the enzyme, which measures nmol substrate hydrolyzed per hour per mg of enzyme.

In some embodiments, the Naglu enzymatic activity is increased in the lumbar region. In certain embodiments, the increased Naglu enzymatic activity in the lumbar region is at least approximately 500 nmol/hr/mg, 600 nmol/hr/mg, 700 nmol/hr/mg, 800 nmol/hr/mg, 900 nmol/hr/mg, 1000 nmol/hr/mg, 1500 nmol/hr/mg, 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In some embodiments, the intrathecal administration results in reduced intensity, severity, or frequency, or delayed onset of at least one symptom or feature of the Sanfilippo B Syndrome. In some embodiments, the at least one symptom or feature of the San B disease is hearing loss, delayed speech development, deficits in motor skills, hyperactivity, mental retardation, aggressiveness and/or sleep disturbances.

In some embodiments, the intrathecal administration takes place once every two weeks. In some embodiments, the intrathecal administration takes place once every month. In some embodiments, the intrathecal administration takes place once every two months. In some embodiments, the intrathecal administration is used in conjunction with intravenous administration. In some embodiments, the intravenous administration is no more frequent than once every week. In some embodiments, the intravenous administration is no more frequent than once every two weeks. In some embodiments, the intravenous administration is no more frequent than once every month. In some embodiments, the intravenous administration is no more frequent than once every two months. In certain embodiments, the intraveneous administration is more frequent than monthly administration, such as twice weekly, weekly, every other week, or twice monthly.

In some embodiments, intraveneous and intrathecal administrations are performed on the same day. In some embodiments, the intraveneous and intrathecal administrations are not performed within a certain amount of time of each other, such as not within at least 2 days, within at least 3 days, within at least 4 days, within at least 5 days, within at least 6 days, within at least 7 days, or within at least one week. In some embodiments, intraveneous and intrathecal administrations are performed on an alternating schedule, such as alternating administrations weekly, every other week, twice monthly, or monthly. In some embodiments, an intrathecal administration replaces an intravenous administration in an administration schedule, such as in a schedule of intraveneous administration weekly, every other week, twice monthly, or monthly, every third or fourth or fifth administration in that schedule can be replaced with an intrathecal administration in place of an intraveneous administration.

In some embodiments, intraveneous and intrathecal administrations are performed sequentially, such as performing intraveneous administrations first (e.g., weekly, every other week, twice monthly, or monthly dosing for two weeks, a month, two months, three months, four months, five months, six months, a year or more) followed by IT administrations (e.g., weekly, every other week, twice monthly, or monthly dosing for more than two weeks, a month, two months, three months, four months, five months, six months, a year or more). In some embodiments, intrathecal administrations are performed first (e.g., weekly, every other week, twice monthly, monthly, once every two months, once every three months dosing for two weeks, a month, two months, three months, four months, five months, six months, a year or more) followed by intravenous administrations (e.g., weekly, every other week, twice monthly, or monthly dosing for more than two weeks, a month, two months, three months, four months, five months, six months, a year or more).

In some embodiments, the intrathecal administration is used in absence of intravenous administration.

In some embodiments, the intrathecal administration is used in absence of concurrent immunosuppressive therapy.

In some embodiments, the Naglu fusion protein is administered at a concentration greater than approximately 20 mg/ml.

In another aspect, the present invention provides therapeutic fusion proteins including a Naglu domain; a lysosomal targeting moiety, and wherein, once administered, the therapeutic fusion protein is targeted to lysosomes and is therapeutically active in vivo.

In some embodiments, the Naglu domain comprises an amino acid sequence at least 70% (e.g., at least 75%, 80%, 85%, 90%, 95%, or 98%) identical to SEQ ID NO:1 (mature human Naglu protein). In some embodiments, the Naglu domain comprises an amino acid sequence identical to SEQ ID NO:1 (mature human Naglu protein). In some embodiments, the lysosomal targeting moiety is an IGF-II moiety. In some embodiments, the IGF-II moiety comprises an amino acid sequence at least 70% (e.g., at least 75%, 80%, 85%, 90%, 95%, or 98%) identical to mature human IGF-II (SEQ ID NO:3). In some embodiments, the IGF-II moiety comprises an amino acid sequence including residues 8-67 of mature human IGF-II (SEQ ID NO:3).

In some embodiments, the fusion protein further comprises a linker between the Naglu domain and the lysosomal targeting moiety. In some embodiments, the linker comprises amino acid sequence of GAPGGGGGAAAAGGGG-GAPGGGGGAAAAGGGGGAPGGGGGAAAAGGGG-GAP (SEQ ID NO:5).

In some embodiments, the lysosomal targeting moiety is fused directly or via the linker to the C-terminus of the Naglu domain. In some embodiments, In yet another aspect, the present invention provides therapeutic fusion proteins including an amino acid sequence at least 70% (e.g., at least 75%, 80%, 85%, 90%, 95%, or 98%) identical to SEQ ID NO:6 (the full-length Naglu-IGF-II fusion protein), wherein, once administered, the therapeutic fusion protein is targeted to lysosomes and is therapeutically active in vivo.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

FIG. 1 illustrates an exemplary rhNaglu, Naglu-IGFII, Naglu-TAT and Naglu Kif, and the outcome of proof of concept study (POC). (no. of aa/theori mw—number of amino acid and theoretical molecular weight).

FIG. 2: FIG. 2 illustrates an exemplary PerT-Naglu and Naglu-ApoE. These two modifications of rhNaglu were produced to examine transporting enzyme through the BBB.

FIG. 3A illustrates an exemplary IGF II molecule showing amino sequences 8-67 as the binding sequence to IGF II receptor (figure modified from Hashimoto 1995, 20). FIG. 3B illustrates exemplary M6P I IGF II receptor and its 15 domains. Domains 3 and 9 bind mannose-6-phosphate, while domain 5 binds mannose-6-phosphate diester. Domain 11 binds to IGF II (figure modified from Bohnsack 2009, 22).

FIG. 4 illustrates exemplary wave production of Naglu-IGFII clone 47dz2-15. The average production of Naglu-IGFII was 0.5 pcd (pictogram per-million-cells per-day). GH, growth harvest; H1 to H8, harvest 1-8.

FIG. 5 illustrates an exemplary Western blot analysis of harvests from wave production in FIG. 4. Lanes were normalized by the volume of culture medium.

FIG. 6 illustrates an exemplary Western blot analysis of Naglu-IGFII before and after deglycosylation with PNGase F. The dispersed band before PNGase F digestion is the typical appearance of lysosomal proteins when glycosylated. Upon PNGase F digestion, the protein band became sharp and condensed, an appearance consistent with that of an uniform polypeptide chain. The analysis with anti-human Naglu and anti-IGFII antibody confirmed that only intact molecules of Naglu-IGFII were expressed by clone 47dz2-15. "−", indicates harvest material before PNGaseF digestion. "+", indicates harvest material after PNGase F digestion.

FIGS. 7A and 7B: FIG. 7A illustrates an exemplary purification scheme of Naglu-IGFII. FIG. 7B illustrates the SDS-PAGE gel for the step-wise purification of Naglu-IGFII from conditioned media FIG. 8: FIG. 8 illustrates exemplary crystals of Naglu-Kif protein.

FIG. 9 illustrates an exemplary crystal structure of Naglu represented as a cartoon model. Three domains are indicated as Domain I, Domain II and Domain III. Glycans are shown as sticks. Catalytic residues are E316 and E446.

FIG. 10 illustrates an exemplary trimeric structure of Naglu. Active sites of the three molecules are marked.

FIG. 11 illustrates exemplary primary fibroblast cells from normal human used for cellular internalization study of rhNaglu and Naglu-IGFII. Cellular uptake of rhNaglu was minimum, while the cellular uptake of Naglu-IGFII was much pronounced. The saturating curve of Naglu-IGFII internalization indicated a receptor mediated uptake. This uptake was inhibited by IGFII, but not by mannose-6-phosphate.

FIG. 12 depicts exemplary confocal microscopy study using Sanfilippo B patient's fibroblast cells (GM01426). Extensive internalization of Naglu-IGFII, and co-localization of Naglu-IGFII with Lamp-1 was observed (right panels), unlike for rhNaglu (left panels).

FIG. 13 illustrates exemplary-Naglu activity in wild type (WT), Naglu−/− (KO) and heterozygote Naglu+/− (Het) mouse. Total deficiency of Naglu in Sanfilippo B mouse was observed in brain, liver, kidney and spleen.

FIG. 14 depicts superior (upper left panel) and lateral (upper right panel) view of the mouse brain to indicate the site of IC injection and the sectioning plane for histology analyses. Lower left panel illustrates a transversal section of mouse brain viewed at 1× magnification. Boxed area indicates the field for 4× microscopy image. Lower right panel illustrates this 4× image of histology slide. Box A indicate the field of 40× microscopy image as shown in FIGS. 15 and 16.

FIG. 15 depicts exemplary immunohistochemistry (using anti-human Naglu monoclonal antibody) of the cerebral cortex in Sanfilippo B mice 7 days after IC injection 40×. Both rhNaglu (lower left panel) and Naglu-IGFII (lower right panel) exhibited extensive cellular uptake in neurons as well as in glial cells, and the distribution and cellular uptake patterns were very similar between the two proteins. The upper panel illustrates the vehicle treated control.

FIG. 16 depicts exemplary LAMP-1 immunostaining of the cerebral cortex 40×. Comparing to the brain of wild type mouse (upper left panel), increased lysosomal storage was obvious in the brain of vehicle treated (upper right panel) Sanfilippo B mouse, as demonstrated by the increased LAMP-1 immunostaining positive spots. The brain of both rhNalgu (lower left panel) and Naglu-IGFII (lower right panel) treated Sanfilippo B mouse exhibited reduction of lysosomal storage that was very similar to wild type mouse.

FIG. 17A illustrates widespread reduction of cellular vacuolation in the white matter tissues of Naglu-deficient mice IT-administered Naglu (right panel) relative to the same Naglu-deficient mice that were administered the vehicle (left panel). FIG. 17B illustrates a marked reduction in lysosomal associated membrane protein 1 (LAMP1) immunostaining in the white matter tissues of Naglu-deficient mice intrathecally-administered Naglu relative to the same Naglu-deficient mice (right panel) that were administered a vehicle (left panel).

FIGS. 18A-B quantitatively illustrates and compares the concentration of LAMP measured in the cerebral cortex, caudate nucleus and putamen (CP), thalamus (TH), cerebellum (CBL) and white matter (WM) of the Naglu-deficient mice which were administered Naglu relative to both the wild-type and Naglu-deficient mice that were administered a vehicle. The LAMP-positive areas in each area of brain tissue analyzed were further reduced following the intrathecal administration of three doses of Naglu over the course of seven days (FIG. 18A) relative to two doses of Naglu over the course of two weeks (FIG. 18B).

FIG. 19 illustrates an exemplary midsagittal anatomical diagram of human CNS, and is used as a reference to demonstrate the site of IT injection in wt cannulated Rat (i.e., the approximate anatomic location of IT injection in the spinal cord, and the cerebral cortex region where tissues were taken for immunohistochemistry study).

FIG. 20 illustrates exemplary Naglu activity in the brain after IT injection. Naglu activity was significantly higher in the brain of Naglu-TAT and Naglu-IGFII injected wt rat.

FIG. 21 depicts exemplary Naglu immunostaining of the cerebral cortex of rhNaglu (upper middle panel), Naglu-TAT (upper right panel), Naglu-IGFII (lower left panel), Naglu-kif (lower middle panel) and PerT-Naglu (lower right panel) treated wt cannulated rat 24 hr after IT injection 20×. The upper left panel shows the vehicle treated rat. Naglu-IGFII was the only protein exhibited extensive distribution well into the parenchyma of the brain. Cellular uptake into neurons and glial cells were also evident in Naglu-IGFII treated rat. On the other hand, in rhNaglu, Naglu-TAT, Naglu kif and PerT-Naglu treated groups, the protein only remained in the meninges (M)

FIG. 22 depicts exemplary high power magnification of the selected slides from FIG. 21. Upper panel, in the rhNaglu treated wt cannulated rat, rhNaglu remained at the meninges (M) only, no positive staining found in the parenchyma of the brain. Lower panel, in Naglu-IGFII treated wt cannulated rat, extensive distribution was observed well into the parenchyma of the brain, and cellular uptake was observed in neurons and glial cells.

FIG. 23 illustrates exemplary Naglu activity in brain and liver 24 hr after last IT injection. Among the three treated groups, Naglu activity in the brain did not show significant differences, the same is true for the Naglu activity in the liver. This result implied that the Naglu activity detected in the brain and liver was mostly due to the last injection which occurred 24 hr prior to sacrifice. It is unclear at this point as to why there was significantly higher Naglu activity in the liver compared to in the brain. A thorough pharmacokinetic study after IT injection may help interpret the difference.

FIG. 24 illustrates exemplary total GAG level in the brain and liver after IT injection of Naglu-IGFII. Total GAG in the brain of vehicle treated Sanfilippo B mice exhibited progressive increases, a reflection of accumulative effect as the Sanfilippo B mice ageing. A statistically significant reduction of GAG in the brain was observed in 3× injection group ($p<0.05$). Statistically significant reductions of GAG in liver were also observed in 2× and 3× injection groups ($p<0.05$). The quicker and more drastic change of GAG level in liver than in the brain is a phenomenon that has been observed in other lysosomal storage disease mouse model, such as hunter syndrome (internal communications).

FIG. 25 depicts exemplary biodistribution of Naglu in the brain of Sanfilippo B mice after IT injection. Naglu immunofluorescent staining revealed the Naglu-IGFII protein on the meninges (M) and parenchyma of the brain. Cellular uptake was observed in the 2× (lower left panel) and 3× (lower right panel) injection groups. The 1× injection group (upper right panel) and vehicle treated group (upper left panel) are also shown. G: glial cells.

FIG. 26 illustrates exemplary coronal section of the mouse brain. Boxes indicate where the pictures for LAMP-1 immunostaining were taken. To demonstrate the extent of protein distribution and efficacy, cerebral cortex and subcortical tissues such as caudate nucleus, thalamus and white matter were selected for LAMP1 immunostaining.

FIG. 27 depicts exemplary LAMP1 immunostaining of cerebral cortex 40×. Compared to the brain of wild type mouse (upper left panel), increased lysosomal storage was observed in the brain of vehicle treated Sanfilippo B mouse (upper right panel), as seen by the increased LAMP1 immunostaining positive spots. Reduction of lysosomal storage after Naglu-IGFII IT injection was evident by the reduced size of positive spots of 2× injection treated Sanfilippo B mouse brain (lower left panel), and the reduced size and number of positive spots of the 3× injection treated Sanfilippo B mouse brain (lower right panel).

FIG. 28 depicts exemplary LAMP-1 immunostaining of caudate nucleus, a subcortical nucleus 40×. Similar to what was seen in cerebral cortex, compared to the brain of wild type mouse (upper left panel), increased lysosomal storage was observed in the brain of vehicle treated Sanfilippo B mouse (upper right panel), as seen by the increased LAMP1 immunostaining positive spots. Reduction of lysosomal storage after Naglu-IGFII IT injection was evident by the reduced size of positive spots of 2× injection treated Sanfilippo B mouse brain (lower left panel), and the reduced size and number of positive spots of the 3× injection treated Sanfilippo B mouse brain (lower right panel).

FIG. 29 depicts exemplary LAMP-1 immunostaining of the thalamus, a diencephalic nuclei 40×. Reduction of lysosomal storage after Naglu-IGFII IT injection was evident by the reduced size of positive spots of 2× injection treated Sanfilippo B mouse brain (lower left panel), and the reduced size and number of positive spots of the 3× injection treated Sanfilippo B mouse brain (lower right panel). The brain of wild type mouse (upper left panel) and the brain of vehicle treated Sanfilippo B mouse (upper right panel) are also shown.

FIG. 30 depicts exemplary LAMP-1 immunostaining of white matter 40×. The longitudinal track of neuron axon fibers distinguishes the white matter from grey matters presented in FIGS. 26-29. None the less, the same pattern of increases of lysosomal storage could be seen in vehicle treated Sanfilippo B mouse's brain (upper right panel) when compared to the wild type mouse (upper left panel). Reduction of lysosomal storage after Naglu-IGFII IT injection was evident by the reduced size and reduced number of positive spots in the 2× (lower left panel) and 3× (lower right panel) injection treated Sanfilippo B mouse brain.

FIG. 31 depicts exemplary LAMP-1 immunostaining of the cerebellar cortex. Similar effect of reduction of lysosomal storage was observed in cerebellar cortex as in other areas of the brain, as discussed above (shown in panel views as above). The morphology of cerebellar cortex was evident by the densely populated granular neurons, the hypocellular Molecular layer, and the single layer of Purkinje neurons between the granular neurons and the molecular layer. Purkinje neurons were identified by the large cytoplasm and occasional dendrites protruding into the Molecular layer.

FIG. 32 illustrates exemplary Naglu staining in the brain (upper panel), spinal cord (middle panel) and liver (lower panel). In the brain and spinal cord, injected Naglu was detected in meninges (M) only by IHC and no Naglu positive staining was detected in any other regions. In the liver, sinunoidal cells (S) were Naglu positive and no Naglu uptake was found in hepatocytes (H).

FIG. 33 illustrates exemplary LAMP immunostaining and H & E staining of the liver and spinal cord. Compared with the vehicle animals (middle and lower left panels), LAMP staining was decreased throughout in both livers (middle right panel) and spinal cords (lower right panel) treated with Naglu. H & E staining showed cellular vacuolation in hepatocytes was evidently reduced in the treated group (upper right panel) compared with vehicle treated animals (upper left panel).

FIG. 34A and FIG. 34B illustrate exemplary H & E staining of the brain regions (i.e., cortex (upper panel), white matter (middle panel), and thalamus (lower panel) in FIG. 34A; and hippocampus (upper panel), cerebellum (middle panel), and brainstem (lower panel) in FIG. 34B) demonstrating morphology improvement of the brain after 6 every other week IT injection of Naglu for 3 months. In the treated brain (right panels), the cellular vacuolation (arrows) in all examined regions decreased compared with the vehicle group (left panels).

FIG. 35A and FIG. 35B illustrate exemplary LAMP immunostaining in various brain regions (i.e., cortex (upper panel), white matter (middle panel), and thalamus (lower panel) in FIG. 35A; and hippocampus (upper panel), cerebellum (middle panel), and brainstem (lower panel) in FIG. 35B) after 6 IT Naglu injections for 3 months. Compared with the vehicle treated group (left panels), Naglu IT administration to Sanfilippo B mice resulted in a reduction of lysosomal activity in all examined regions revealed by LAMP immunostaining (right panels). This reduction was characterized by the decrease in the number of LAMP positive cells, smaller cell size and lighter staining. A marked reduction was found in the cerebellum and brainstem, which are located in the caudate part of the brain close to the spinal cord, compared with other brain regions. A clear reduction was also found in the deep brain regions, including the white matter, hippocampus, and thalamus.

Figure 36A:
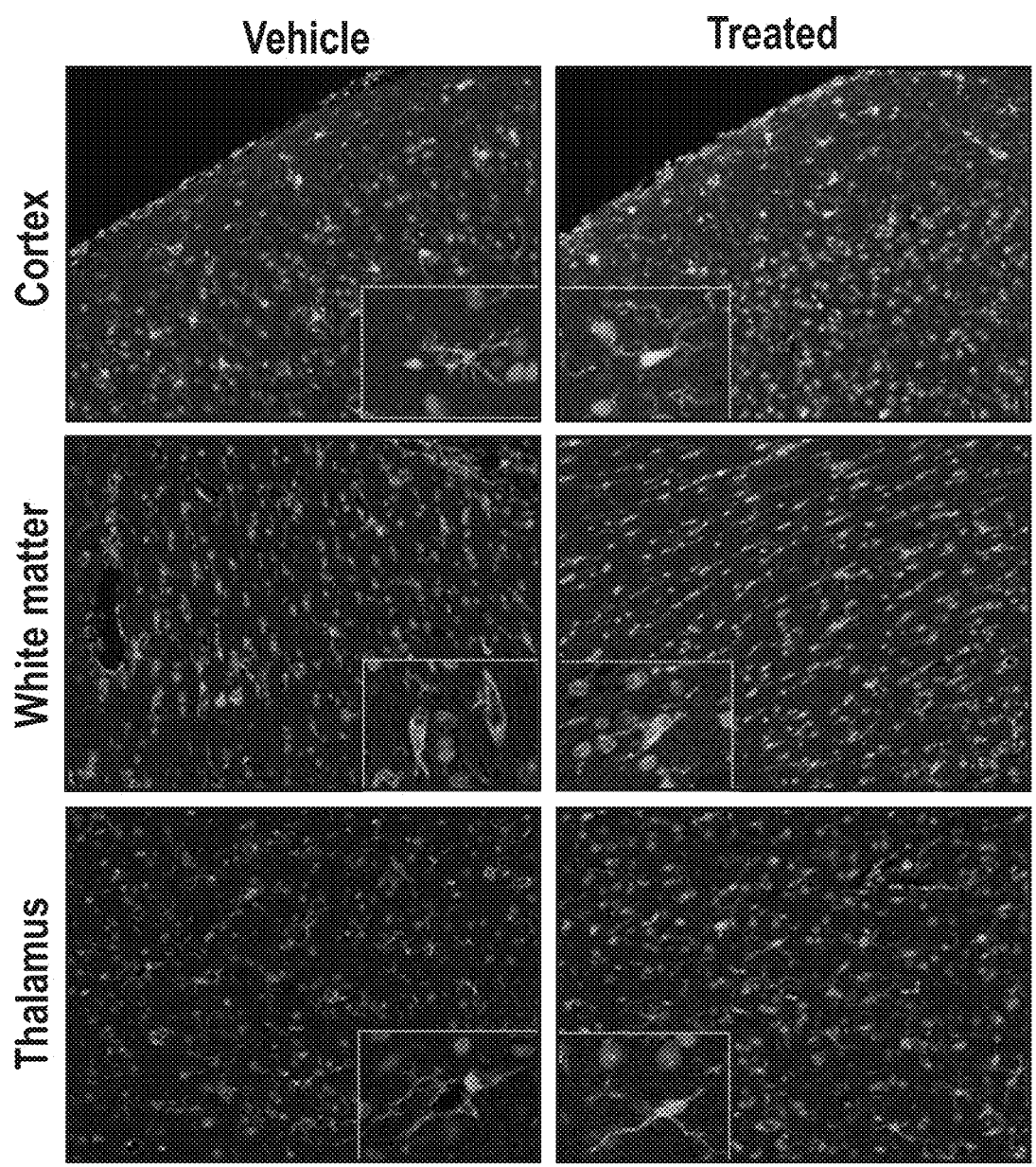
Figure 36B:
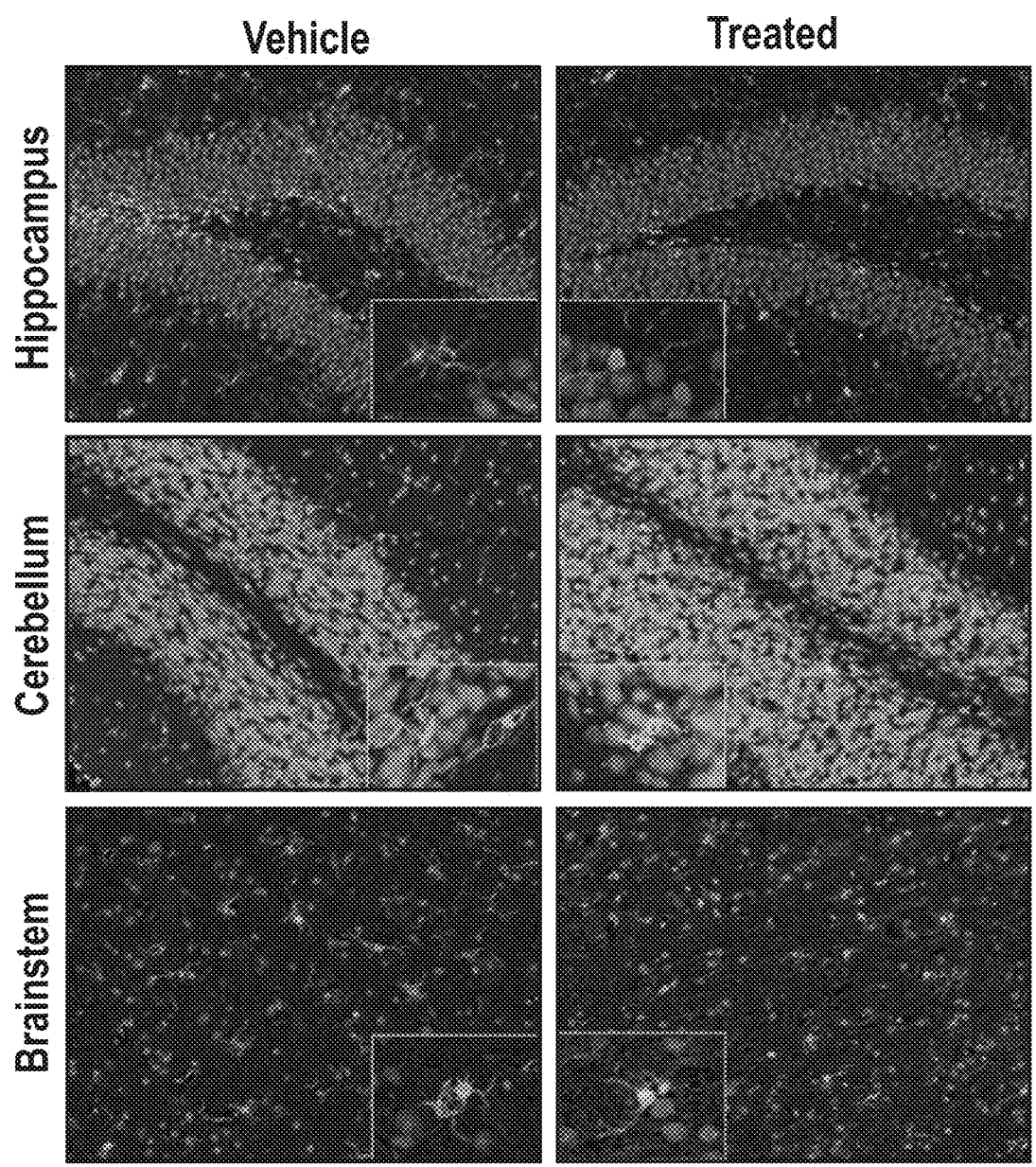

FIGS. 36A and 36B: FIG. 36A and FIG. 36B illustrate exemplary Iba IHC in various brain regions (i.e., cortex (upper panel), white matter (middle panel), and thalamus (lower panel) in FIG. 36A; and hippocampus (upper panel), cerebellum (middle panel), and brainstem (lower panel) in FIG. 36B) after 6 IT Naglu injections for 3 months, which revealed activation of microglial cells. Compared with vehicle treated group (left panels), no decrease in the number of positive cells and staining intensity was observed in Naglu treated group (right panels). However, the cellular morphology of positive microglial cells changed with reduced cell size in all examined brain regions compared to large and vacuolated one in the vehicle group (inserts).

Figure 27:
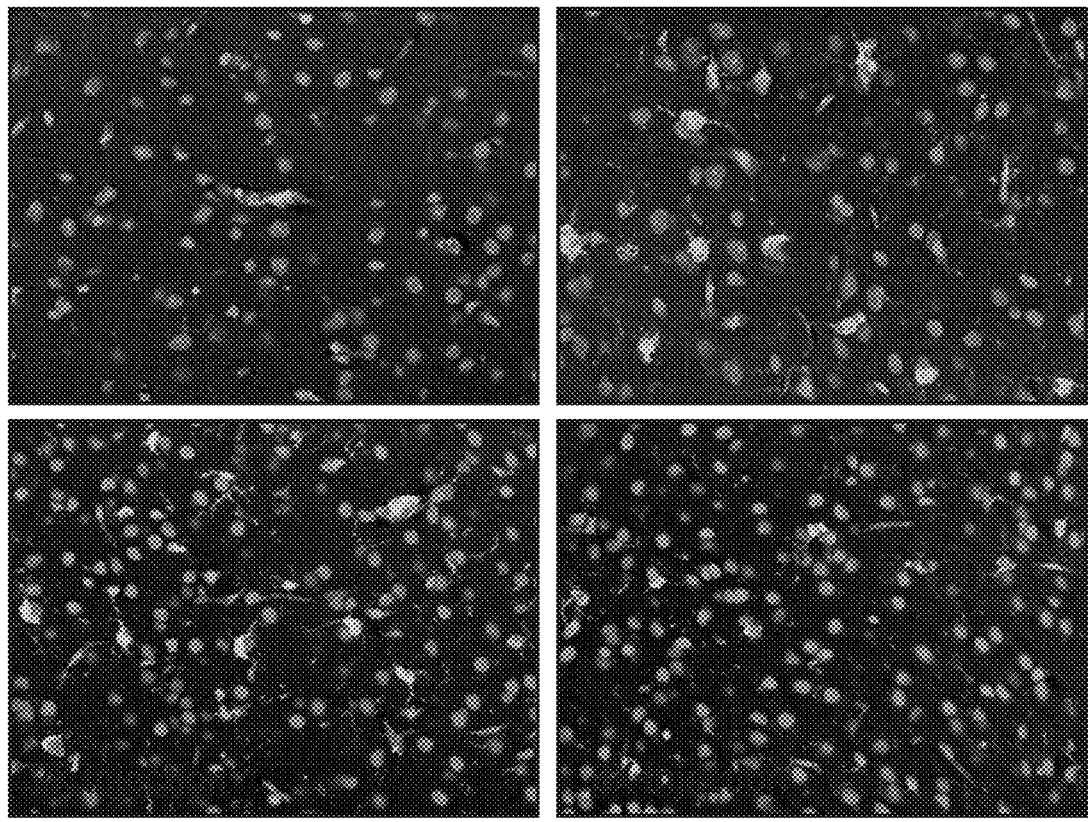
FIG. 27.
Figure 28:
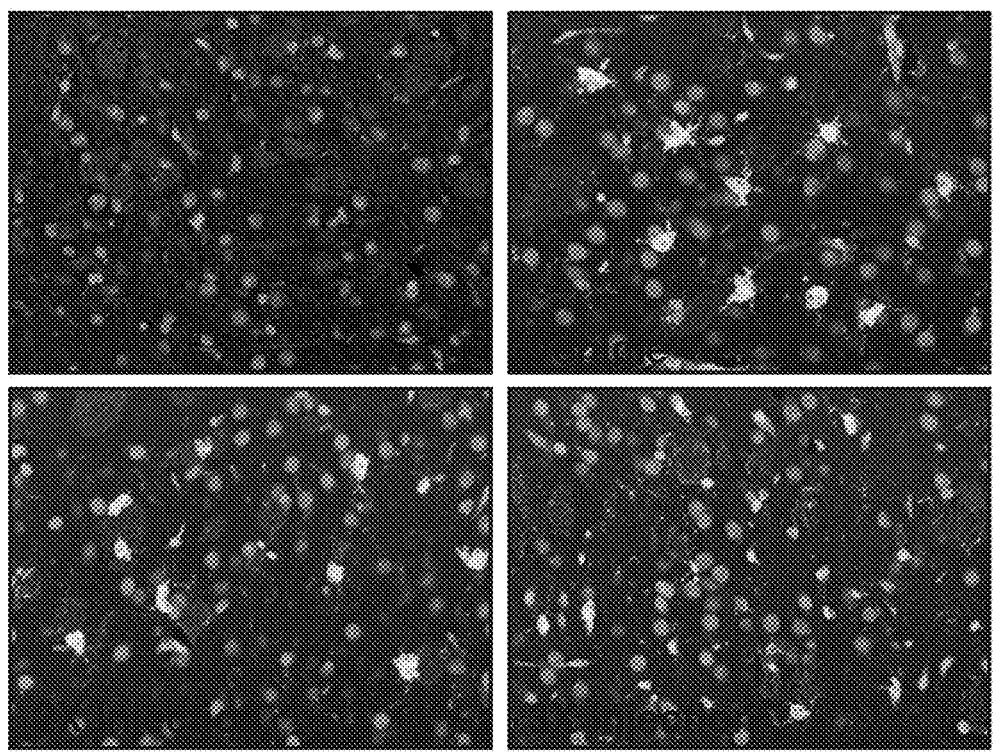
FIG. 28.
Figure 29:
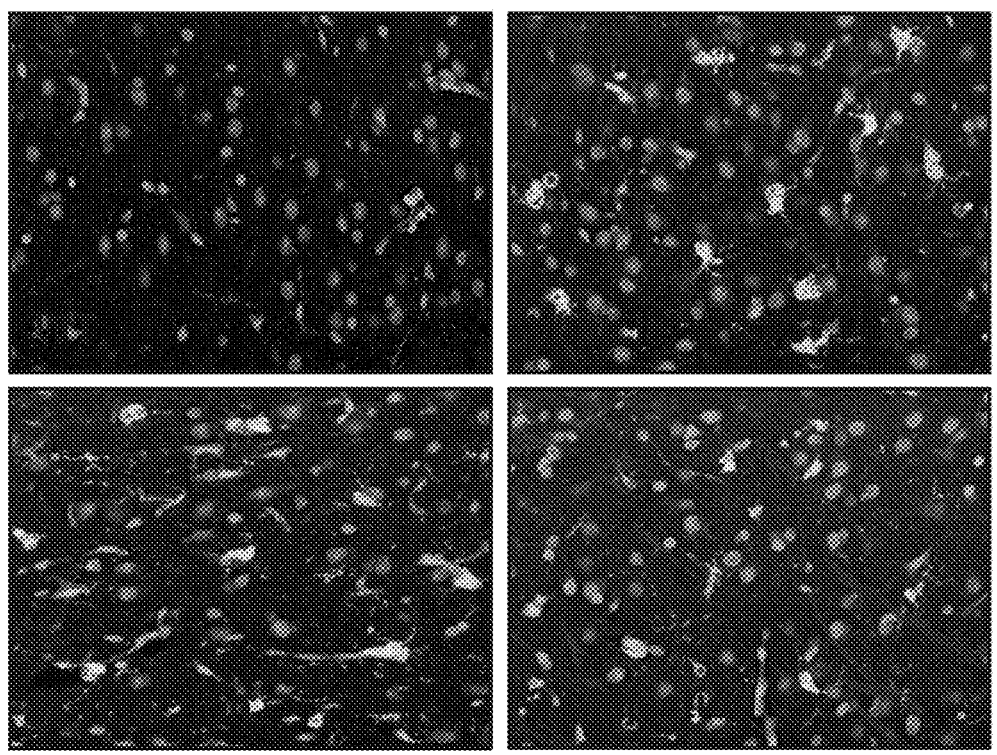
FIG. 29.
Figure 30:
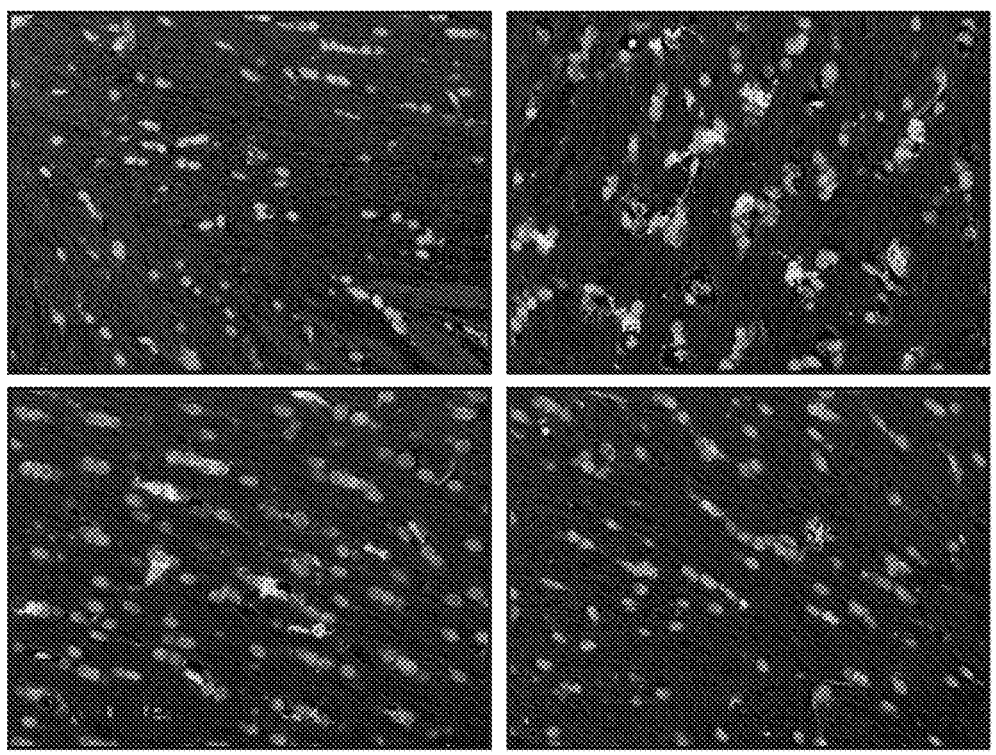
FIG. 30.
Figure 31:
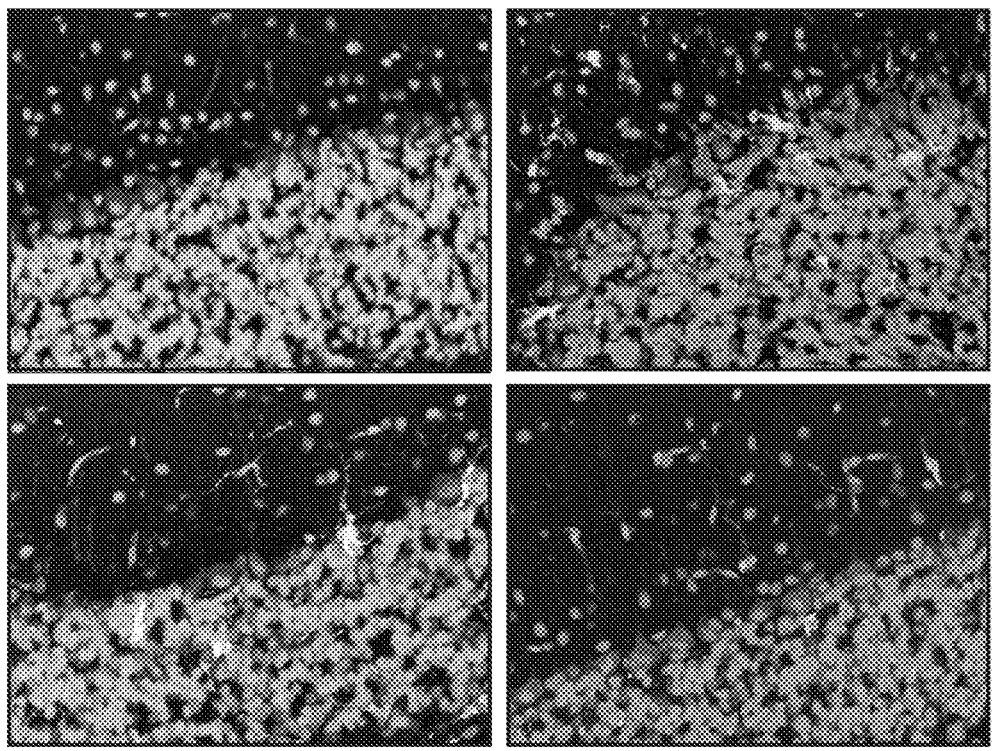
FIG. 31.
Figure 37A:
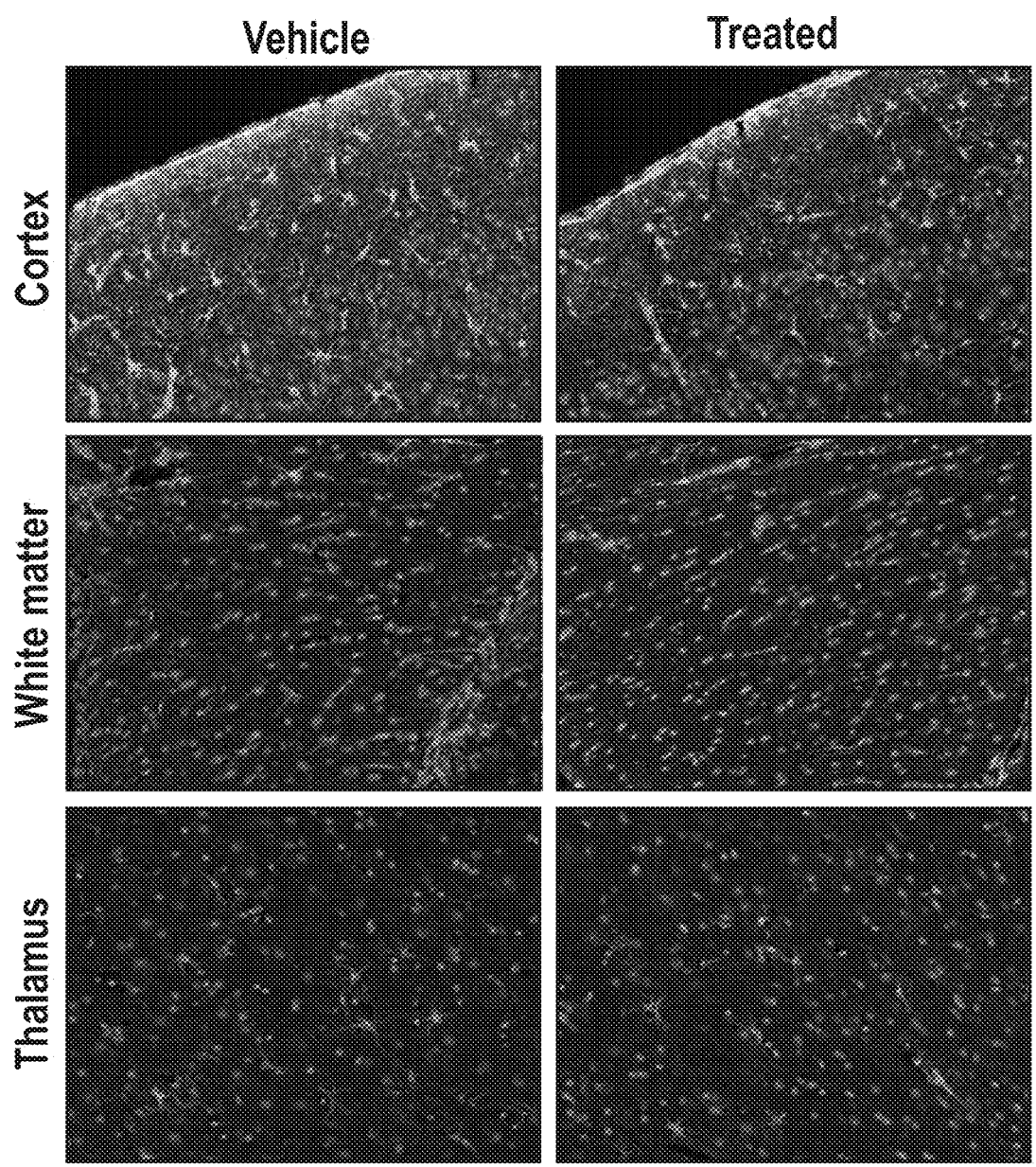
Figure 37B:
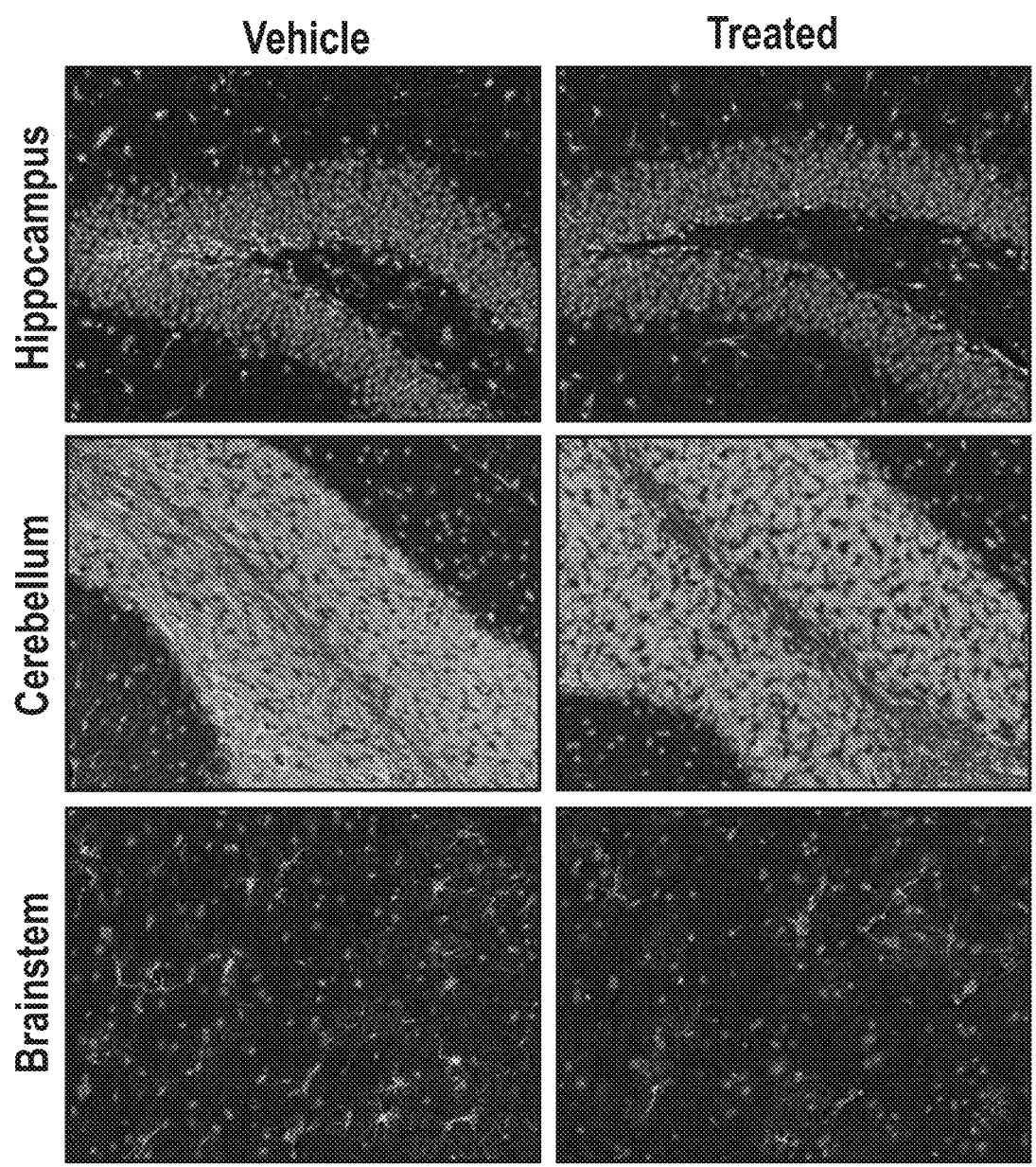

FIGS. 37A and 37B: FIG. 37A and FIG. 27B illustrate exemplary GFAP IHC in various brain regions (i.e., cortex (upper panel), white matter (middle panel), and thalamus (lower panel) in FIG. 37A; and hippocampus (upper panel), cerebellum (middle panel), and brainstem (lower panel) in FIG. 37B) after 6 IT Naglu injections for 3 months, which revealed astrocytic activation. Compared with the vehicle treated group (left panels), GFAP positive staining was decreased in the cerebellum and brainstem, and slightly decreased in other examined regions (right panels).

Figure 38:
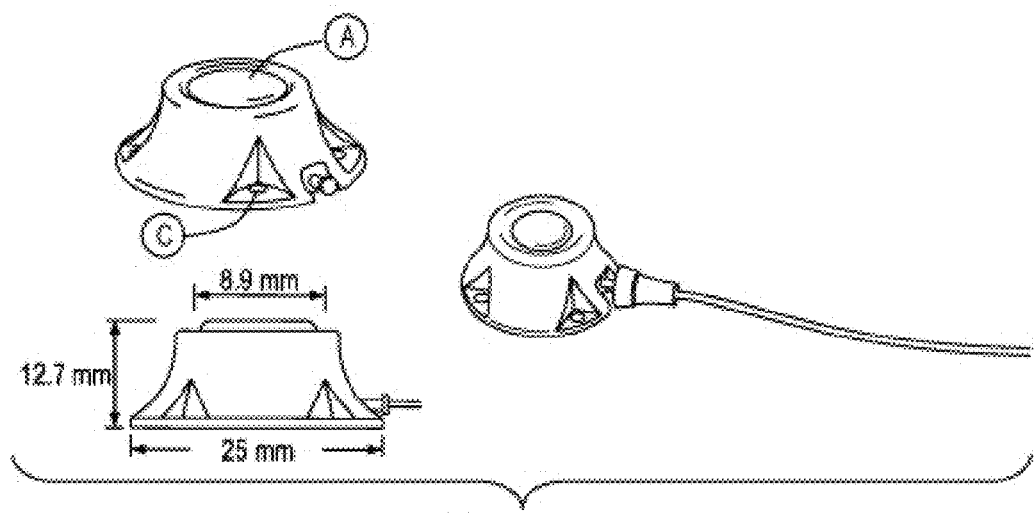

FIG. 38: FIG. 38 depicts an exemplary intrathecal drug delivery device (IDDD).

Figure 39:
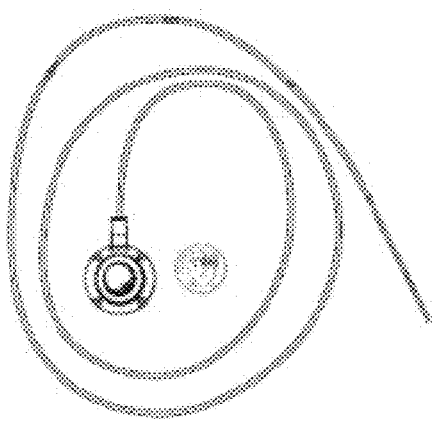

FIG. 39: FIG. 39 depicts an exemplary PORT-A-CATH® low profile intrathecal implantable access system.

Figure 40:
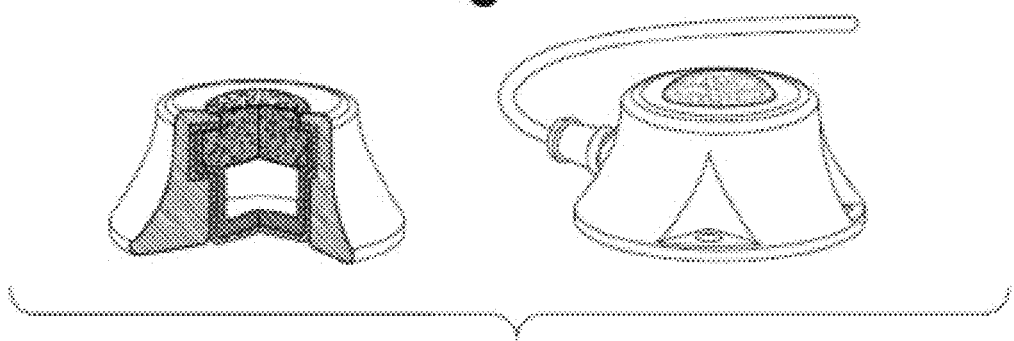

FIG. 40: FIG. 40 depicts an exemplary intrathecal drug delivery device (IDDD).

Figure 41:
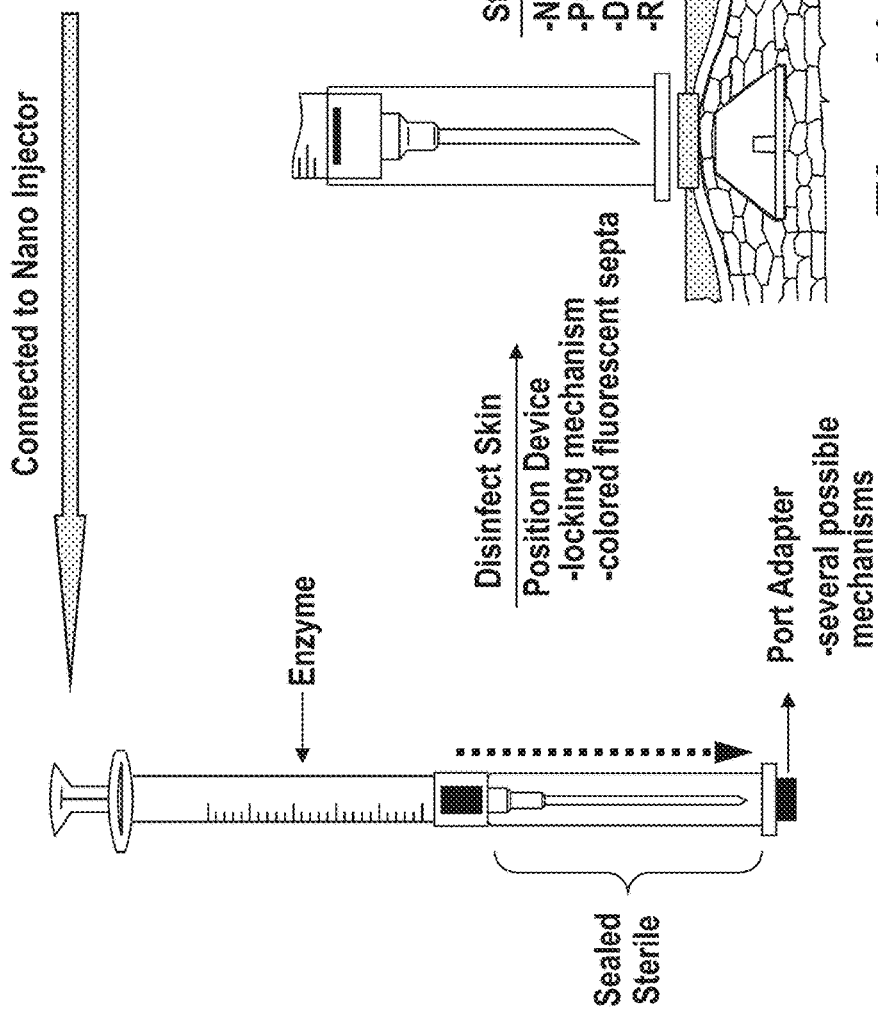

FIG. 41: FIG. 41 depicts an exemplary intrathecal drug delivery device (IDDD), which allows for in-home administration for CNS enzyme replacement therapy (ERT).

Figure 42:
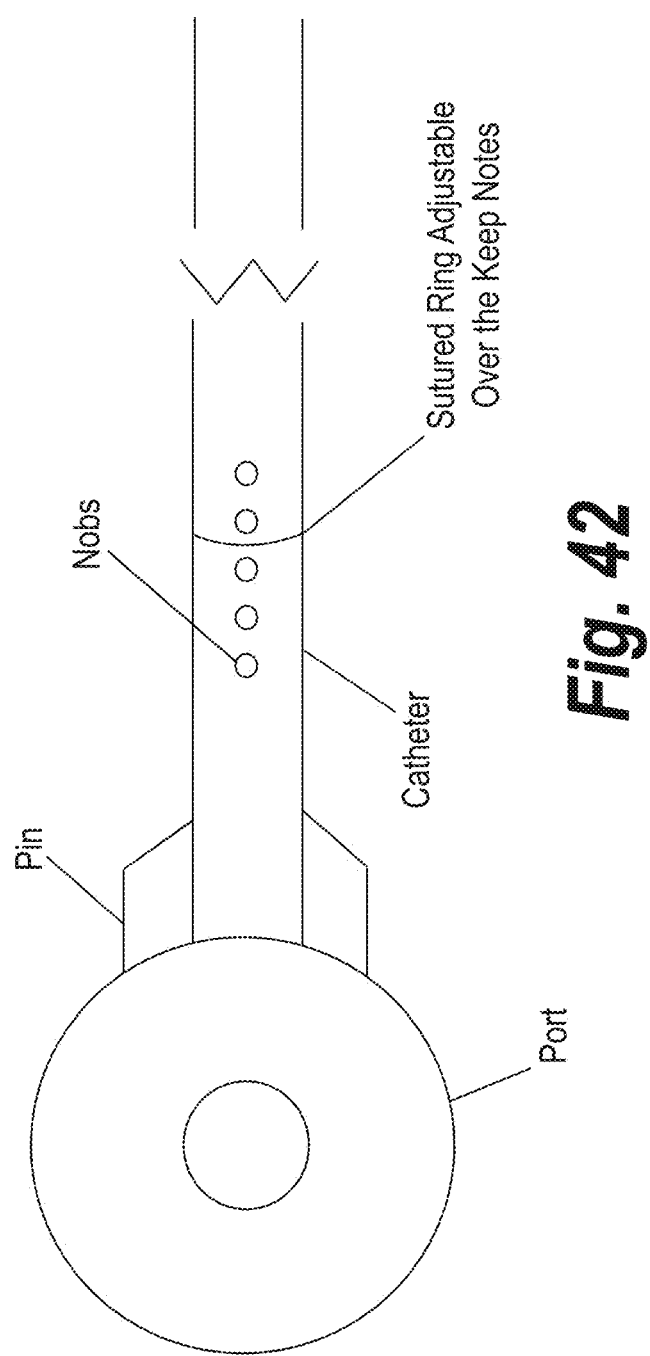

FIG. 42: FIG. 42 illustrates and exemplary diagram of an intrathecal drug delivery device (IDDD) with a securing mechanism.

Figure 43A:
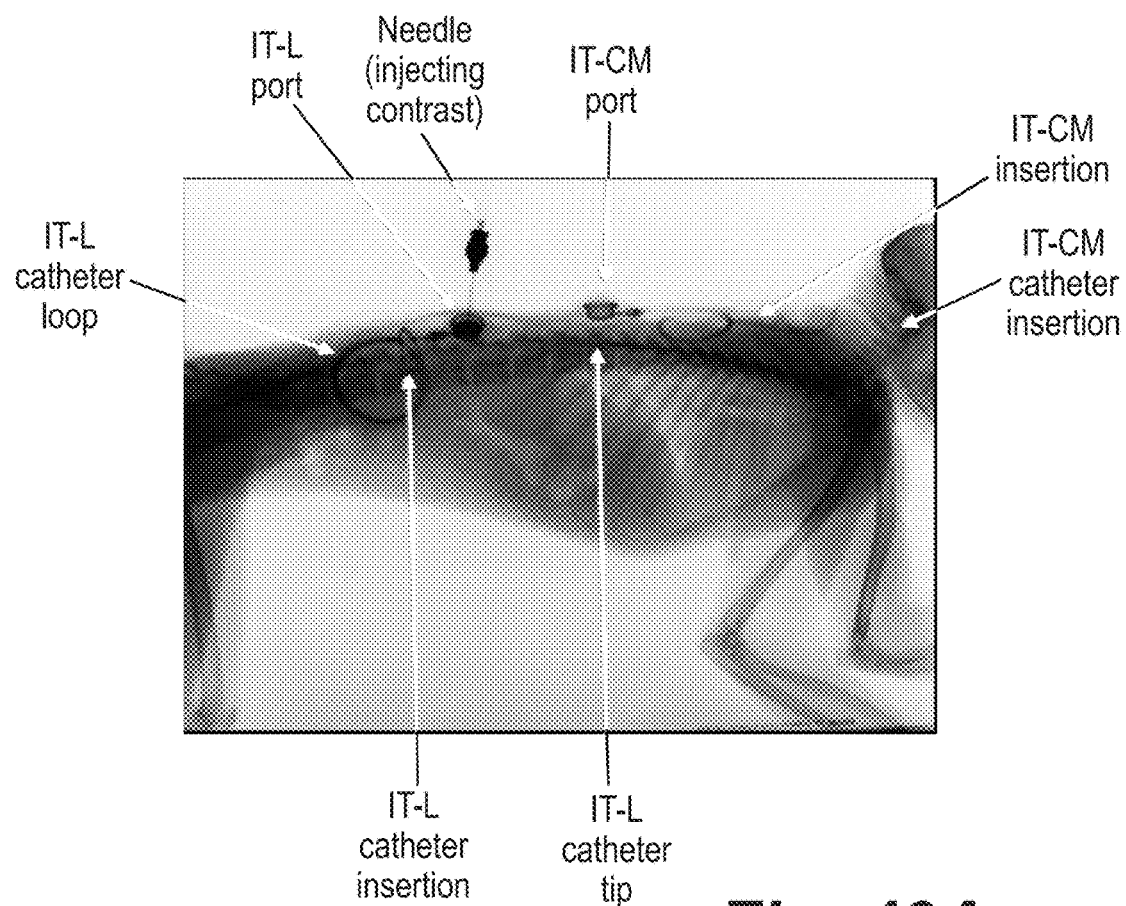
Figure 43B:
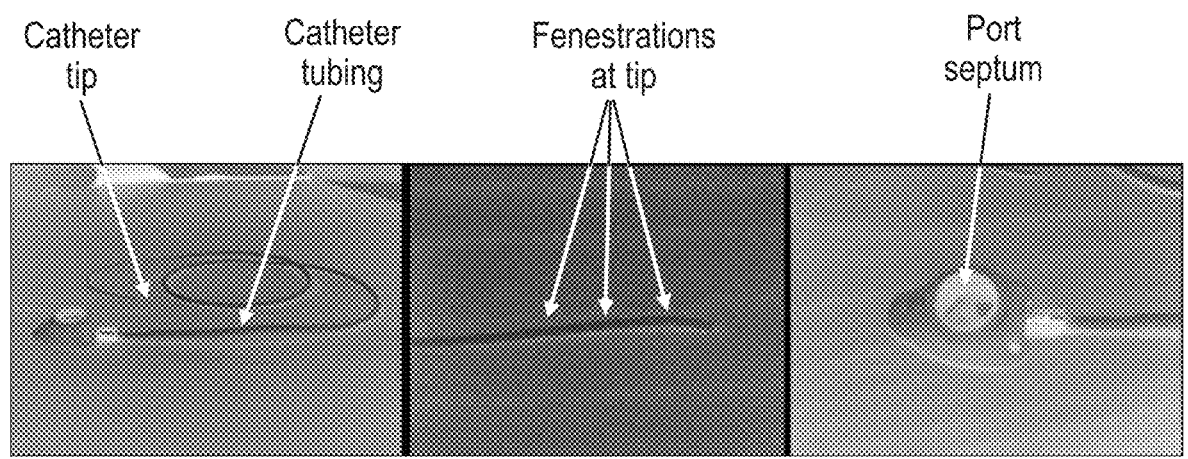
Figure 43C:
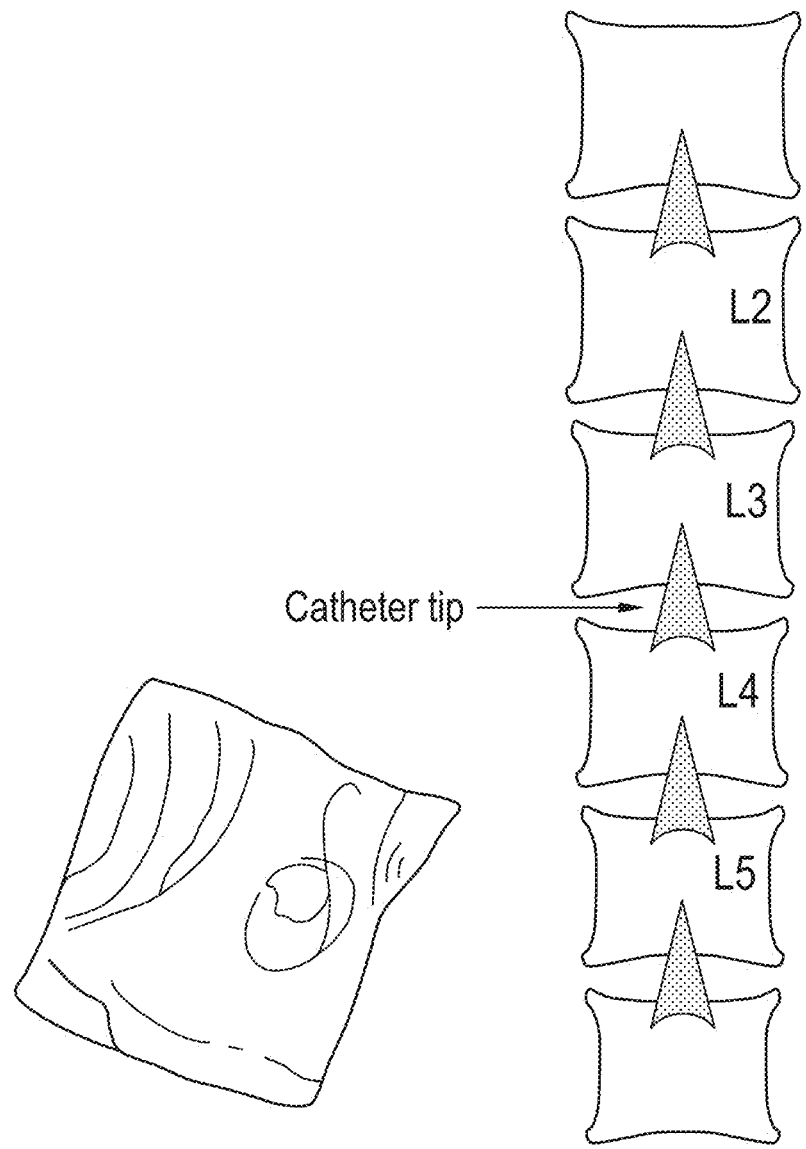

FIGS. 43A, 43B and 43C: FIG. 43A depicts exemplary locations within a patient's body where an IDDD may be placed; FIG. 43B depicts various components of an intrathecal drug delivery device (IDDD); and FIG. 43C depicts an exemplary insertion location within a patient's body for IT-lumbar injection.

DEFINITIONS

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition (e.g., Sanfilippo B syndrome). In some embodiments, amelioration includes increasing levels of relevant protein or its activity (e.g., Naglu) that is deficient in relevant disease tissues.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Cation-independent mannose-6-phosphate receptor (CI-MPR): As used herein, the term "cation-independent mannose-6-phosphate receptor (CI-MPR)" refers to a cellular receptor that binds mannose-6-phosphate (M6P) tags on acid hydrolase precursors in the Golgi apparatus that are destined for transport to the lysosome. In addition to mannose-6-phosphates, the CI-MPR also binds other proteins including IGF-II. The CI-MPR is also known as "M6P/IGF-II receptor," "CI-MPR/IGF-II receptor," "IGF-II receptor" or "IGF2 Receptor." These terms and abbreviations thereof are used interchangeably herein.

Concurrent immunosuppressant therapy: As used herein, the term "concurrent immunosuppressant therapy" includes any immunosuppressant therapy used as pre-treatment, preconditioning or in parallel to a treatment method.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic protein for the patient to be treated. Each unit contains a predetermined quantity of active material calculated to produce the desired therapeutic effect. It will be understood, however, that the total dosage of the composition will be decided by the attending physician within the scope of sound medical judgment.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodsteam. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of lysosomal storage disease (e.g., Sanfilippo B syndrome) as the individual being treated, who is about the same age as the individual being treated (to ensure that the stages of the disease in the treated individual and the control individual(s) are comparable).

Individual, subject, patient: As used herein, the terms "subject," "individual" or "patient" refer to a human or a non-human mammalian subject. The individual (also referred to as "patient" or "subject") being treated is an individual (fetus, infant, child, adolescent, or adult human) suffering from a disease, for example, Sanfilippo B syndrome.

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Linker: As used herein, the term "linker" refers to, in a fusion protein, an amino acid sequence other than that appearing at a particular position in the natural protein and is generally designed to be flexible or to interpose a structure, such as an a-helix, between two protein moieties. A linker is also referred to as a spacer.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources.

Lysosomal enzyme deficiency: As used herein, "lysosomal enzyme deficiency" refers to a group of genetic disorders that result from deficiency in at least one of the enzymes that are required to break macromolecules (e.g., enzyme substrates) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases and various examples are described in more detail below.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Replacement enzyme: As used herein, the term "replacement enzyme" refers to any enzyme that can act to replace at least in part the deficient or missing enzyme in a disease to be treated. In some embodiments, the term "replacement enzyme" refers to any enzyme that can act to replace at least in part the deficient or missing lysosomal enzyme in a lysosomal storage disease to be treated. In some embodiments, a replacement enzyme is capable of reducing accumulated materials in mammalian lysosomes or that can rescue or ameliorate one or more lysosomal storage disease symptoms. Replacement enzymes suitable for the invention include both wild-type or modified lysosomal enzymes and can be produced using recombinant and synthetic methods or purified from nature sources. A replacement enzyme can be a recombinant, synthetic, gene-activated or natural enzyme.

Soluble: As used herein, the term "soluble" refers to the ability of a therapeutic agent to form a homogenous solution. In some embodiments, the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, the pharmaceutical compositions are formulated such that calcium salts are excluded from such compositions. In some embodiments, therapeutic agents in accordance with the present invention are soluble in its corresponding pharmaceutical composition. It will be appreciated that, while isotonic solutions are generally preferred for parenterally administered drugs, the use of isotonic solutions may limit adequate solubility for some therapeutic agents and, in particular some proteins and/or enzymes. Slightly hypertonic solutions (e.g., up to 175 mM sodium chloride in 5 mM sodium phosphate at pH 7.0) and sugar-containing solutions (e.g., up to 2% sucrose in 5 mM sodium phosphate at pH 7.0) have been demonstrated to be well tolerated in monkeys. For example, the most common approved CNS bolus formulation composition is saline (150 mM NaCl in water).

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In general, pharmaceutical compositions described herein have been formulated such that they are capable of stabilizing, or alternatively slowing or preventing the degradation, of one or more therapeutic agents formulated therewith (e.g., recombinant proteins). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Subject: As used herein, the term "subject" means any mammal, including humans. In certain embodiments of the present invention the subject is an adult, an adolescent or an infant. Also contemplated by the present invention are the administration of the pharmaceutical compositions and/or performance of the methods of treatment in-utero.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Synthetic CSF: As used herein, the term "synthetic CSF" refers to a solution that has pH, electrolyte composition, glucose content and osmalarity consistent with the cerebrospinal fluid. Synthetic CSF is also referred to as artificial CSF. In some embodiments, synthetic CSF is an Elliott's B solution.

Suitable for CNS delivery: As used herein, the phrase "suitable for CNS delivery" or "suitable for intrathecal delivery" as it relates to the pharmaceutical compositions of the present invention generally refers to the stability, tolerability, and solubility properties of such compositions, as well as the ability of such compositions to deliver an effective amount of the therapeutic agent contained therein to the targeted site of delivery (e.g., the CSF or the brain).

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue an/or a peripheral target tissue. Exemplary target tissues are described in detail below.

Therapeutic moiety: As used herein, the term "therapeutic moiety" refers to a portion of a molecule that renders the therapeutic effect of the molecule. In some embodiments, a therapeutic moiety is a polypeptide having therapeutic activity. For example, a therapeutic moiety according to the present invention can be a polypeptide that can substitute for a natural Naglu protein. In some embodiments, a therapeutic moiety according to the present invention can be a polypeptide that can rescue one or more phenotypes associated with Naglu deficiency. In some embodiments, a therapeutic moiety according to the present invention can treat one or more symptoms in a Sanfilippo B syndrome patient.

Therapeutically effective amount: As used herein, the term "therapeutically effective amount" refers to an amount of a therapeutic protein (e.g., Naglu) which confers a therapeutic effect on the treated subject, at a reasonable benefit/ risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

Tolerable: As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Sanfilippo B syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

DETAILED DESCRIPTION

Among other things, the present invention provides methods and compositions of treating Sanfilippo syndrome type B (Sanfilippo B) by, e.g., intrathecal (IT) administration of a Naglu protein. A suitable Naglu protein can be a recombinant, gene-activated or natural protein. In some embodiments, a suitable Naglu protein is a recombinant Naglu protein. In some embodiments, a recombinant Naglu protein is a fusion protein containing a Naglu domain and a lysosomal targeting moiety. In some embodiments, the lysosomal targeting domain is an IGF-II moiety.

Various aspects of the invention are described in detail in the following sections. The use of sections is not meant to limit the invention. Each section can apply to any aspect of the invention. In this application, the use of "or" means "and/or" unless stated otherwise.

Therapeutic Fusion Proteins

According to the present invention, therapeutic fusion proteins suitable for the treatment of Sanfilippo B disease may include a Naglu domain (also referred to as a therapeutic moiety) and a lysosomal targeting moiety.

Naglu Domain

A suitable Naglu domain according to the present invention can be any molecule or a portion of a molecule that can substitute for naturally-occurring Naglu protein activity or rescue one or more phenotypes or symptoms associated with Naglu-deficiency. In some embodiments, a therapeutic moiety suitable for the invention is a polypeptide having an N-terminus and a C-terminus and an amino acid sequence substantially similar or identical to mature human Naglu protein.

Typically, human Naglu is produced as a precursor molecule that is processed to a mature form. This process generally occurs by removing the 23 amino acid signal peptide as the protein enters the endoplasmic reticulum. Typically, the precursor form is also referred to as full-length precursor or full-length Naglu protein, which contains 743 amino acids. The N-terminal 23 amino acids are cleaved as the precursor protein enters the endoplasmic reticulum, resulting in a mature form. Thus, it is contemplated that the N-terminal 23 amino acids is generally not required for the Naglu protein activity. The amino acid sequences of the mature form (SEQ ID NO:1) and full-length precursor (SEQ ID NO:2) of a typical wild-type or naturally-occurring human Naglu protein are shown in Table 1.

TABLE 1

| | Human Naglu |
|---|---|
| Mature Form | DEAREAAAVRALVARLLGPGPAADFSVSVERALAAKPGLD TYSLGGGGAARVRVRGSTGVAAAAGLHRYLRDFCGCHVAW SGSQLRLPRPLPAVPGELTEATPNRYRYYQNVCTQSYSFV WWDWARWEREIDWMALNGINLALAWSGQEAIWQRVYLALG LTQAEINEFFTGPAFLAWGRMGNLHTWDGPLPPSWHIKQL YLQHRVLDQMRSFGMTPVLPAFAGHVPEAVTRVFPQVNVT KMGSWGHFNCSYSCSFLLAPEDPIFPIIGSLFLRELIKEF GTDHIYGADTFNEMQPPSSEPSYLAAATTAVYEAMTAVDT EAVWLLQGWLFQHQPQFWGPAQIRAVLGAVPRGRLLVLDL FAESQPVYTRTASFQGQPFIWCMLHNFGGNHGLFGALEAV NGGPEAARLFPNSTMVGTGMAPEGISQNEVVYSLMAELGW RKDPVPDLAAWVTSFAARRYGVSHPDAGAAWRLLLRSVYN CSGEACRGHNRSPLVRRPSLQMNTSIWYNRSDVFEAWRLL LTSAPSLATSPAFRYDLLDLTRQAVQELVSLYYEEARSAY LSKELASLLRAGGVLAYELLPALDEVLASDSRFLLGSWLE QARAAAVSEAEADFYEQNSRYQLTLWGPEGNILDYANKQL AGLVANYYTPRWRLFLEALVDSVAQGIPFQQHQFDKNVFQ LEQAFVLSKQRYPSQPRGDTVDLAKKIFLKYYPRWVAGSW (SEQ ID NO: 1) |
| Full-Length Precursor | MEAVAVAAAVGVLLLAGAGGAAGDEAREAAAVRALVARLL GPGPAADFSVSVERALAAKPGLDTYSLGGGGAARVRVRGS TGVAAAAGLHRYLRDFCGCHVAWSGSQLRLPRPLPAVPGE LTEATPNRYRYYQNVCTQSYSFVWWDWARWEREIDWMALN GINLALAWSGQEAIWQRVYLALGLTQAEINEFFTGPAFLA WGRMGNLHTWDGPLPPSWHIKQLYLQHRVLDQMRSFGMTP VLPAFAGHVPEAVTRVFPQVNVTKMGSWGHFNCSYSCSFL LAPEDPIFPIIGSLFLRELIKEFGTDHIYGADTFNEMQPP SSEPSYLAAATTAVYEAMTAVDTEAVWLLQGWLFQHQPQF WGPAQIRAVLGAVPRGRLLVLDLFAESQPVYTRTASFQGQ PFIWCMLHNFGGNHGLFGALEAVNGGPEAARLFPNSTMVG TGMAPEGISQNEVVYSLMAELGWRKDPVPDLAAWVTSFAA |

TABLE 1-continued

Human Naglu

```
RRYGVSHPDAGAAWRLLLRSVYNCSGEACRGHNRSPLVRR
PSLQMNTSIWYNRSDVFEAWRLLLTSAPSLATSPAFRYDL
LDLTRQAVQELVSLYYEEARSAYLSKELASLLRAGGVLAY
ELLPALDEVLASDSRFLLGSWLEQARAAAVSEAEADFYEQ
NSRYQLTLWGPEGNILDYANKQLAGLVANYYTPRWRLFLE
ALVDSVAQGIPFQQHQFDKNVFQLEQAFVLSKQRYPSQPR
GDTVDLAKKIFLKYYPRWVAGSW (SEQ ID NO: 2)
```

Thus, in some embodiments, a therapeutic moiety suitable for the present invention is mature human Naglu protein (SEQ ID NO:1). In some embodiments, a suitable therapeutic moiety may be a homologue or an analogue of mature human Naglu protein. For example, a homologue or an analogue of mature human Naglu protein may be a modified mature human Naglu protein containing one or more amino acid substitutions, deletions, and/or insertions as compared to a wild-type or naturally-occurring Naglu protein (e.g., SEQ ID NO:1), while retaining substantial Naglu protein activity. Thus, in some embodiments, a therapeutic moiety suitable for the present invention is substantially homologous to mature human Naglu protein (SEQ ID NO:1). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a therapeutic moiety suitable for the present invention is substantially identical to mature human Naglu protein (SEQ ID NO:1). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a therapeutic moiety suitable for the present invention contains a fragment or a portion of mature human Naglu protein.

Alternatively, a therapeutic moiety suitable for the present invention is full-length Naglu protein. In some embodiments, a suitable therapeutic moiety may be a homologue or an analogue of full-length human Naglu protein. For example, a homologue or an analogue of full-length human Naglu protein may be a modified full-length human Naglu protein containing one or more amino acid substitutions, deletions, and/or insertions as compared to a wild-type or naturally-occurring full-length Naglu protein (e.g., SEQ ID NO:2), while retaining substantial Naglu protein activity. Thus, In some embodiments, a therapeutic moiety suitable for the present invention is substantially homologous to full-length human Naglu protein (SEQ ID NO:2). In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a therapeutic moiety suitable for the present invention is substantially identical to SEQ ID NO:2. In some embodiments, a therapeutic moiety suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a therapeutic moiety suitable for the present invention contains a fragment or a portion of full-length human Naglu protein. As used herein, a full-length Naglu protein typically contains signal peptide sequence.

In some embodiments, a therapeutic protein includes a targeting moiety (e.g., a lysosome targeting sequence) and/or a membrane-penetrating peptide. In some embodiments, a targeting sequence and/or a membrane-penetrating peptide is an intrinsic part of the therapeutic moiety (e.g., via a chemical linkage, via a fusion protein). In some embodiments, a targeting sequence contains a mannose-6-phosphate moiety. In some embodiments, a targeting sequence contains an IGF-I moiety. In some embodiments, a targeting sequence contains an IGF-II moiety.

Lysosomal Targeting Domain

In some embodiments, a therapeutic domain (i.e., a Naglu domain) is modified to facilitate lysosomal targeting. For example, a suitable Naglu domain may be fused to a lysosomal targeting moiety, which may target the Naglu domain to lysosomes in a mannose-6-phosphate-independent manner. Suitable lysosomal targeting domains may be derived from peptides including, but not limited to, IGF-II, IGF-I, Kif, ApoE, TAT, RAP, and p97 peptide. In some embodiments, a lysosomal targeting moiety is a protein, peptide, or other moiety that binds the CI-MPR, which is also referred to as IGF-II receptor, in a mannose-6-phosphate-independent manner.

In some embodiments, a lysosomal targeting moiety is derived from human insulin-like growth factor II (IGF-II). In some embodiments, a GILT tag is a wild-type or naturally-occurring mature human IGF-II (SEQ ID NO:3).

Mature human IGF-II
(SEQ ID NO: 3)
```
AYRPSETLCGGELVDTLQFVCGDRGFYFSRPASRVSRRSRGIVEECCFRS

CDLALLETYCATPAKSE
```

In some embodiments, a lysosomal targeting moiety is a modified mature human IGF-II containing amino acid substitutions, insertions or deletions. In some embodiments, a GILT tag has a sequence at least 50%, 55%, 60%, 65%, 70%, 75%, 80%, 85%, 90%, 95%, 98%, or 99% identical to the sequence of mature human IGF-II (SEQ ID NO:3). In some embodiments, a lysosomal targeting moiety is a fragment of mature human IGF-II. In particular embodiments, a lysosomal targeting moiety contains amino acids 8-67 of mature human IGF-II (SEQ ID NO:3). In some embodiments, a lysosomal targeting moiety contains a N-terminal, C-terminal or internal deletion. For example, a lysosomal targeting moiety contains a deletion of amino acids at the N-terminus (e.g., 42-7) of mature human IGF-II (SEQ ID NO:3). In some embodiments, a lysosomal targeting moiety is a modified human IGF-II peptide that has diminished binding affinity for other receptors, such as the IGF-I receptor, as compared to the naturally-occurring human IGF-II.

Various additional lysosomal targeting moieties are known in the art and can be used to practice the present invention. For example, certain peptide-based lysosomal targeting moieties are described in U.S. Pat. Nos. 7,396,811, 7,560,424, and 7,629,309; U.S. Application Publication Nos. 2003-0082176, 2004-0006008, 2003-0072761, 20040005309, 2005-0281805, 2005-0244400, and international publications WO 03/032913, WO 03/032727, WO 02/087510, WO 03/102583, WO 2005/078077, WO/2009/137721, the entire disclosures of which are incorporated herein by reference.

Linker or Spacer

A lysosomal targeting moiety can be fused to the N-terminus or C-terminus of a polypeptide encoding a lysosomal enzyme, or inserted internally. The lysosomal targeting moiety can be fused directly to the lysosomal enzyme polypeptide or can be separated from the lysosomal enzyme polypeptide by a linker or a spacer. An amino acid linker or spacer is generally designed to be flexible or to interpose a structure, such as an alpha-helix, between the two protein moieties. A linker or spacer can be relatively short, such as the sequence GGGGGAAAAGGGG (SEQ ID NO:4), GAP, GGGGGP (SEQ ID NO:7), or can be longer, such as, for example, 10-50 (e.g., 10-20, 10-25, 10-30, 10-35, 10-40, 10-45, 10-50) amino acids in length. In some embodiments, various short linker sequences can be present in tandem repeats. For example, a suitable linker may contain the amino acid sequence of GGGGGAAAAGGGG (SEQ ID NO:4) present in tandem repeats. In some embodiments, such as linker may further contain one or more GAP sequences, that frames the sequence of GGGG-GAAAAGGGG (SEQ ID NO:4). For example, a suitable linker may contain amino acid sequence of GAPGGGG-GAAAAGGGGGAPGGGGGAAAAGGGGGAPGGGG-GAAAAGGGGGAP (SEQ ID NO:5).

In some embodiments, a suitable linker or spacer may contain a sequence at least 50%, 55%, 60%, 65%, 70%, 75%, 80%, 85%, 90%, 95%, 98%, or 99% identical to the sequence of SEQ ID NO:5.

In some embodiments, a therapeutic protein suitable for the present invention may contain M6P residues. In some embodiments, a therapeutic protein suitable for the present invention may contain a bis-phosphorylated oligosaccharides which have higher binding affinity to the CI-MPR. In some embodiments, a suitable enzyme contains up to about an average of about at least 20% bis-phosphorylated oligosaccharides per enzyme. In other embodiments, a suitable enzyme may contain about 10%, 15%, 18%, 20%, 25%, 30%, 35%, 40%, 45%, 50%, 55%, 60% bis-phosphorylated oligosaccharides per enzyme. While such bis-phosphorylated oligosaccharides may be naturally present on the enzyme, it should be noted that the enzymes may be modified to possess such oligosaccharides. For example, suitable replacement enzymes may be modified by certain enzymes which are capable of catalyzing the transfer of N-acetylglucosamine-L-phosphate from UDP-GlcNAc to the 6' position of α-1,2-linked mannoses on lysosomal enzymes. Methods and compositions for producing and using such enzymes are described by, for example, Canfield et al. in U.S. Pat. Nos. 6,537,785, and 6,534,300, each incorporated herein by reference.

In some embodiments, a therapeutic protein suitable for the present invention is underglycosylated. As used herein, "underglycosylated" refers to a protein or enzyme in which one or more carbohydrate structures (e.g., M6P residues) that would normally be present on a naturally-occurring enzyme has been omitted, removed, modified, or masked. Underglycosylated lysosomal enzymes may be produced in a host (e.g. bacteria or yeast) that does not glycosylate proteins as conventional mammalian cells (e.g. Chinese hamster ovary (CHO) cells) do. For example, proteins produced by the host cell may lack terminal mannose, fucose, and/or N-acetylglucosamine residues, which are recognized by the mannose receptor, or may be completely unglycosylated. In some embodiments, underglycosylated lysosomal enzymes may be produced in mammalian cells or in other hosts, but treated chemically or enzymatically to remove one or more carbohydrate residues (e.g. one or more M6P residues) or to modify or mask one or more carbohydrate residues. Such chemically or enzymatically treated enzymes are also referred to as deglycosylated lysosomal enzymes. In some embodiments, one or more potential glycosylation sites are removed by mutation of the nucleic acid encoding a lysosomal enzyme, thereby reducing glycosylation of the enzyme when synthesized in a mammalian cell or other cell that glycosylates proteins. In some embodiments, lysosomal enzymes can be produced using a secretory signal peptide (e.g., an IGF-II signal peptide) such that the glycosylation levels of the enzymes are reduced and/or modified. Examples of underglycosylated or deglycosylated lysosomal enzymes are described in U.S. Pat. No. 7,629,309 and U.S. Publication Nos. 20090041741 and 20040248262, the disclosures of all of which are hereby incorporated by reference.

Protein Production

Therapeutic proteins suitable for the present invention can be produced in any mammalian cells or cell types susceptible to cell culture, and to expression of polypeptides, such as, for example, human embryonic kidney (HEK) 293, Chinese hamster ovary (CHO), monkey kidney (COS), HT1080, C10, HeLa, baby hamster kidney (BHK), 3T3, C127, CV-1, HaK, NS/O, and L-929 cells. Specific non-limiting examples include, but are not limited to, BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells +/−DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.*, 383:44-68 (1982)); MRC 5 cells; FS4 cells; and a human hepatoma line (Hep G2). In some embodiments, enzymes are produced in CHO cells. In some embodiments, enzymes are produced in CHO-derived cells such as endosomal acidification-deficient cell lines (e.g., CHO-K derived END3 complementation group).

Enzymes can also be expressed in a variety of non-mammalian host cells such as, for example, insect (e.g., Sf-9, Sf-21, Hi5), plant (e.g., Leguminosa, cereal, or tobacco), yeast (e.g., *S. cerivisae, P. pastoris*), prokaryote (e.g., *E. Coli, B. subtilis* and other *Bacillus* spp., *Pseudomonas* spp., *Streptomyces* spp), or fungus.

In other embodiments, transgenic nonhuman mammals have been shown to produce lysosomal enzymes in their milk. Such transgenic nonhuman mammals may include mice, rabbits, goats, sheep, porcines or bovines. See U.S. Pat. Nos. 6,118,045 and 7,351,410, each of which are hereby incorporated by reference in their entirety.

Intrathecal Delivery

According to the present invention, a therapeutic protein, i.e., a replacement enzyme, containing a Naglu domain is delivered to the CNS. Various techniques and routes can be used for CNS delivery including, but not limited to, intraparenchymal, intracerebral, intraventricular cerebral (ICV), intrathecal (e.g., IT-Lumbar, IT-cisterna magna) administrations and any other techniques and routes for injection directly or indirectly to the CNS and/or CSF.

In some embodiments, a replacement enzyme is delivered to the CNS by administering into the cerebrospinal fluid (CSF) of a subject in need of treatment. In some embodiments, intrathecal administration is used to deliver a desired replacement enzyme into the CSF. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al. Advances in Drug Delivery Systems and Applications in Neurosurgery, 143-192 and Omaya et al., Cancer Drug Delivery, 1: 169-179, the contents of which are incorporated herein by reference.

According to the present invention, an enzyme may be injected at any region surrounding the spinal canal. In some embodiments, an enzyme is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumber area is also referred to as "lumbar IT delivery" or "lumbar IT administration." The term "cisterna magna" refers to the space around and below the cerebellum via the opening between the skull and the top of the spine. Typically, intrathecal injection via cisterna magna is also referred to as "cisterna magna delivery." The term "cerebral ventricle" refers to the cavities in the brain that are continuous with the central canal of the spinal cord. Typically, injections via the cerebral ventricle cavities are referred to as intravetricular Cerebral (ICV) delivery.

In some embodiments, "intrathecal administration" or "intrathecal delivery" according to the present invention refers to lumbar IT administration or delivery, for example, delivered between the third and fourth lumbar (lower back) vertebrae and, more inclusively, the L2-S1 region of the spine. It is contemplated that lumbar IT administration or delivery distinguishes over cisterna magna delivery in that lumbar IT administration or delivery according to our invention provides better and more effective delivery to the distal spinal canal, while cisterna magna delivery, among other things, typically does not deliver well to the distal spinal canal.

Stable Formulations for IT Delivery

In some embodiments, desired enzymes are delivered in stable formulations for intrathecal delivery. Certain embodiments of the invention are based, at least in part, on the discovery that various formulations disclosed herein facilitate the effective delivery and distribution of one or more therapeutic agents (e.g., enzymes) to targeted tissues, cells and/or organelles of the CNS. Among other things, formulations described herein are capable of solubilizing high concentrations of therapeutic agents (e.g., proteins or enzymes) and are suitable for the delivery of such therapeutic agents to the CNS of subjects for the treatment of diseases having a CNS component and/or etiology. The compositions described herein are further characterized by improved stability and improved tolerability when administered to the CNS of a subject (e.g., intrathecally) in need thereof.

Before the present invention, traditional unbuffered isotonic saline and Elliott's B solution, which is artificial CSF, were typically used for intrathecal delivery. A comparison depicting the compositions of CSF relative to Elliott's B solution is included in Table 2 below. As shown in Table 2, the concentration of Elliot's B Solution closely parallels that of the CSF. Elliott's B Solution, however contains a very low buffer concentration and accordingly may not provide the adequate buffering capacity needed to stabilize therapeutic agents (e.g., proteins), especially over extended periods of time (e.g., during storage conditions). Furthermore, Elliott's B Solution contains certain salts which may be incompatible with the formulations intended to deliver some therapeutic agents, and in particular proteins or enzymes. For example, the calcium salts present in Elliott's B Solution are capable of mediating protein precipitation and thereby reducing the stability of the formulation.

TABLE 2

| Solution | $Na^+$ mEq/L | $K^+$ mEq/L | $Ca^{++}$ mEq/L | $Mg^{++}$ mEq/L | $HCO3^-$ mEq/L | $Cl^-$ mEq/L | pH | Phosphorous mg/L | Glucose mg/L |
|---|---|---|---|---|---|---|---|---|---|
| CSF | 117-137 | 2.3 | 2.2 | 2.2 | 22.9 | 113-127 | 7.31 | 1.2-2.1 | 45-80 |
| Elliott's B Sol'n | 149 | 2.6 | 2.7 | 2.4 | 22.6 | 132 | 6.0-7.5 | 2.3 | 80 |

Thus, in some embodiments, formulations suitable for intrathecal delivery according to the present invention are not synthetic or artificial CSF.

In some embodiments, formulations for intrathecal delivery have been formulated such that they are capable of stabilizing, or alternatively slowing or preventing the degradation, of one or more therapeutic agents formulated therewith (e.g., recombinant proteins). As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., preferably for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Stability of the therapeutic agent is of particular importance. Stability of the therapeutic agent may be further assessed relative to the biological activity or physiochemical integrity of the therapeutic agent over extended periods of time. For example, stability at a given time point may be compared against stability at an earlier time point (e.g., upon formulation day 0) or against unformulated therapeutic agent and the results of this comparison expressed as a percentage. Preferably, the pharmaceutical compositions of the present invention maintain at least 100%, at least 99%, at least 98%, at least 97% at least 95%, at least 90%, at least 85%, at least 80%, at least 75%, at least 70%, at least 65%, at least 60%, at least 55% or at least 50% of the therapeutic agent's biological activity or physiochemical integrity over an extended period of time (e.g., as measured over at least about 6-12 months, at room temperature or under accelerated storage conditions).

In some embodiments, therapeutic agents (e.g., desired enzymes) are soluble in formulations of the present invention. The term "soluble" as it relates to the therapeutic agents of the present invention refer to the ability of such therapeutic agents to form a homogenous solution. Preferably the solubility of the therapeutic agent in the solution into which it is administered and by which it is transported to the target site of action (e.g., the cells and tissues of the brain) is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts.) In some embodiments, the pharmaceutical compositions are formulated such that calcium salts are excluded from such compositions.

Thus, suitable formulations for intrathecal administration may contain a therapeutic agent (e.g., enzyme) of interest at various concentrations. In some embodiments, suitable formulations may contain a protein or enzyme of interest at a concentration up to about 300 mg/ml (e.g., up to about 250 mg/ml, up to 200 mg/ml, up to 150 mg/ml, up to 100 mg/ml, up to 90 mg/ml, up to 80 mg/ml, up to 70 mg/ml, up to 60 mg/ml, up to 50 mg/ml, up to 40 mg/ml, up to 30 mg/ml, up to 25 mg/ml, up to 20 mg/ml, up to 10 mg/ml). In some embodiments, suitable formulations may contain a protein or enzyme of interest at a concentration ranging between about 0-300 mg/ml (e.g., about 1-250 mg/ml, about 1-200 mg/ml, about 1-150 mg/ml, about 1-100 mg/ml, about 10-100 mg/ml, about 10-80 mg/ml, about 10-70 mg/ml, about 1-60 mg/ml, about 1-50 mg/ml, about 10-150 mg/ml, about 1-30 mg/ml). In some embodiments, formulations suitable for intrathecal delivery may contain a protein of interest at a concentration of approximately 1 mg/ml, 3 mg/ml, 5 mg/ml, 10 mg/ml, 15 mg/ml, 20 mg/ml, 25 mg/ml, 50 mg/ml, 75 mg/ml, 100 mg/ml, 150 mg/ml, 200 mg/ml, 250 mg/ml or 300 mg/ml.

In some embodiments, isotonic solutions are used. In some embodiments, slightly hypertonic solutions (e.g., up to 300 mM (e.g., up to 250 mM, 200 mM, 175 mM, 150 mM, 125 mM) sodium chloride in 5 mM sodium phosphate at pH 7.0) and sugar-containing solutions (e.g., up to 3% (e.g., up to 2.4%, 2.0%, 1.5%, 1.0%) sucrose in 5 mM sodium phosphate at pH 7.0) have been demonstrated to be well tolerated in monkeys. In some embodiments, a suitable CNS bolus formulation composition is saline (e.g., 150 mM NaCl in water).

Many therapeutic agents, and in particular the proteins and enzymes of the present invention, require controlled pH and specific excipients to maintain their solubility and stability in the pharmaceutical compositions of the present invention. Table 3 below identifies certain exemplary aspects of protein formulations considered to be important for maintaining the solubility and stability of the protein therapeutic agents of the present invention.

TABLE 3

| Parameter | Typical Range/Type | Rationale |
| --- | --- | --- |
| pH | 5 to 7.5 | For stability |
| | | Sometimes also for solubility |
| Buffer type | acetate, succinate, citrate, histidine, phosphate or Tris | To maintain optimal pH May also affect stability |

TABLE 3-continued

| Parameter | Typical Range/Type | Rationale |
| --- | --- | --- |
| Buffer concentration | 5-50 mM | To maintain pH May also stabilize or add ionic strength |
| Tonicifier | NaCl, sugars, mannitol | To render iso-osmotic or isotonic solutions |
| Surfactant | Polysorbate 20, polysorbate 80 | To stabilize against interfaces and shear |
| Other | Amino acids (e.g. arginine) at tens to hundreds of mM | For enhanced solubility or stability |

The pH of the pharmaceutical composition is an additional factor which is capable of altering the solubility of a therapeutic agent (e.g., an enzyme or protein) in an aqueous pharmaceutical composition. In some embodiments, pharmaceutical compositions of the present invention contain one or more buffers. In some embodiments, compositions according to the invention contain an amount of buffer sufficient to maintain the optimal pH of said composition between about 4.0-8.0, between about 5.0-7.5, between about 5.5-7.0, between about 6.0-7.0 and between about 6.0-7.5. In other embodiments, the buffer comprises up to about 50 mM (e.g., up to about 45 mM, 40 mM, 35 mM, 30 mM, 25 mM, 20 mM, 15 mM, 10 mM, 5 mM) of sodium phosphate. Suitable buffers include, for example acetate, succinate, citrate, phosphate, other organic acids and tris (hydroxymethyl)aminomethane ("Tris"). Suitable buffer concentrations can be from about 1 mM to about 100 mM, or from about 3 mM to about 20 mM, depending, for example, on the buffer and the desired isotonicity of the formulation. In some embodiments, a suitable buffering agent is present at a concentration of approximately 1 mM, 5 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, or 100 mM.

In some embodiments, formulations contain an isotonicity agent to keep the formulations isotonic. As used in connection with IT delivery, by "isotonic" is meant that the formulation of interest has essentially the same osmolarity as human CSF. Isotonic formulations will generally have an osmolarity from about 240 mOsm/kg to about 350 mOsm/kg. Isotonicity can be measured using, for example, a vapor pressure or freezing point type osmometers. Exemplary isotonicity agents include, but are not limited to, glycine, sorbitol, mannitol, sodium chloride and arginine. In some embodiments, suitable isotonic agents may be present in formulations at a concentration from about 0.01-5% (e.g., 0.05, 0.1, 0.15, 0.2, 0.3, 0.4, 0.5, 0.75, 1.0, 1.25, 1.5, 2.0, 2.5, 3.0, 4.0 or 5.0%) by weight.

In some embodiments, formulations may contain a stabilizing agent to protect the protein. Typically, a suitable stabilizing agent is a non-reducing sugar such as sucrose, raffinose, trehalose, or amino acids such as glycine, arginine and methionine. The amount of stabilizing agent in a formulation is generally such that the formulation will be isotonic. However, hypertonic formulations may also be suitable. In addition, the amount of stabilizing agent must not be too low such that an unacceptable amount of degradation/aggregation of the therapeutic agent occurs. Exemplary stabilizing agent concentrations in the formulation may range from about 1 mM to about 400 mM (e.g., from about 30 mM to about 300 mM, and from about 50 mM to about 100 mM), or alternatively, from 0.1% to 15% (e.g., from 1% to 10%, from 5% to 15%, from 5% to 10%) by weight. In some embodiments, the ratio of the mass amount of the stabilizing agent and the therapeutic agent is about 1:1. In other embodiments, the ratio of the mass amount of the stabilizing agent and the therapeutic agent can be about 0.1:1, 0.2:1, 0.25:1, 0.4:1, 0.5:1, 1:1, 2:1, 2.6:1, 3:1, 4:1, 5:1, 10:1, or 20:1. In some embodiments, suitable for lyophilization, the stabilizing agent is also a lyoprotectants.

The pharmaceutical compositions, formulations and related methods of the invention are useful for delivering a variety of therapeutic agents to the CNS of a subject (e.g., intrathecally, intraventricularly or intracisternally) and for the treatment of the associated diseases. The pharmaceutical compositions of the present invention are particularly useful for delivering proteins and enzymes to subjects suffering from lysosomal storage disorders.

In some embodiments, it is desirable to add a surfactant to formulations. Exemplary surfactants include nonionic surfactants such as Polysorbates (e.g., Polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristarnidopropyl-, palmidopropyl-, or isostearamidopropyl-dimethylamine; sodium methyl cocoyl-, or disodium methyl ofeyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68, etc). Typically, the amount of surfactant added is such that it reduces aggregation of the protein and minimizes the formation of particulates or effervescences. For example, a surfactant may be present in a formulation at a concentration from about 0.001-0.5% (e.g., about 0.005-0.05%, or 0.005-0.01%). In particular, a surfactant may be present in a formulation at a concentration of approximately 0.005%, 0.01%, 0.02%, 0.1%, 0.2%, 0.3%, 0.4%, or 0.5%, etc.

In some embodiments, suitable formulations may further include one or more bulking agents, in particular, for lyophilized formulations. A "bulking agent" is a compound which adds mass to the lyophilized mixture and contributes to the physical structure of the lyophilized cake. For example, a bulking agent may improve the appearance of lyophilized cake (e.g., essentially uniform lyophilized cake). Suitable bulking agents include, but are not limited to, sodium chloride, lactose, mannitol, glycine, sucrose, trehalose, hydroxyethyl starch. Exemplary concentrations of bulking agents are from about 1% to about 10% (e.g., 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, and 10.0%).

Formulations in accordance with the present invention can be assessed based on product quality analysis, reconstitution time (if lyophilized), quality of reconstitution (if lyophilized), high molecular weight, moisture, and glass transition temperature. Typically, protein quality and product analysis include product degradation rate analysis using methods including, but not limited to, size exclusion HPLC (SE-HPLC), cation exchange-HPLC (CEX-HPLC), X-ray diffraction (XRD), modulated differential scanning calorimetry (mDSC), reversed phase HPLC (RP-HPLC), multi-angle light scattering (MALS), fluorescence, ultraviolet absorption, nephelometry, capillary electrophoresis (CE), SDS-PAGE, and combinations thereof. In some embodiments, evaluation of product in accordance with the present invention may include a step of evaluating appearance (either liquid or cake appearance).

Generally, formulations (lyophilized or aqueous) can be stored for extended periods of time at room temperature. Storage temperature may typically range from 0° C. to 45° C. (e.g., 4° C., 20° C., 25° C., 45° C. etc.). Formulations may be stored for a period of months to a period of years. Storage time generally will be 24 months, 12 months, 6 months, 4.5 months, 3 months, 2 months or 1 month. Formulations can be stored directly in the container used for administration, eliminating transfer steps.

Formulations can be stored directly in the lyophilization container (if lyophilized), which may also function as the reconstitution vessel, eliminating transfer steps. Alternatively, lyophilized product formulations may be measured into smaller increments for storage. Storage should generally avoid circumstances that lead to degradation of the proteins, including but not limited to exposure to sunlight, UV radiation, other forms of electromagnetic radiation, excessive heat or cold, rapid thermal shock, and mechanical shock.

In some embodiments, formulations according to the present invention are in a liquid or aqueous form. In some embodiments, formulations of the present invention are lyophilized Such lyophilized formulations may be reconstituted by adding one or more diluents thereto prior to administration to a subject. Suitable diluents include, but are not limited to, sterile water, bacteriostatic water for injection and sterile saline solution. Preferably, upon reconstitution, the therapeutic agent contained therein is stable, soluble and demonstrates tolerability upon administration to a subject The pharmaceutical compositions of the present invention are characterized by their tolerability. As used herein, the terms "tolerable" and "tolerability" refer to the ability of the pharmaceutical compositions of the present invention to not elicit an adverse reaction in the subject to whom such composition is administered, or alternatively not to elicit a serious adverse reaction in the subject to whom such composition is administered. In some embodiments, the pharmaceutical compositions of the present invention are well tolerated by the subject to whom such compositions is administered.

Device for Intrathecal Delivery

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. As a non-limiting example shown in FIG. 42, a suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4) (FIG. 43A-C).

Relative to intravenous administration, a single dose volume suitable for intrathecal administration is typically small. Typically, intrathecal delivery according to the present invention maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before IT administration. In those cases, a suitable single dose volume may be e.g., more than about 3 ml, 4 ml, 5 ml, 6 ml, 7 ml, 8 ml, 9 ml, 10 ml, 15 ml, or 20 ml.

Various other devices may be used to effect intrathecal administration of a therapeutic composition. For example, formulations containing desired enzymes may be given using an Ommaya reservoir which is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver the particular enzyme being replaced, which is injected into the reservoir. Other devices for intrathecal administration of therapeutic compositions or formulations to an individual are described in U.S. Pat. No. 6,217,552, incorporated herein by reference. Alternatively, the drug may be intrathecally given, for example, by a single injection, or continuous infusion. It should be understood that the dosage treatment may be in the form of a single dose administration or multiple doses.

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In one embodiment of the invention, the enzyme is administered by lateral cerebro ventricular injection into the brain of a subject. The injection can be made, for example, through a burr hole made in the subject's skull. In another embodiment, the enzyme and/or other pharmaceutical formulation is administered through a surgically inserted shunt into the cerebral ventricle of a subject. For example, the injection can be made into the lateral ventricles, which are larger. In some embodiments, injection into the third and fourth smaller ventricles can also be made.

In yet another embodiment, the pharmaceutical compositions used in the present invention are administered by injection into the cisterna magna, or lumbar area of a subject.

In another embodiment of the method of the invention, the pharmaceutically acceptable formulation provides sustained delivery, e.g., "slow release" of the enzyme or other pharmaceutical composition used in the present invention, to a subject for at least one, two, three, four weeks or longer periods of time after the pharmaceutically acceptable formulation is administered to the subject.

As used herein, the term "sustained delivery" refers to continual delivery of a pharmaceutical formulation of the invention in vivo over a period of time following administration, preferably at least several days, a week or several weeks. Sustained delivery of the composition can be demonstrated by, for example, the continued therapeutic effect of the enzyme over time (e.g., sustained delivery of the enzyme can be demonstrated by continued reduced amount of storage granules in the subject). Alternatively, sustained delivery of the enzyme may be demonstrated by detecting the presence of the enzyme in vivo over time.

Delivery to Target Tissues

As discussed above, one of the surprising and important features of the present invention is that therapeutic agents, in particular, replacement enzymes (e.g., a Naglu fusion protein) administered using inventive methods and compositions of the present invention are able to effectively and extensively diffuse across the brain surface and penetrate various layers or regions of the brain, including deep brain regions. In addition, inventive methods and compositions of the present invention effectively deliver replacement enzymes (e.g., a Naglu fusion protein) to various tissues, neurons or cells of spinal cord, including the lumbar region, which is hard to target by existing CNS delivery methods such as ICV injection. Furthermore, inventive methods and compositions of the present invention deliver sufficient amount of replacement enzymes (e.g., a Naglu fusion protein) to blood stream and various peripheral organs and tissues.

Thus, in some embodiments, a replacement enzymes (e.g., a Naglu fusion protein) is delivered to the central nervous system of a subject. In some embodiments, replacement enzymes (e.g., a Naglu fusion protein) is delivered to one or more of target tissues of brain, spinal cord, and/or peripheral organs. As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Brain Target Tissues

In general, the brain can be divided into different regions, layers and tissues. For example, meningeal tissue is a system of membranes which envelops the central nervous system, including the brain. The meninges contain three layers, including dura matter, arachnoid matter, and pia matter. In general, the primary function of the meninges and of the cerebrospinal fluid is to protect the central nervous system. In some embodiments, a therapeutic protein in accordance with the present invention is delivered to one or more layers of the meninges.

The brain has three primary subdivisions, including the cerebrum, cerebellum, and brain stem. The cerebral hemispheres, which are situated above most other brain structures and are covered with a cortical layer. Underneath the cerebrum lies the brainstem, which resembles a stalk on which the cerebrum is attached. At the rear of the brain, beneath the cerebrum and behind the brainstem, is the cerebellum.

The diencephalon, which is located near the midline of the brain and above the mesencephalon, contains the thalamus, metathalamus, hypothalamus, epithalamus, prethalamus, and pretectum. The mesencephalon, also called the midbrain, contains the tectum, tegumentum, ventricular mesocoelia, and cerebral peduncels, the red nucleus, and the cranial nerve III nucleus. The mesencephalon is associated with vision, hearing, motor control, sleep/wake, alertness, and temperature regulation.

Regions of tissues of the central nervous system, including the brain, can be characterized based on the depth of the tissues. For example, CNS (e.g., brain) tissues can be characterized as surface or shallow tissues, mid-depth tissues, and/or deep tissues.

According to the present invention, a therapeutic protein (e.g., a replacement enzyme) may be delivered to any appropriate brain target tissue(s) associated with a particular disease to be treated in a subject. In some embodiments, a therapeutic protein (e.g., a replacement enzyme) in accordance with the present invention is delivered to surface or shallow brain target tissue. In some embodiments, a therapeutic protein in accordance with the present invention is delivered to mid-depth brain target tissue. In some embodiments, a therapeutic protein in accordance with the present invention is delivered to deep brain target tissue. In some embodiments, a therapeutic protein in accordance with the present invention is delivered to a combination of surface or shallow brain target tissue, mid-depth brain target tissue, and/or deep brain target tissue. In some embodiments, a therapeutic protein in accordance with the present invention is delivered to a deep brain tissue at least 4 mm, 5 mm, 6 mm, 7 mm, 8 mm, 9 mm, 10 mm or more below (or internal to) the external surface of the brain.

In some embodiments, replacement enzymes (e.g., a Naglu fusion protein) are delivered to one or more surface or shallow tissues of cerebrum. In some embodiments, the targeted surface or shallow tissues of the cerebrum are located within 4 mm from the surface of the cerebrum. In some embodiments, the targeted surface or shallow tissues of the cerebrum are selected from pia mater tissues, cerebral cortical ribbon tissues, hippocampus, Virchow Robin space, blood vessels within the VR space, the hippocampus, portions of the hypothalamus on the inferior surface of the brain, the optic nerves and tracts, the olfactory bulb and projections, and combinations thereof.

In some embodiments, replacement enzymes (e.g., a Naglu fusion protein) are delivered to one or more deep tissues of the cerebrum. In some embodiments, the targeted surface or shallow tissues of the cerebrum are located 4 mm (e.g., 5 mm, 6 mm, 7 mm, 8 mm, 9 mm, or 10 mm) below (or internal to) the surface of the cerebrum. In some embodiments, targeted deep tissues of the cerebrum include the cerebral cortical ribbon. In some embodiments, targeted deep tissues of the cerebrum include one or more of the diencephalon (e.g., the hypothalamus, thalamus, prethalamus, subthalamus, etc.), metencephalon, lentiform nuclei, the basal ganglia, caudate, putamen, amygdala, globus pallidus, and combinations thereof.

In some embodiments, replacement enzymes (e.g., a Naglu fusion protein) are delivered to one or more tissues of the cerebellum. In certain embodiments, the targeted one or more tissues of the cerebellum are selected from the group consisting of tissues of the molecular layer, tissues of the Purkinje cell layer, tissues of the Granular cell layer, cerebellar peduncles, and combination thereof. In some embodiments, therapeutic agents (e.g., enzymes) are delivered to one or more deep tissues of the cerebellum including, but not limited to, tissues of the Purkinje cell layer, tissues of the Granular cell layer, deep cerebellar white matter tissue (e.g., deep relative to the Granular cell layer), and deep cerebellar nuclei tissue.

In some embodiments, replacement enzymes (e.g., a Naglu fusion protein) are delivered to one or more tissues of the brainstem. In some embodiments, the targeted one or more tissues of the brainstem include brain stem white matter tissue and/or brain stem nuclei tissue.

In some embodiments, replacement enzymes (e.g., a Naglu fusion protein) are delivered to various brain tissues including, but not limited to, gray matter, white matter, periventricular areas, pia-arachnoid, meninges, neocortex, cerebellum, deep tissues in cerebral cortex, molecular layer, caudate/putamen region, midbrain, deep regions of the pons or medulla, and combinations thereof.

In some embodiments, replacement enzymes (e.g., a Naglu fusion protein) are delivered to various cells in the brain including, but not limited to, neurons, glial cells, perivascular cells and/or meningeal cells. In some embodiments, a therapeutic protein is delivered to oligodendrocytes of deep white matter.

Spinal Cord

In general, regions or tissues of the spinal cord can be characterized based on the depth of the tissues. For example, spinal cord tissues can be characterized as surface or shallow tissues, mid-depth tissues, and/or deep tissues.

In some embodiments, replacement enzymes (e.g., a Naglu fusion protein) are delivered to one or more surface or shallow tissues of the spinal cord. In some embodiments, a targeted surface or shallow tissue of the spinal cord is located within 4 mm from the surface of the spinal cord. In some embodiments, a targeted surface or shallow tissue of the spinal cord contains pia matter and/or the tracts of white matter.

In some embodiments, replacement enzymes (e.g., a Naglu fusion protein) are delivered to one or more deep tissues of the spinal cord. In some embodiments, a targeted deep tissue of the spinal cord is located internal to 4 mm from the surface of the spinal cord. In some embodiments, a targeted deep tissue of the spinal cord contains spinal cord grey matter and/or ependymal cells.

In some embodiments, replacement enzymes (e.g., a Naglu fusion protein) are delivered to neurons of the spinal cord.

Peripheral Target Tissues

As used herein, peripheral organs or tissues refer to any organs or tissues that are not part of the central nervous system (CNS). Peripheral target tissues may include, but are not limited to, blood system, liver, kidney, heart, endothelium, bone marrow and bone marrow derived cells, spleen, lung, lymph node, bone, cartilage, ovary and testis. In some embodiments, a replacement enzyme (e.g., a Naglu fusion protein) in accordance with the present invention is delivered to one or more of the peripheral target tissues.

Biodistribution and Bioavailability

In various embodiments, once delivered to the target tissue, a replacement enzyme (e.g., a Naglu fusion protein) is localized intracellularly. For example, a replacement enzyme (e.g., a Naglu fusion protein) may be localized to exons, axons, lysosomes, mitochondria or vacuoles of a target cell (e.g., neurons such as Purkinje cells). For example, in some embodiments intrathecally-administered enzymes demonstrate translocation dynamics such that the enzyme moves within the perivascular space (e.g., by pulsation-assisted convective mechanisms). In addition, active axonal transport mechanisms relating to the association of the administered protein or enzyme with neurofilaments may also contribute to or otherwise facilitate the distribution of intrathecally-administered proteins or enzymes into the deeper tissues of the central nervous system.

In some embodiments, a replacement enzyme (e.g., a Naglu fusion protein) delivered according to the present invention may achieve therapeutically or clinically effective levels or activities in various targets tissues described herein. As used herein, a therapeutically or clinically effective level or activity is a level or activity sufficient to confer a therapeutic effect in a target tissue. The therapeutic effect may be objective (i.e., measurable by some test or marker) or subjective (i.e., subject gives an indication of or feels an effect). For example, a therapeutically or clinically effective level or activity may be an enzymatic level or activity that is sufficient to ameliorate symptoms associated with the disease in the target tissue (e.g., GAG storage).

In some embodiments, a replacement enzyme (e.g., a Naglu fusion protein) delivered according to the present invention may achieve an enzymatic level or activity that is at least 5%, 10%, 20%, 30%, 40%, 50%, 60%, 70%, 80%, 90%, 95% of the normal level or activity of the corresponding lysosomal enzyme in the target tissue. In some embodiments, a replacement enzyme (e.g., a Naglu fusion protein) delivered according to the present invention may achieve an enzymatic level or activity that is increased by at least 1-fold, 2-fold, 3-fold, 4-fold, 5-fold, 6-fold, 7-fold, 8-fold, 9-fold or 10-fold as compared to a control (e.g., endogenous levels or activities without the treatment). In some embodiments, a replacement enzyme (e.g., a Naglu fusion protein) delivered according to the present invention may achieve an increased enzymatic level or activity at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg or 600 nmol/hr/mg in a target tissue.

In some embodiments, inventive methods according to the present invention are particularly useful for targeting the lumbar region. In some embodiments, a replacement enzyme (e.g., a Naglu fusion protein) delivered according to the present invention may achieve an increased enzymatic level or activity in the lumbar region of at least approximately 500 nmol/hr/mg, 600 nmol/hr/mg, 700 nmol/hr/mg, 800 nmol/hr/mg, 900 nmol/hr/mg, 1000 nmol/hr/mg, 1500 nmol/hr/mg, 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, or 10,000 nmol/hr/mg.

In general, therapeutic agents (e.g., replacement enzymes) delivered according to the present invention have sufficiently long half time in CSF and target tissues of the brain, spinal cord, and peripheral organs. In some embodiments, a replacement enzyme (e.g., a Naglu fusion protein) delivered according to the present invention may have a half-life of at least approximately 30 minutes, 45 minutes, 60 minutes, 90 minutes, 2 hours, 3 hours, 4 hours, 5 hours, 6 hours, 7 hours, 8 hours, 9 hours, 10 hours, 12 hours, 16 hours, 18 hours, 20 hours, 25 hours, 30 hours, 35 hours, 40 hours, up to 3 days, up to 7 days, up to 14 days, up to 21 days or up to a month. In some embodiments, In some embodiments, a replacement enzyme (e.g., a Naglu fusion protein) delivered according to the present invention may retain detectable level or activity in CSF or bloodstream after 12 hours, 24 hours, 30 hours, 36 hours, 42 hours, 48 hours, 54 hours, 60 hours, 66 hours, 72 hours, 78 hours, 84 hours, 90 hours, 96 hours, 102 hours, or a week following administration. Detectable level or activity may be determined using various methods known in the art.

In certain embodiments, a replacement enzyme (e.g., a Naglu fusion protein) delivered according to the present invention achieves a concentration of at least 30 µg/ml in the CNS tissues and cells of the subject following administration (e.g., one week, 3 days, 48 hours, 36 hours, 24 hours, 18 hours, 12 hours, 8 hours, 6 hours, 4 hours, 3 hours, 2 hours, 1 hour, 30 minutes, or less, following intrathecal administration of the pharmaceutical composition to the subject). In certain embodiments, a replacement enzyme (e.g., a Naglu fusion protein) delivered according to the present invention achieves a concentration of at least 20 µg/ml, at least 15 µg/ml, at least 10 µg/ml, at least 7.5 µg/ml, at least 5 µg/ml, at least 2.5 µg/ml, at least 1.0 µg/ml or at least 0.5 µg/ml in the targeted tissues or cells of the subject (e.g., brain tissues or neurons) following administration to such subject (e.g., one week, 3 days, 48 hours, 36 hours, 24 hours, 18 hours, 12 hours, 8 hours, 6 hours, 4 hours, 3 hours, 2 hours, 1 hour, 30 minutes, or less following intrathecal administration of such pharmaceutical compositions to the subject).

Treatment of Sanfilippo Syndrome by Intrathecal Administration

Sanfilippo syndrome, or mucopolysaccharidosis III (MPS III), is a rare genetic disorder characterized by the deficiency of enzymes involved in the degradation of glycosaminoglycans (GAG). In the absence of enzyme, partially degraded GAG molecules cannot be cleared from the body and accumulate in lysosomes of various tissues, resulting in progressive widespread somatic dysfunction (Neufeld and Muenzer, 2001).

Four distinct forms of MPS III, designated MPS IIIA, B, C, and D, have been identified. Each represents a deficiency in one of four enzymes involved in the degradation of the GAG heparan sulfate. All forms include varying degrees of the same clinical symptoms, including coarse facial features, hepatosplenomegaly, corneal clouding and skeletal deformities. Most notably, however, is the severe and progressive loss of cognitive ability, which is tied not only to the accumulation of heparan sulfate in neurons, but also the subsequent elevation of the gangliosides GM2, GM3 and GD2 caused by primary GAG accumulation (Walkley 1998).

Mucopolysaccharidosis type IIIB (MPS IIIB; Sanfilippo B disease) is an autosomal recessive disorder that is characterized by a deficiency of the enzyme alpha-N-acetylglucosaminidase (Naglu). In the absence of this enzyme, GAG heparan sulfate accumulates in lysosomes of neurons and glial cells, with lesser accumulation outside the brain.

A defining clinical feature of this disorder is central nervous system (CNS) degeneration, which results in loss of, or failure to attain, major developmental milestones. The progressive cognitive decline culminates in dementia and premature mortality. The disease typically manifests itself in young children, and the lifespan of an affected individual generally does not extend beyond late teens to early twenties.

Compositions and methods of the present invention may be used to effectively treat individuals suffering from or susceptible to SanB. The terms, "treat" or "treatment," as used herein, refers to amelioration of one or more symptoms associated with the disease, prevention or delay of the onset of one or more symptoms of the disease, and/or lessening of the severity or frequency of one or more symptoms of the disease.

In some embodiments, treatment refers to partially or complete alleviation, amelioration, relief, inhibition, delaying onset, reducing severity and/or incidence of neurological impairment in a SanB patient. As used herein, the term "neurological impairment" includes various symptoms associated with impairment of the central nervous system (e.g., the brain and spinal cord). Symptoms of neurological impairment may include, for example, developmental delay, progressive cognitive impairment, hearing loss, impaired speech development, deficits in motor skills, hyperactivity, aggressiveness and/or sleep disturbances, among others.

Thus, in some embodiments, treatment refers to decreased lysosomal storage (e.g., of GAG) in various tissues. In some embodiments, treatment refers to decreased lysosomal storage in brain target tissues, spinal cord neurons, and/or peripheral target tissues. In certain embodiments, lysosomal storage is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, lysosomal storage is decreased by at least 1-fold, 2-fold, 3-fold, 4-fold, 5-fold, 6-fold, 7-fold, 8-fold, 9-fold or 10-fold as compared to a control. In some embodiments, lysosomal storage is determined by LAMP-1 staining.

In some embodiments, treatment refers to reduced vacuolization in neurons (e.g., neurons containing Purkinje cells). In certain embodiments, vacuolization in neurons is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, vacuolization is decreased by at least 1-fold, 2-fold, 3-fold, 4-fold, 5-fold, 6-fold, 7-fold, 8-fold, 9-fold or 10-fold as compared to a control.

In some embodiments, treatment refers to increased Naglu enzyme activity in various tissues. In some embodiments, treatment refers to increased Naglu enzyme activity in brain target tissues, spinal cord neurons and/or peripheral target tissues. In some embodiments, Naglu enzyme activity is increased by about 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 700%, 800%, 900% 1000% or more as compared to a control. In some embodiments, Naglu enzyme activity is increased by at least 1-fold, 2-fold, 3-fold, 4-fold, 5-fold, 6-fold, 7-fold, 8-fold, 9-fold or 10-fold as compared to a control. In some embodiments, increased Naglu enzymatic activity is at least approximately 10 nmol/hr/mg, 20 nmol/hr/mg, 40 nmol/hr/mg, 50 nmol/hr/mg, 60 nmol/hr/mg, 70 nmol/hr/mg, 80 nmol/hr/mg, 90 nmol/hr/mg, 100 nmol/hr/mg, 150 nmol/hr/mg, 200 nmol/hr/mg, 250 nmol/hr/mg, 300 nmol/hr/mg, 350 nmol/hr/mg, 400 nmol/hr/mg, 450 nmol/hr/mg, 500 nmol/hr/mg, 550 nmol/hr/mg, 600 nmol/hr/mg or more. In some embodiments, Naglu enzymatic activity is increased in the lumbar region. In some embodiments, increased Naglu enzymatic activity in the lumbar region is at least approximately 2000 nmol/hr/mg, 3000 nmol/hr/mg, 4000 nmol/hr/mg, 5000 nmol/hr/mg, 6000 nmol/hr/mg, 7000 nmol/hr/mg, 8000 nmol/hr/mg, 9000 nmol/hr/mg, 10,000 nmol/hr/mg, or more.

In certain embodiments, treatment according to the present invention results in a reduction (e.g., about a 5%, 10%, 15%, 20%, 25%, 30%, 40%, 50%, 55%, 60%, 65%, 70%, 75%, 80%, 90%, 95%, 97.5%, 99% or more reduction) or a complete elimination of the presence, or alternatively the accumulation, of one or more pathological or biological markers which are associated with the lysosomal storage diseases. Such reduction or elimination may be particularly evident in the cells and tissues of the CNS (e.g., neurons and oligodendrocytes). For example, in some embodiments, upon administration to a subject the pharmaceutical compositions of the present invention demonstrate or achieve a reduction in the accumulation of the biomarker lysosomal associated membrane protein 1 (LAMP1) in the CNS cells and tissues of the subject (e.g., in the cerebral cortex, cerebellum, caudate nucleus and putamen, white matter and/or thalamus). LAMP1 is a glycoprotein highly expressed in lysosomal membranes and its presence is elevated many patients with a lysosomal storage disorder. (Meikle, et al. Clin Chem. (1997)43:1325-1335.) The presence or absence of LAMP1 in patients (e.g., as determined by LAMP staining) with a lysosomal storage disease therefore may provide a useful indicator of lysosomal activity and a marker for both the diagnosis and monitoring of lysosomal storage diseases.

Accordingly, some embodiments of the present invention relate to methods of reducing or otherwise eliminating the presence or accumulation of one or more pathological or biological markers associated with a disease (e.g., a lysosomal storage disease). Similarly, some embodiments of the invention relate to methods of increasing the degradation (or the rate of degradation) of one or more pathological or biological markers (e.g., LAMP1) associated with lysosomal storage diseases.

In some embodiments, treatment refers to decreased progression of loss of cognitive ability. In certain embodiments, progression of loss of cognitive ability is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, treatment refers to decreased developmental delay. In certain embodiments, developmental delay is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control.

In some embodiments, treatment refers to increased survival (e.g. survival time). For example, treatment can result in an increased life expectancy of a patient. In some embodiments, treatment according to the present invention results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with similar disease without treatment. In some embodiments, treatment according to the present invention results in an increased life expectancy of a patient by more than about 6 month, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with similar disease without treatment. In some embodiments, treatment according to the present invention results in long term survival of a patient. As used herein, the term "long term survival" refers to a survival time or life expectancy longer than about 40 years, 45 years, 50 years, 55 years, 60 years, or longer.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with SanB, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having SanB or having the potential to develop SanB. The individual can have residual endogenous Naglu expression and/or activity, or no measurable activity. For example, the individual having SanB may have Naglu expression levels that are less than about 30-50%, less than about 25-30%, less than about 20-25%, less than about 15-20%, less than about 10-15%, less than about 5-10%, less than about 0.1-5% of normal Naglu expression levels.

In some embodiments, the individual is an individual who has been recently diagnosed with the disease. Typically, early treatment (treatment commencing as soon as possible after diagnosis) is important to minimize the effects of the disease and to maximize the benefits of treatment.

Immune Tolerance

Generally, intrathecal administration of a replacement enzyme (e.g., a Naglu fusion protein) according to the present invention does not result in severe adverse effects in the subject. As used herein, severe adverse effects induce, but are not limited to, substantial immune response, toxicity, or death. As used herein, the term "substantial immune response" refers to severe or serious immune responses, such as adaptive T-cell immune responses.

Thus, in many embodiments, inventive methods according to the present invention do not involve concurrent immunosuppressant therapy (i.e., any immunosuppressant therapy used as pre-treatment/pre-conditioning or in parallel to the method). In some embodiments, inventive methods according to the present invention do not involve an immune tolerance induction in the subject being treated. In some embodiments, inventive methods according to the present invention do not involve a pre-treatment or preconditioning of the subject using T-cell immunosuppressive agent.

In some embodiments, intrathecal administration of therapeutic agents can mount an immune response against these agents. Thus, in some embodiments, it may be useful to render the subject receiving the replacement enzyme tolerant to the enzyme replacement therapy Immune tolerance may be induced using various methods known in the art. For example, an initial 30-60 day regimen of a T-cell immunosuppressive agent such as cyclosporin A (CsA) and an antiproliferative agent, such as, azathioprine (Aza), combined with weekly intrathecal infusions of low doses of a desired replacement enzyme may be used.

Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additionalimmunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin Nephrol. 20, 108-125; Chirmule et al., 2000, J. Virol. 74, 3345-3352; Ito et al., 2000, J. Immunol. 164, 1230-1235).

Administration

Inventive methods of the present invention contemplate single as well as multiple administrations of a therapeutically effective amount of a replacement enzyme (e.g., a Naglu fusion protein) described herein. Replacement enzymes (e.g., a Naglu fusion protein) can be administered at regular intervals, depending on the nature, severity and extent of the subject's condition. In some embodiments, a therapeutically effective amount of the a replacement enzyme (e.g., a Naglu fusion protein) of the present invention may be administered intrathecally periodically at regular intervals (e.g., once every year, once every six months, once every five months, once every three months, bimonthly (once every two months), monthly (once every month), biweekly (once every two weeks), weekly).

In some embodiments, intrathecal administration may be used in conjunction with other routes of administration (e.g., intravenous, subcutaneously, intramuscularly, parenterally, transdermally, or transmucosally (e.g., orally or nasally)). In some embodiments, those other routes of administration (e.g., intravenous administration) may be performed no more frequent than biweekly, monthly, once every two months, once every three months, once every four months, once every five months, once every six months, annually administration.

As used herein, the term "therapeutically effective amount" is largely determined base on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). For example, a therapeutically effective amount may be an amount sufficient to achieve a desired therapeutic and/or prophylactic effect, such as an amount sufficient to modulate lysosomal enzyme receptors or their activity to thereby treat such lysosomal storage disease or the symptoms thereof (e.g., a reduction in or elimination of the presence or incidence of "zebra bodies" or cellular vacuolization following the administration of the compositions of the present invention to a subject). Generally, the amount of a therapeutic agent (e.g., a recombinant lysosomal enzyme) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific fusion protein employed; the duration of the treatment; and like factors as is well known in the medical arts.

In some embodiments, the therapeutically effective dose ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, the therapeutically effective dose is greater than about 0.1 mg/kg brain weight, greater than about 0.5 mg/kg brain weight, greater than about 1.0 mg/kg brain weight, greater than about 3 mg/kg brain weight, greater than about 5 mg/kg brain weight, greater than about 10 mg/kg brain weight, greater than about 15 mg/kg brain weight, greater than about 20 mg/kg brain weight, greater than about 30 mg/kg brain weight, greater than about 40 mg/kg brain weight, greater than about 50 mg/kg brain weight, greater than about 60 mg/kg brain weight, greater than about 70 mg/kg brain weight, greater than about 80 mg/kg brain weight, greater than about 90 mg/kg brain weight, greater than about 100 mg/kg brain weight, greater than about 150 mg/kg brain weight, greater than about 200 mg/kg brain weight, greater than about 250 mg/kg brain weight, greater than about 300 mg/kg brain weight, greater than about 350 mg/kg brain weight, greater than about 400 mg/kg brain weight, greater than about 450 mg/kg brain weight, greater than about 500 mg/kg brain weight.

In some embodiments, the therapeutically effective dose may also be defined by mg/kg body weight. As one skilled in the art would appreciate, the brain weights and body weights can be correlated. Dekaban A S. "Changes in brain weights during the span of human life: relation of brain weights to body heights and body weights," Ann Neurol 1978; 4:345-56. Thus, in some embodiments, the dosages can be converted as shown in Table 4.

TABLE 4

| Correlation between Brain Weights, body weights and ages of males | | | | |
|---|---|---|---|---|
| Age (year) | (kg) | Brain weight | (kg) | Body weight |
| 3 (31-43 months) | | 1.27 | | 15.55 |
| 4-5 | | 1.30 | | 19.46 |

In some embodiments, the therapeutically effective dose may also be defined by mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson C E, et al. "Multiplicity of cerebrospinal fluid functions: New challenges in health and disease," Cerebrospinal Fluid Res. 2008 May 14; 5:10). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

Kits

The present invention further provides kits or other articles of manufacture which contains the formulation of the present invention and provides instructions for its reconstitution (if lyophilized) and/or use. Kits or other articles of manufacture may include a container, an IDDD, a catheter and any other articles, devices or equipment useful in interthecal administration and associated surgery. Suitable containers include, for example, bottles, vials, syringes (e.g., pre-filled syringes), ampules, cartridges, reservoirs, or lyojects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may holds formulations and a label on, or associated with, the container that may indicate directions for reconstitution and/or use. For example, the label may indicate that the formulation is reconstituted to protein concentrations as described above. The label may further indicate that the formulation is useful or intended for, for example, IT administration. In some embodiments, a container may contain a single dose of a stable formulation containing a replacement enzyme (e.g., a Naglu fusion protein). In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 25 mg/ml, at least 50 mg/ml, at least 75 mg/ml, at least 100 mg/ml). Kits or other articles of manufacture may further include other materials desirable from a commercial and user standpoint, including other buffers, diluents, filters, needles, IDDDs, catheters, syringes, and package inserts with instructions for use.

The invention will be more fully understood by reference to the following examples. They should not, however, be construed as limiting the scope of the invention. All literature citations are incorporated by reference.

EXAMPLES

Example 1: Expression of rhNaglu and Naglu Fusion Proteins

This example demonstrates the development of a recombinant human Naglu protein intended for direct administration into the central nervous system of Sanfilippo B patients via intrathecal injections.

Sanfilippo type B (Sanfilippo B) is an autosomal recessive disorder that is caused by the deficiency of alpha-N-acetyl-glucosaminidase (Naglu). Naglu is the enzyme that removes the alpha-N-acetyl-glucosamine from the non-reducing end of oligosaccharides in the heparin sulfate degradation pathway. The human gene coding for Naglu has six exons spanning over 8.2 kb long on chromosome 17q21.1. Human Naglu is synthesized in the cells as a 743 amino acid precursor that contains a signal peptide. The full length amino acid sequence of Naglu is provided below in Table 5:

TABLE 5

MEAVAVAAAVGVLLLAGAGGAAGDEAREAAAVRALVARLLGPGPAADFS
VSVERALAAKPGLDTYSLGGGGAARVRVRGSTGVAAAAGLHRYLRDFCG
CHVAWSGSQLRLPRPLPAVPGELTEATPNRYRYYQNVCTQSYSFVWWDW
ARWEREIDWMALNGINLALAWSGQEAIWQRVYLALGLTQAEINEFFTGP
AFLAWGRMGNLHTWDGPLPPSWHIKQLYLQHRVLDQMRSFGMTPVLPAF
AGHVPEAVTRVFPQVNVTKMGSWGHFNCSYSCSFLLAPEDPIFPIIGSL
FLRELIKEFGTDHIYGADTFNEMQPPSSEPSYLAAATTAVYEAMTAVDT
EAVWLLQGWLFQHQPQFWGPAQIRAVLGAVPRGRLLVLDLFAESQPVYT
RTASFQGQPFIWCMLHNFGGNHGLFGALEAVNGGPEAARLFPNSTMVGT
GMAPEGISQNEVVYSLMAELGWRKDPVPDLAAWVTSFAARRYGVSHPDA
GAAWRLLLRSVYNCSGEACRGHNRSPLVRRPSLQMNTSIWYNRSDVFEA
WRLLLTSAPSLATSPAFRYDLLDLTRQAVQELVSLYYEEARSAYLSKEL
ASLLRAGGVLAYELLPALDEVLASDSRFLLGSWLEQARAAAVSEAEADF
YEQNSRYQLTLWGPEGNILDYANKQLAGLVANYYTPRWRLFLEALVDSV
AQGIPFQQHQFDKNVFQLEQAFVLSKQRYPSQPRGDTVDLAKKIFLKYY
PRWVAGSW (SEQ ID NO: 2)

The 23 amino acid signal peptide is removed as the protein enters the endoplasmic reticulum. The resulting mature Naglu protein is sorted to lysosomes where enzymatic degradation of heparin sulfate takes place or secreted into the extracellular space. The molecular weight of mature recombinant human Naglu is 80.2 kDa without glycosylation and approximately 93.4 kDa with the added weight of glycosylation. The mature Naglu protein sequence, in which amino acid residues 1-23 are cleaved, is provided below in Table 6.

TABLE 6

DEAREAAAVRALVARLLGPGPAADFSVSVERALAAKPGLDTYSLGGGGA
ARVRVRGSTGVAAAAGLHRYLRDFCGCHVAWSGSQLRLPRPLPAVPGEL
TEATPNRYRYYQNVCTQSYSFVWWDWARWEREIDWMALNGINLALAWSG
QEAIWQRVYLALGLTQAEINEFFTGPAFLAWGRMGNLHTWDGPLPPSWH

TABLE 6 -continued

IKQLYLQHRVLDQMRSFGMTPVLPAFAGHVPEAVTRVFPQVNVTKMGSW
GHFNCSYSCSFLLAPEDPIFPIIGSLFLRELIKEFGTDHIYGADTFNEM
QPPSSEPSYLAAATTAVYEAMTAVDTEAVWLLQGWLFQHQPQFWGPAQI
RAVLGAVPRGRLLVLDLFAESQPVYTRTASFQGQPFIWCMLHNFGGNHG
LFGALEAVNGGPEAARLFPNSTMVGTGMAPEGISQNEVVYSLMAELGWR
KDPVPDLAAWVTSFAARRYGVSHPDAGAAWRLLLRSVYNCSGEACRGHN
RSPLVRRPSLQMNTSIWYNRSDVFEAWRLLLTSAPSLATSPAFRYDLLD
LTRQAVQELVSLYYEEARSAYLSKELASLLRAGGVLAYELLPALDEVLA
SDSRFLLGSWLEQARAAAVSEAEADFYEQNSRYQLTLWGPEGNILDYAN
KQLAGLVANYYTPRWRLFLEALVDSVAQGIPFQQHQFDKNVFQLEQAFV
LSKQRYPSQPRGDTVDLAKKIFLKYYPRWVAGSW (SEQ ID NO: 1)

To generate recombinant human Naglu (rhNaglu), the human Naglu cDNA was inserted into an expression vector and transfected into the HT1080 cell line. A Naglu enzymatic activity assay was used to screen for high expressing HT1080 clones. The secreted protein generated by Naglu expressing HT1080 cells is the mature form of human Naglu. The recombinant human Naglu produced by HT1080 cells was glycosylated. The rhNaglu is fully active toward a synthetic substrate, 4-MU-N-acetyl alpha-D-glucosaminide.

The most significant difference between recombinant Naglu and that isolated from natural sources, such as urinary, placental, and liver Naglu is the lack of the mannose-6-phosphate glycan (M6P). The lack of M6P in recombinant Naglu has been reported by several investigators in the study of CHO and HEK 293 cell-derived rhNaglu. HT1080 expressed rhNaglu was also found to be deprived of M6P glycan. The mechanism for the lack of M6P in recombinant Naglu is not known. The present inventors have developed several fusion proteins and glycan modifications in an effort to overcome the dependence of M6P for cellular delivery in recombinant Naglu (FIGS. 1, 2, and 3A and 3B).

Naglu-TAT

A fusion protein of Naglu and the protein transduction domain from HIV was named Naglu-TAT. Naglu-TAT was designed and produced, and purified. TAT peptide has been shown to facilitate protein transduction through the cellular membranes into the cytoplasm. It has been demonstrated previously that the TAT peptide fused with the lysosomal enzyme beta-glucouronidase (GUS-TAT) resulted in greater lysosomal storage reduction in the Kidney than GUS after IV injection into MPSVII mice (Grubb J H et al., Rejuvenation Research 13:2, 2010). Separate experiments demonstrated improved cellular uptake of Naglu-TAT in Sanfilippo B patient fibroblasts compared to rhNaglu (data not shown). However in vivo biodistribution studies indicated that upon IT injection, Naglu-TAT showed similar biodistribution as rhNaglu and only slightly improved cellular uptake. In this study, the majority of the protein remained in the meninges with very limited penetration to the parenchyma of the brain. This result indicated that TAT peptide-mediated delivery was not sufficient to replace receptor mediated cellular uptake of Naglu.

Naglu Kif

Naglu-Kif was produced by using a modified cell culture process with the addition of Kifunensine to the media. Naglu-Kif was proposed and produced and purified. The addition of Kifunensine altered the glycosylation pathway of rhNaglu to enhance the production of high mannose glycan and repress the addition of complex carbohydrates. Kifunensine inhibits the Golgi alpha-mannosidase I activity, and thereby inhibits the removal of the high mannose glycan, leading to the repression of the coupling of complex glycans. As a result, Naglu-Kif contains mostly high mannose glycans. Cellular uptake using macrophage derived cell lines confirmed the mannose receptor dependant uptake of Naglu-Kif. However, an in vivo experiment indicated that upon intrathecal injection into the cerebrospinal fluid of wild type cannulated rats, Naglu-Kif failed to show improved distribution into the parenchyma of the brain over rhNaglu. It was concluded that Mannose receptor mediated uptake of Naglu-Kif will not facilitate rhNaglu delivery in the CNS.

Naglu-ApoE

The receptor binding domain of ApoE (Apolipoprotein E) was fused to the C-terminus of Naglu to utilize the low density lipoprotein receptor (LDLR) for the cellular uptake of Naglu. This approach was based on studies that support the presence of LDLR at the BBB (Begley D J et al., Current Pharmaceutical Design, 2008, 14, 1566-1580). A preliminary mouse in vivo study indicated that Naglu-ApoE administered intravenously into Sanfilippo B mouse did not transport into the brain.

IV Administration of rhNaglu

In vivo experiments were conducted to investigate rhNaglu and Naglu-IGFII in transporting through the BBB. The study indicated that IV administration of rhNaglu and Naglu-IGFII in Sanfilippo B mouse didn't result in any enzyme in the brain, and no histo-pathological improvement were found in the brain of treated mouse.

Naglu-IGFII

Naglu-IGFII was constructed by fusing a portion of the Insulin-like Growth Factor II sequence (aa 8 to 67, 8-67IGFII) to the C-terminus of the Naglu sequence. Compared to the full-length IGFII molecule, 8-67IGFII is reported to bind to M6P/IGF II receptor with a 2-10 fold higher affinity while its ability to bind to the IGF I receptor is decreased 30 fold (Hashimoto R, JBC 1995 270(30):18013-18018).

The Naglu-IGFII molecule contains a linker sequence that was inserted between Naglu and 8-67IGFII. This linker sequence consisted of three tandem repeats of "GGGG-GAAAAGGGG" (SEQ ID NO:4) with two "GAP" sequences flanking each end and one "GAP" sequences in between each repeat. The actual sequence of the linker is provided in Table 7 below:

TABLE 7

Linker sequence

Naglu-GAPGGGGGAAAAGGGGGAPGGGGGAAAAGGGGGAPGGGGGAAA
AGGGGGAP-IGFII

To generate recombinant Naglu-IGFII fusion, the cDNA was inserted into an expression vector, pXD671, and transfected into a human fibroblast cell line. The protein sequence of the recombinant Naglu-IGFII fusion protein is provided below in Table 8:

TABLE 8

Protein Sequence of Recombinant Naglu-IGFII Fusion Protein

DEAREAAAVRALVARLLGPGPAADFSVSVERALAAKPGLDTYSLGGGGA
ARVRVRGSTGVAAAAGLHRYLRDFCGCHVAWSGSQLRLPRPLPAVPGEL
TEATPNRYRYYQNVCTQSYSFVWWDWARWEREIDWMALNGINLALAWSG
QEAIWQRVYLALGLTQAEINEFFTGPAFLAWGRMGNLHTWDGPLPPSWH
IKQLYLQHRVLDQMRSFGMTPVLPAFAGHVPEAVTRVFPQVNVTKMGSW
GHFNCSYSCSFLLAPEDPIFPIIGSLFLRELIKEFGTDHIYGADTFNEM
QPPSSEPSYLAAATTAVYEAMTAVDTEAVWLLQGWLFQHQPQFWGPAQI
RAVLGAVPRGRLLVLDLFAESQPVYTRTASFQGQPFIWCMLHNFGGNHG
LFGALEAVNGGPEAARLFPNSTMVGTGMAPEGISQNEVVYSLMAELGWR
KDPVPDLAAWVTSFAARRYGVSHPDAGAAWRLLLRSVYNCSGEACRGHN
RSPLVRRPSLQMNTSIWYNRSDVFEAWRLLLTSAPSLATSPAFRYDLLD

TABLE 8 -continued

Protein Sequence of Recombinant Naglu-IGFII Fusion Protein

LTRQAVQELVSLYYEEARSAYLSKELASLLRAGGVLAYELLPALDEVLA
SDSRFLLGSWLEQARAAAVSEAEADFYEQNSRYQLTLWGPEGNILDYAN
KQLAGLVANYYTPRWRLFLEALVDSVAQGIPFQQHQFDKNVFQLEQAFV
LSKQRYPSQPRGDTVDLAKKIFLKYYPRWVAGSWGAPGGGGGAAAAAGG
GGGGAPGGGGGAAAAAGGGGGAPGGGGGAAAAAGGGGGAPLCGGELV
DTLQFVCGDRGFYFSRPASRVSRRSRGIVEECCFRSCDLALLETYCATP
AKSE (SEQ ID NO: 6)

Figure 1:
FIG. 1.
Figure 3:
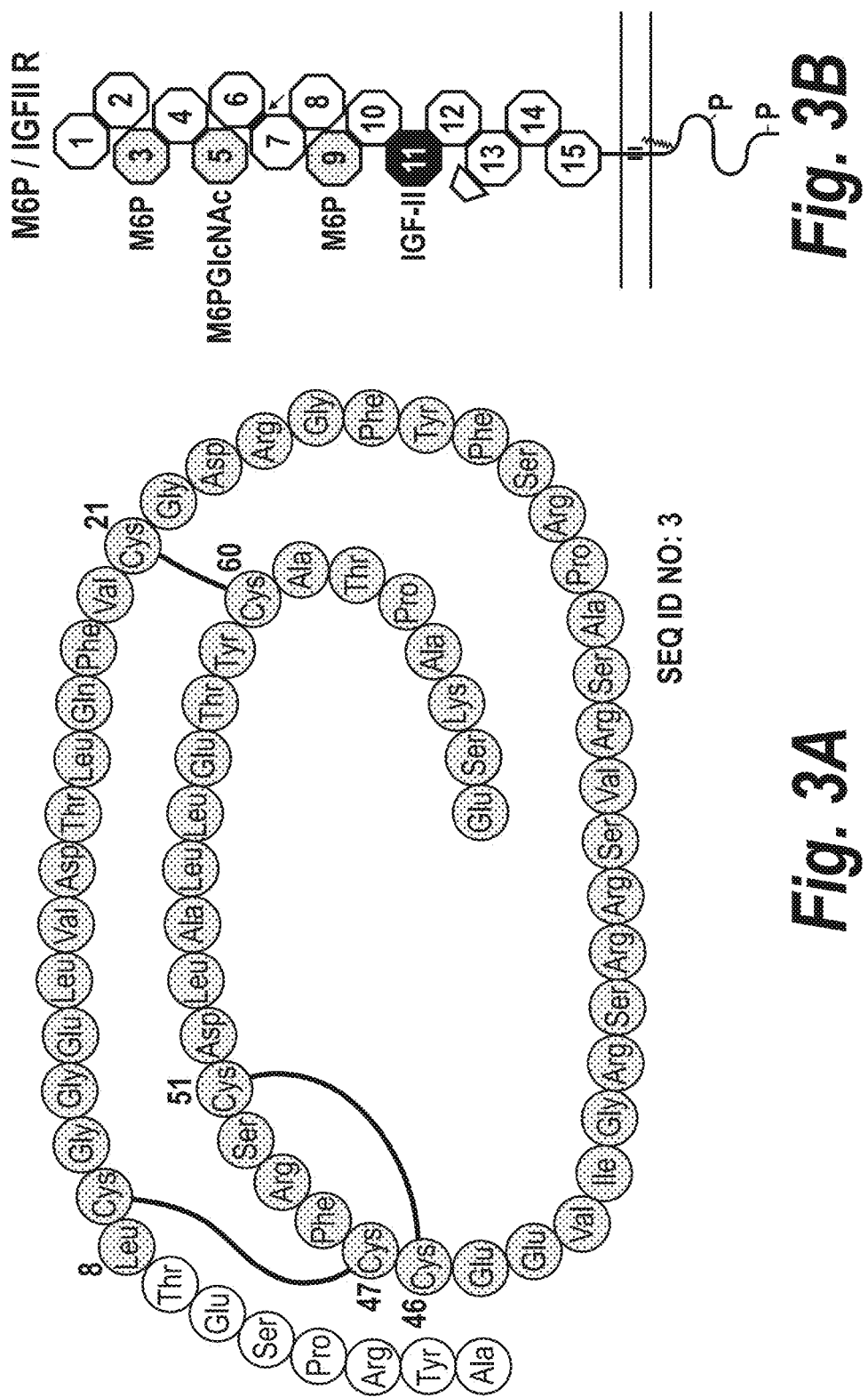
FIGS. 3A and 3B.
Figure 4:
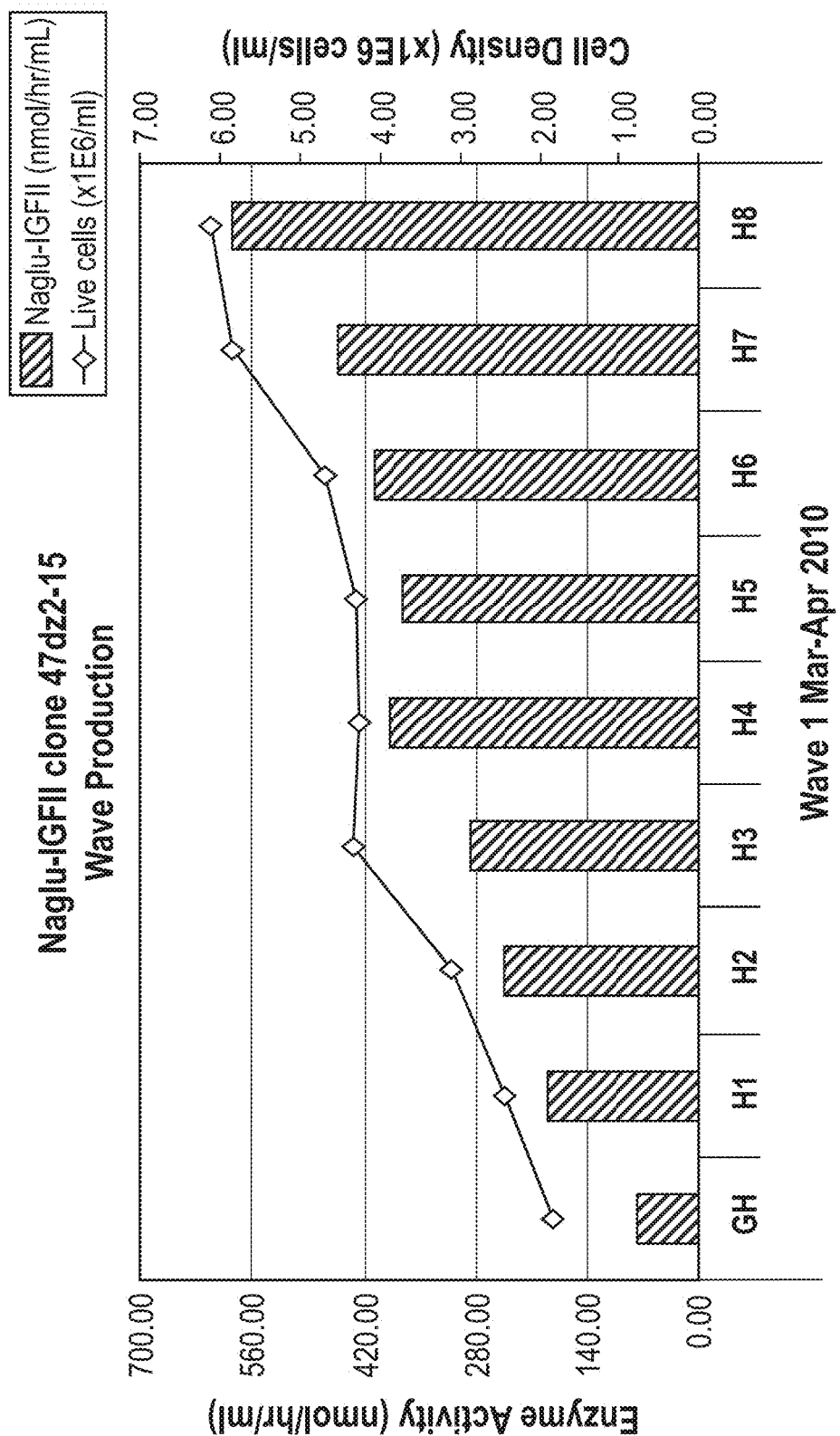
FIG. 4.
Figure 5:
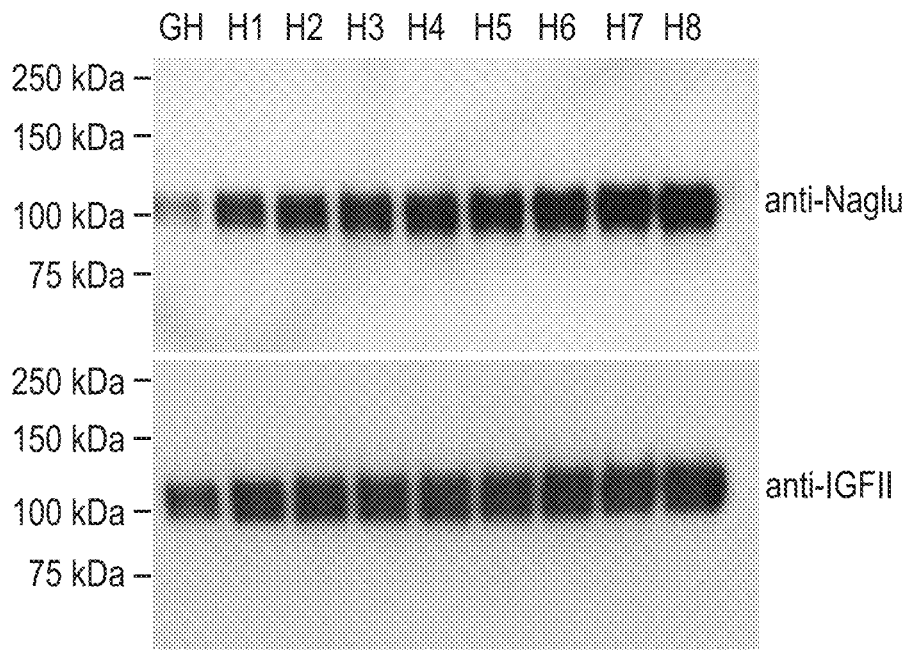
FIG. 5.
Figure 6:
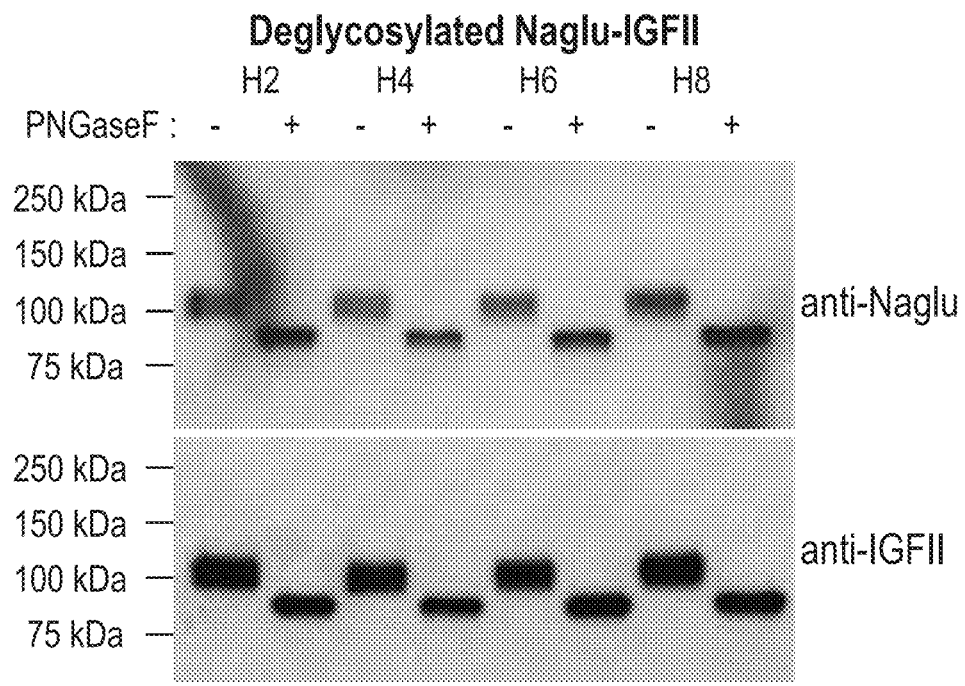
FIG. 6.

Naglu enzymatic activity assay was used to screen for high expressing HT1080 clones. To further increase the expression of Naglu-IGFII, the selected cell line was transfected again with additional expression plasmid carrying the same transcription unit. In both the single transfected and the double transfected cell lines, the secreted Naglu-IGFII contains the full length mature Naglu sequence and full length 8-67IGFII. The Naglu-IGFII fusion protein showed enzymatic activity toward the same synthetic substrate, 4-MU-N-acetyl alpha-D-glucosaminide FIGS. 4-6 depict an exemplary wave production run using the double transfected Naglu-IGFII cell line. The wave production of this Naglu-IGFII cell line presented in FIG. 4 achieved 0.5 pcd (pictogram per-million-cells per-day) of Naglu-IGFII.

Purification of rhNaglu and Naglu-IGFII

A similar purification process was applied for rhNaglu, Naglu-IGFII, Naglu-ApoE and Naglu Kif. A modified purification process was applied for Naglu-TAT. The purification of rhNaglu and Naglu-IGFII protein are summarized below.

For the purification of rhNaglu and Naglu-IGFII, a three step process was utilized (FIGS. 7A and 7B). First, the conditioned media was concentrated using an Ultra-filtration (UF) device. The concentrated media was then applied to a Butyl sepharose chromatography column (Butyl), and then subsequently, a Q sepharose chromatography column (Q). The purified protein was buffer exchanged into a formulation of PBS (11.9 mM sodium phosphate, 2.7 mM potassium phosphate, 137 mM sodium chloride at pH 7.4) for storage. The purified rhNaglu and Naglu-IGFII had purity of 99% and 95% respectively as evaluated by reverse phase high pressure liquid chromatography (data not shown).

Biochemical Property of rhNaglu and Naglu-IGFII

All of the Naglu variants, rhNaglu, Naglu-TAT, Naglu-IGFII, Naglu-Kif and Naglu-ApoE exhibited similar biological activity toward the synthetic substrate, 4-methylumbelliferyl-N-acetyl-a-D-glucosaminide. All of the variants were negative for phospharylated glycosylations as determined by glycan analysis through high performance anion exchange chromatography and by monosaccharide analysis.

The following section summarizes the biochemical properties of rhNaglu and Naglu-IGFII only (Table 9). As can be seen in Table 9, Biochemical comparison of rhNaglu and Naglu-IGFII indicates similar enzymatic activity and stability between the two proteins. The optimum pH for thermal stability measured by Differential Scanning calorimetry for rhNaglu was pH 5-pH 6.5, and pH 6 to pH 6.5 for Naglu-IGFII. This result is in agreement with the requirement for lysosomal hydrolysase to exhibit optimal stability in the acidic environment of the lysosomes.

TABLE 9

Biochemical comparison of rhNaglu and Naglu-IGFII

| Expression System | HT 1080 cells |
|---|---|
| Formulation (PBS) | 11.9 mM sodium phosphate, |
| | 2.7 mM potassium phosphate |
| | 137 mM sodium chloride at pH 7.4 |

TABLE 9-continued

Biochemical comparison of rhNaglu and Naglu-IGFII

| | |
|---|---|
| Solubility Limits | 16.5 mg/mL; rhNaglu |
| | 26 mg/mL; Naglu-IGFII |
| Enzymatic Activity | Km = 0.3 mM; rhNaglu |
| | Km = 0.2 mM; Naglu-IGFII |
| Optimum pH for Thermo-stability | 5-6.5; rhNaglu |
| | 6-6.5; Naglu-IGFII |
| Native Association State | Trimer (MALS and AUC) |
| | (Crystal Structure of rhNaglu) |
| M6P Glycosylation | Negative |

Additionally, Naglu-IGFII was concentrated successfully up to 26 mg/ml as determined by a Bradford protein assay and without signs of aggregation or loss of activity after stored at 4° C. for up to 3 month. A formulation (e.g., for IT administration) of 5 mM Sodium Phosphate pH 6.5, 150 mM Sodium Chloride, 0.005% Polysorbate 20 was also tested for Naglu-IGFII formulation. Similar stability and solubility were observed between Naglu-IGFII in the PBS formulation and the IT formulations (data not shown).

Crystal Structure of Naglu

One of the breakthroughs in the development of rhNaglu was the determination of the crystal structure of Naglu by PEPR. This accomplishment provided insight to the structure of Naglu, and aid in predicting protein stability and formulation requirement. It is contemplated that the alignment of Sanfilippo B patient mutations on 3D structure of Naglu will provide insight and a tool for drug development.

Figure 9:
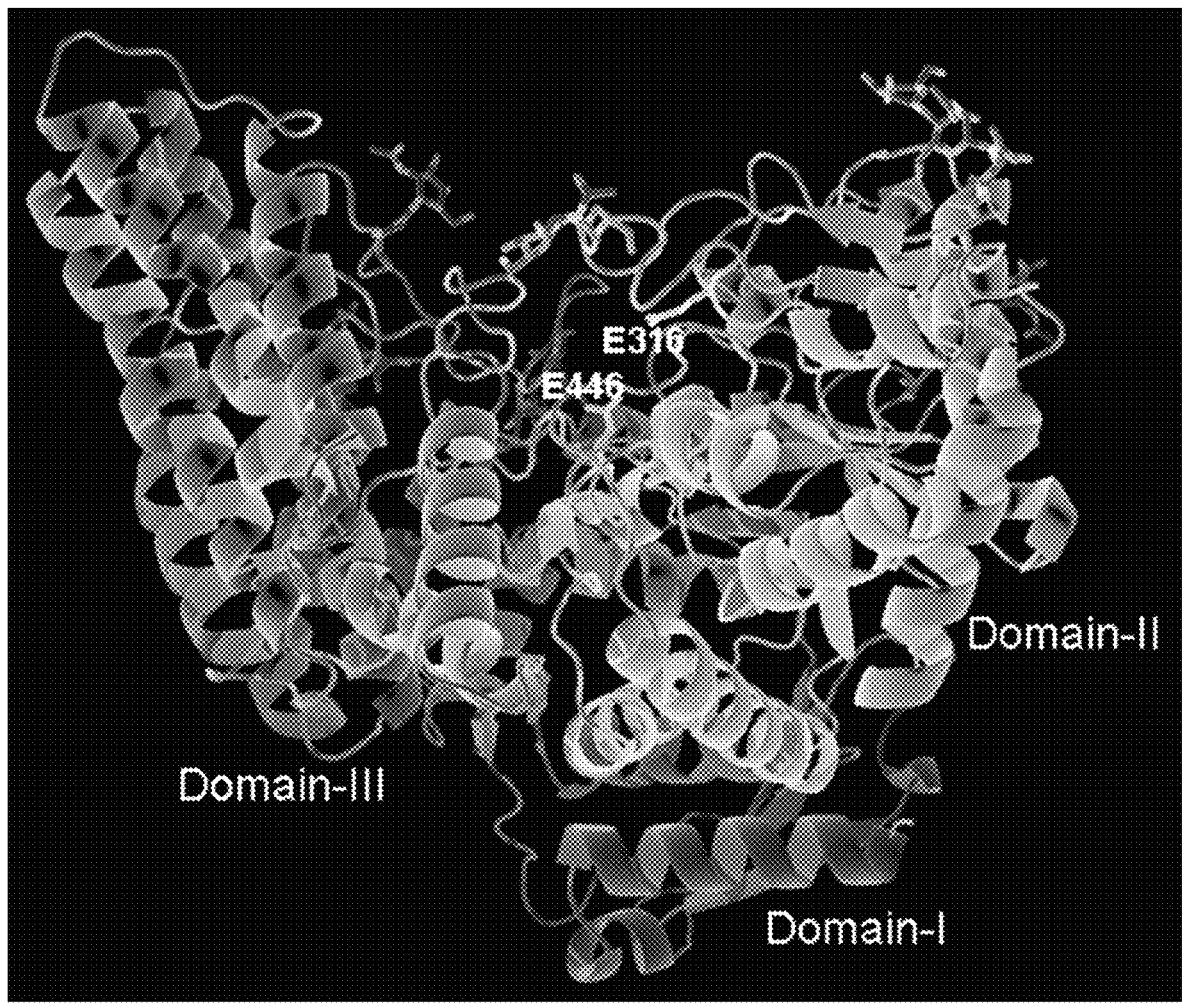
FIG. 9.

The crystals (FIG. 8) were obtained from rhNaglu protein purified from culture media treated with mannosidase-I inhibitor, Kifunensine. Naglu Kif contains identical protein sequences as rhNaglu, but different glycosylation pattern. The crystals acquired of Naglu Kif were grown at pH=7.5 and the structure of Naglu Kif was solved at 2.4 Å resolution by X-ray crystallography. Naglu structure (FIG. 9) is identified as having three distinct domains, a N-terminal domain (Domain-I, aa 24-126) followed by a (α/β)8 barrel domain containing the catalytic glutamates (Domain-II, aa 127-467) and an all helical C-terminal domain (Domain-III, aa 468-743). Similar domain structure has been observed for another Glycoside Hydrolase family-89 protein, cpGH89, a bacterial homolog of Naglu (Ficko-Blean E, et al., PNAS May 6, 2008 vol. 105 no. 18 6560-6565). The active site is at a cleft between domains II and III and the catalytic residues are identified as E316 and E446 located on domain II.

A close packed symmetric trimer arrangement of Naglu molecules can be seen in the crystal structure (FIG. 10), which is in agreement with the native association state observed from analytical ultracentrifugation (AUC) and size exclusion chromatography with in line multi-angle light scattering (SEC-MALS) experiments. Hydrophobic interaction and hydrogen bonds in domain II hold the trimeric conformation of the protein. H227 appears to form a stacking interactions with R297 of an adjacent molecule during trimerization. Additionally, E302 forms intermolecular hydrogen bonding interaction with K301.

Naglu has six potential N-glycosylation sites (N261, N272, N435, N503, N526 and N532) and all the six sites are glycosylated in the crystal structure. Clear electron densities for two NAG molecules attached to each of N272 and N435 and one NAG molecule each attached to N261, N503, N526 and N532 were seen in the electron density map at 2.4 Å resolution. The remainder of the glycan structures are not clearly visible in the electron density map due to the flexible nature of solvent exposed sugar moieties.

The structural information of Naglu aids in the stability analysis and molecular level characterization of Naglu. There are eight cysteines in Naglu, four of them form two disulfide bridges (Cys273-Cys277 and Cys504-Cys509). The other four, C97, C99, C136 and C405 appear as reduced cysteines in the crystal structure even though no reducing agents were used during the purification and crystallization processes. C97 and C99 are close to each other and are partially exposed near the surface. However C136 and C405 are buried and are unlikely to form intermolecular disulfide bonds based on the structure.

Figure 10:
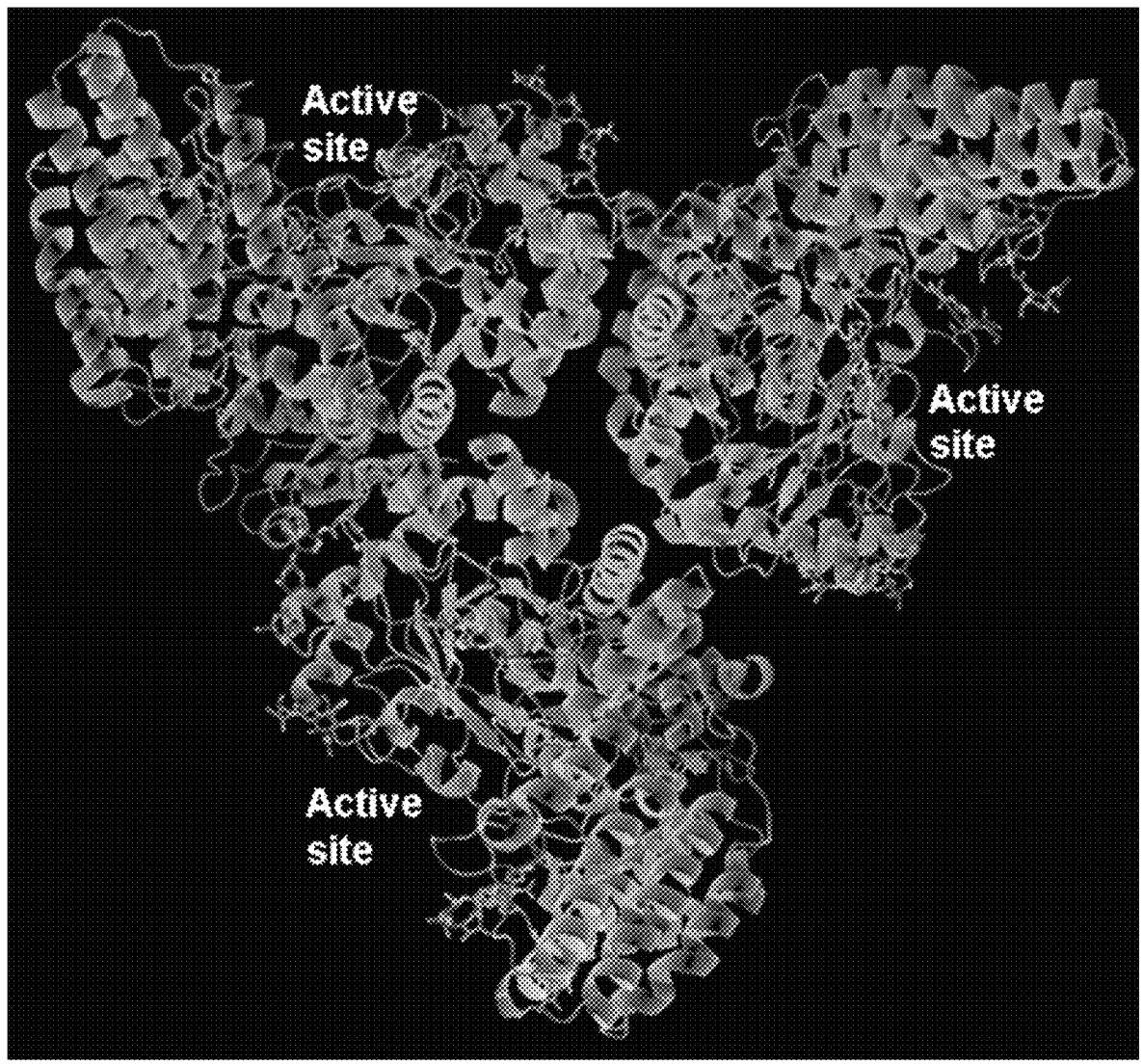
FIG. 10.

It is contemplated that, based on the structural information currently available, mapping of Sanfilippo B patient mutations will shed light on future drug development potentials for this disease such as rational design of small molecular chaperones. Reported severe San B mutations from the literature (Yogalingam 2001) were mapped onto the crystal structure. A few clusters of mutations could be related to structural or functional regions, such as the active site, a loop containing three glycosylation sites in domain-III, and the interface between the three domains (FIG. 10). In addition, clusters of mutations could be seen in N-terminal domain-I and C-term helical bundle domain-III. Most of these residues that are mutated are part of hydrogen bonding and other non-covalent interactions and are involved in the structural stabilization of Naglu.

Example 2: In Vitro Study of rhNaglu and Naglu-IGFII

The mechanism of cellular uptake by each of the Naglu variants was studied using two strains of Sanfilippo B patient fibroblast cells, GM02391 (P359L) and GM 01426 (E153K), and a normal human fibroblast cell line. Attributed to M6P receptor expression on the cell line, fibroblast cells are traditionally used by researchers for the study of lysosomal enzymes cellular uptake.

Figure 11:
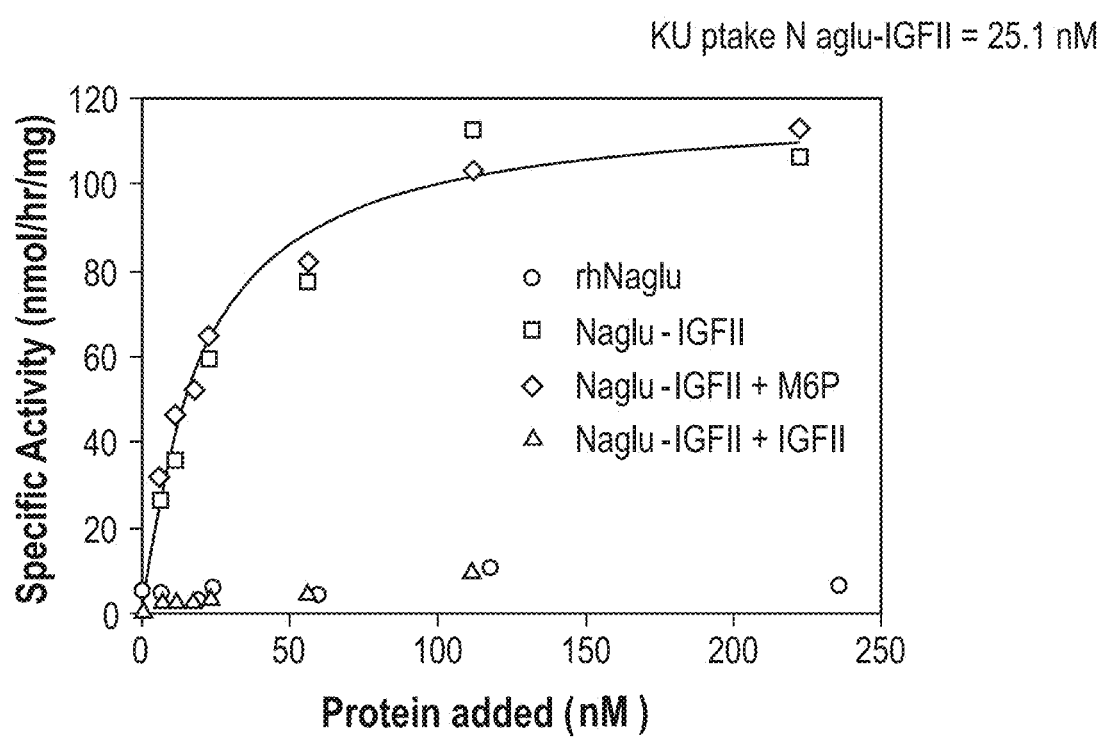
FIG. 11.

Cellular uptake studies were done by incubation of fibroblast cells with rhNaglu or Naglu-IGFII for four hours at 37° C. Cells were washed and lysed after incubation, and Naglu enzymatic activity in cell lysates was measured. Incubation of rhNaglu with fibroblast cells resulted in barely detectable amount of enzyme intracellularly. In contrast, incubation of Naglu-IGFII with fibroblast cells resulted in pronounced level of enzyme intracellularly (FIG. 11). The amount of internalized Naglu-IGFII reached saturation as the amount of enzyme used for incubation increased. The dose dependant saturating uptake is a typical finding for receptor mediated cellular uptake. Furthermore, the internalization of Naglu-IGFII was not inhibited by exogenous M6P, but was inhibited by exogenous IGFII completely (FIG. 11). This result indicated that Naglu-IGFII internalization into fibroblast cells is dependant on M6P/IGFII receptor in a glycosylation independent manner.

Figure 12:
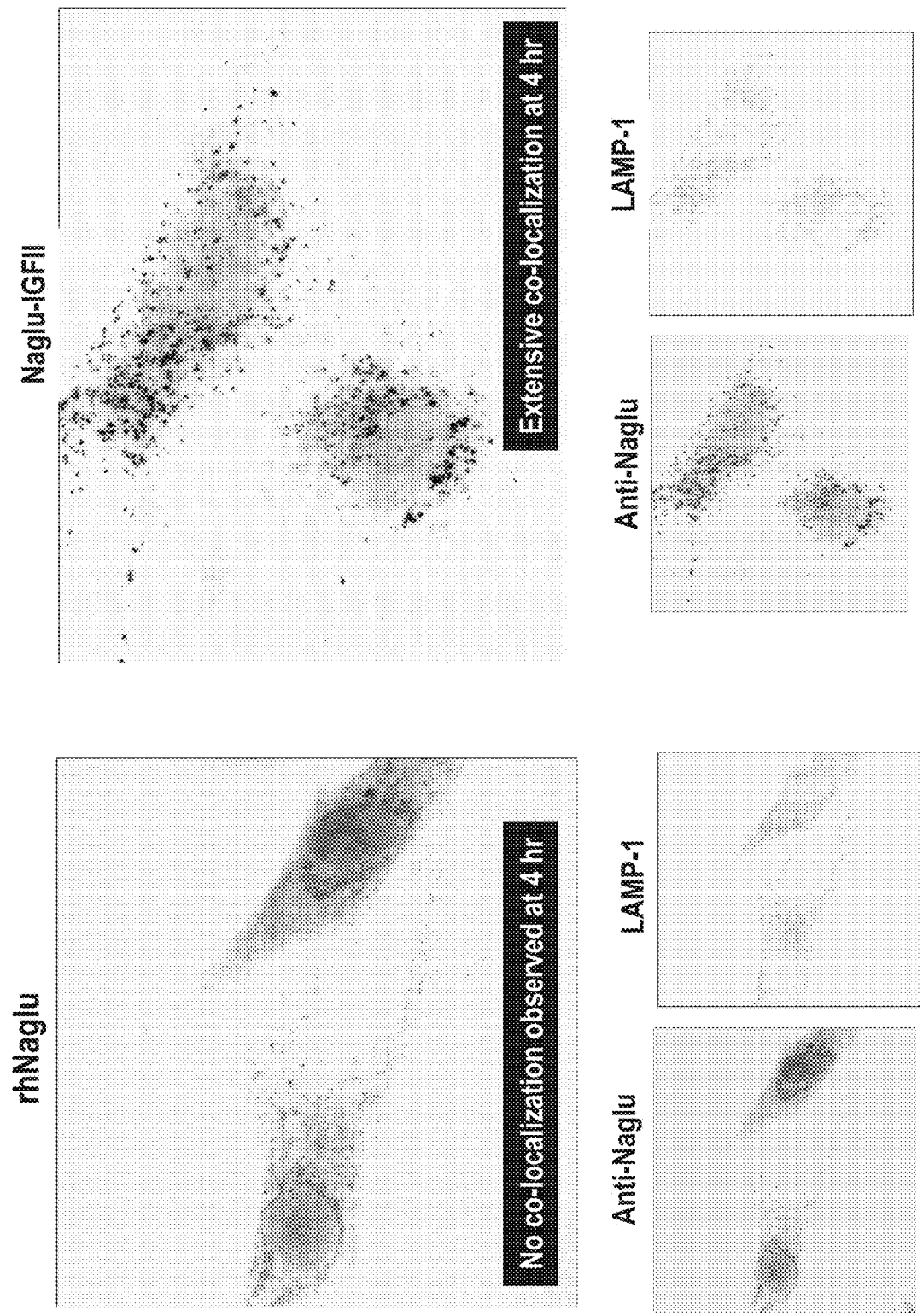
FIG. 12.

An experiment was also conducted to study the trafficking of rhNaglu and Naglu-IGFII to lysosomes. Sanfilippo B patient fibroblast cells (GM01426) were used for this study. Detection of rhNaglu and Naglu-IGFII was examined by staining the cells with anti-human Naglu polyclonal antibody after initial incubation of the proteins with the cells. Immunofluorescent staining of LAMP-1 (lysosomal associated membrane protein 1) was used for the detection of lysosomes. Co-localization of rhNaglu and Naglu-IGFII with lysosomes was visualized by confocal microscopy (FIG. 12).

Extensive internalization of Naglu-IGFII was observed after 4 hours of incubation of the protein with the cells, co-localization of Naglu-IGFII with lysosomes was demonstrated. Contrarily, rhNaglu failed to show internalization in the same time frame, and no co-localization with the lysosomes was observed. This result further provided the evidence that Naglu-IGFII was internalized into cells and transported to the correct cellular compartment, the lysosomes. The half life of internalized Naglu-IGFII in Sanfilippo B patient fibroblast cells was determined to be 1.5 days (data not shown).

Example 3: In Vivo Studies in Mouse Models

Wild Type (Wt) Cannulated Rat

In addition to the Sanfilippo B mouse model, the wt cannulated rat, a non-deficient animal model, was also used for molecule screening in vivo. The wt cannulated rats had surgically implanted cannula at the upper lumber and lower thoracic region of the spinal cord, and a single injection of 35 ul to the CSF was done through the cannula. The criteria assessed for molecule screening using this animal model were Naglu activity assay and immunohistochemistry of the brain and spinal cord.

Sanfilippo B Mouse Model

Figure 13:
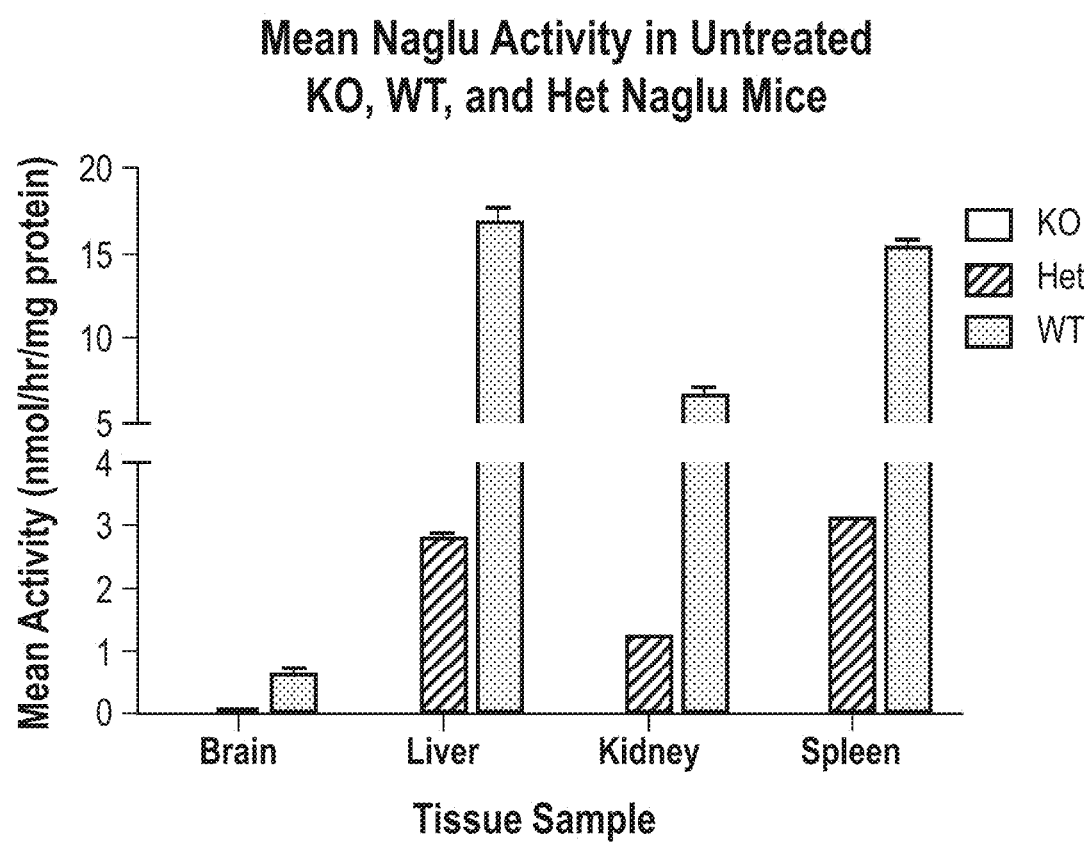
FIG. 13.

The mouse model of Sanfilippo B (Naglu−/− mouse, Sanfilippo BSanfilippo B mouse) was generated by E. Neufeld and colleague (Li H H, et al., PNAS 96(25):14505-14510; 1999). The exon 6 of the mouse's Naglu gene is disrupted by insertion of a selection marker, neomycin resistant gene. The resulting homozygote Naglu−/− mouse are completely Naglu deficient (FIG. 13), and have total GAG accumulation in liver and kidney. Despite the total deficiency of Naglu, these mice are generally healthy and have life span of 8-12 month. Changes of other lysosomal enzymes' expression happen at age around 5 months, these changes include compensatory increase of β-galactosidase, α-glucosidase, β-glucuronidase and β-hexosaminidase in liver and brain, elevation of α-L-iduronidase in liver but not in brain, and the reduction of neuraminidase in liver and brain. Death usually occurs as a result of urinary retention and urinary infection. The Sanfilippo B mouse model has been studied extensively in the literature to depict Sanfilippo B pathological changes. The phenotype related to CNS pathology of Naglu−/− mouse is reported to be hypo-activity at the age 4.5 month, but hyperactivity at other ages has also been observed.

The neuro-pathological changes in Naglu−/− mouse are described as vacuoles and inclusion bodies in neurons, macrophages and epithelial cells as observed by EM (electron-microscopy). These pathological changes typically start at 33 days of age, and progressively worsen as animals get older. Activated astrocyte and microglial cells are also demonstrated by histo-pathological analysis. Biochemical analysis of two gangoliosides, GM2 and GM3, showed 5 fold and 9 fold increase the brain. (Since GM2 and GM3 are not direct substrates of Naglu, and it could be challenging to demonstrate significant reduction after ERT for short period of time, they were not used as end biomarkers for POC).

Biochemical analysis was done by measurement of Naglu enzyme activities and GAG levels, histological analysis was done by anti-human Naglu antibody, anti-LAMP-1 antibody, anti-Iba-1 antibody and anti-GFAP antibody immunohistochemistry. The anti-human Naglu antibody used for this study was a mouse monoclonal antibody that doesn't bind endogenous murine Naglu in wt mouse or the mutated Naglu in Sanfilippo B mouse. LAMP-1 immunostaining used an antibody binds to lysosomal membrane protein, lysosomal associated membrane protein-1. Iba-1 staining used an antibody binds to ionized calcium-binding adaptor protein that is specific for microglial and macrophage cells. GFAP staining used an antibody that binds to glial fibrillary acidic protein which is specific for astrocytes.

In Vivo Biological Activity Screening by Intracranial (IC) Injection into Sanfilippo B Mouse The objective of this study was to evaluate the biological activity of Naglu enzymes in vivo. In this study, proteins were administered through IC injection into the brain of Sanfilippo B mouse. The age of Sanfilippo B mice for the study was closely matched to be at 8 weeks of age. The IC injection route offered the best case scenario to evaluate the efficacy of the molecules. Naglu proteins were assessed by the ability to be taken up into neuronal cells and to reduce lysosomal storage Immunohistochemistry was used to assess biodistribution. And lysosomal storage was characterized by the number and the size of positive staining using LAMP-1 immunostaining.

Figure 14:
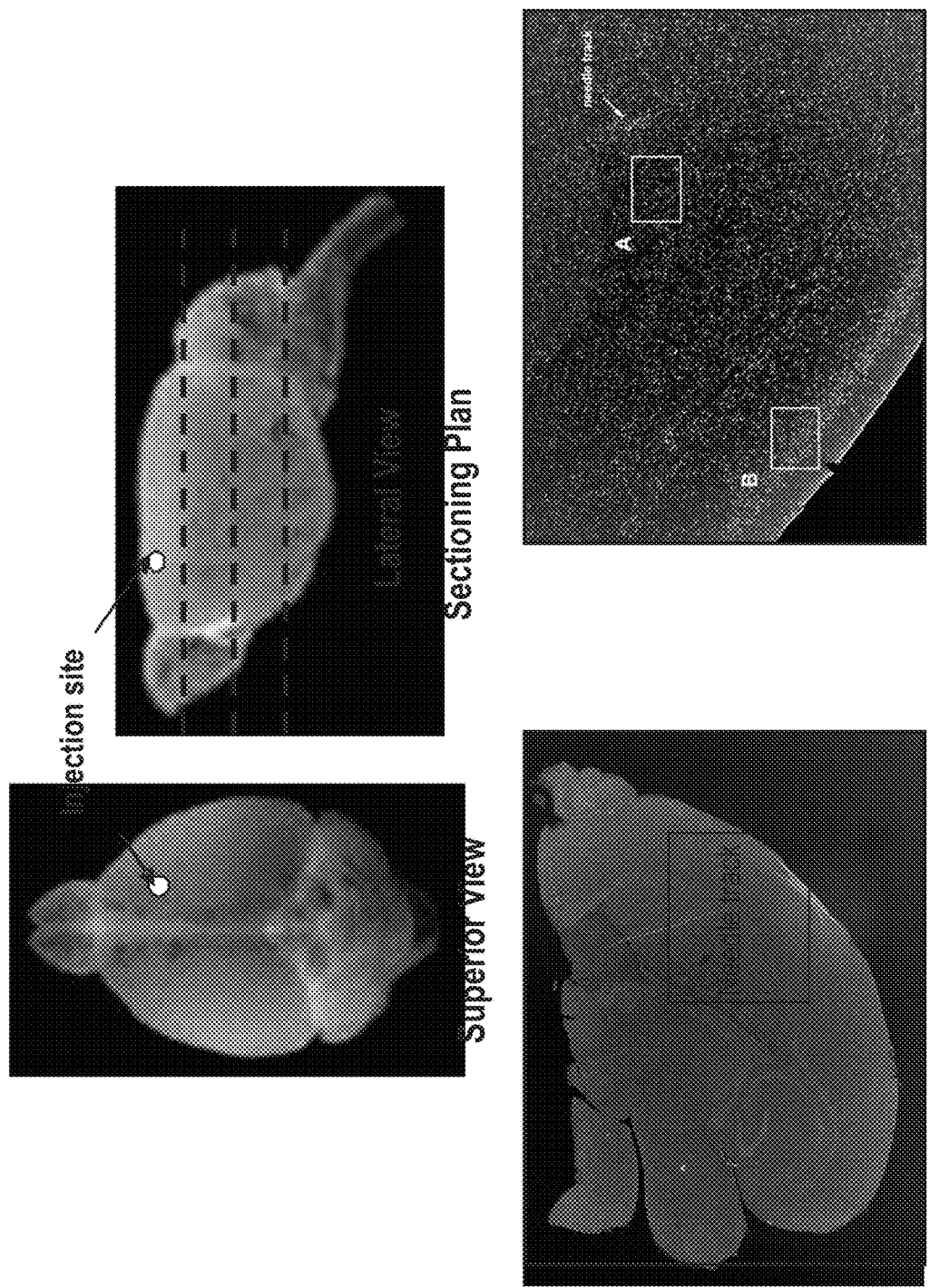
FIG. 14.
Figure 15:
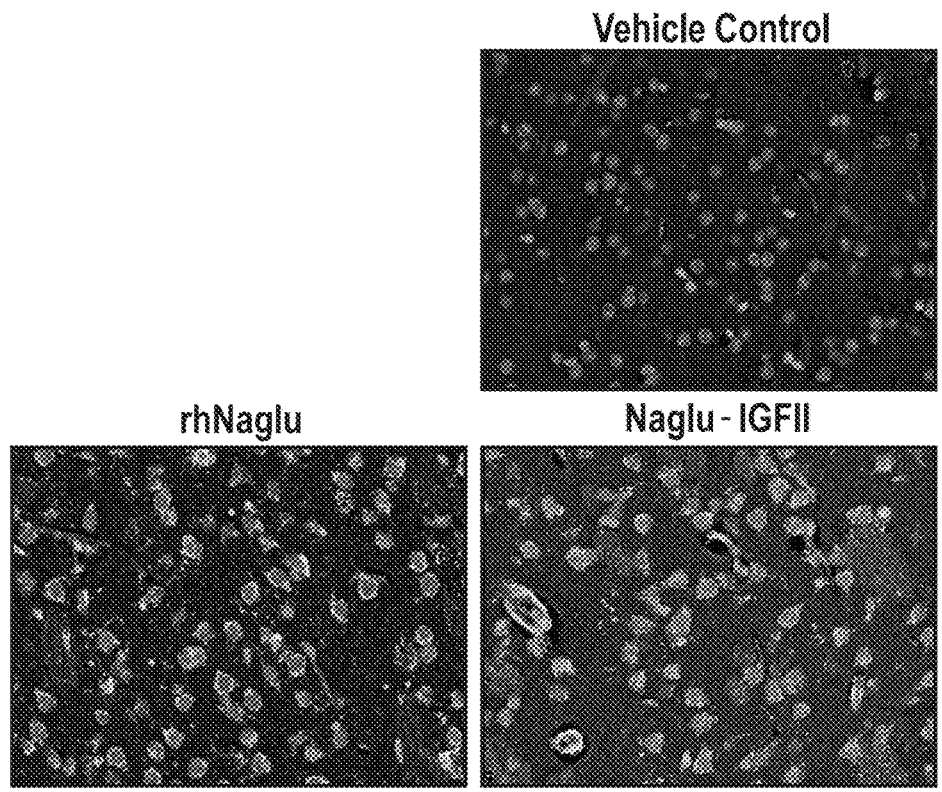
FIG. 15.
Figure 16:
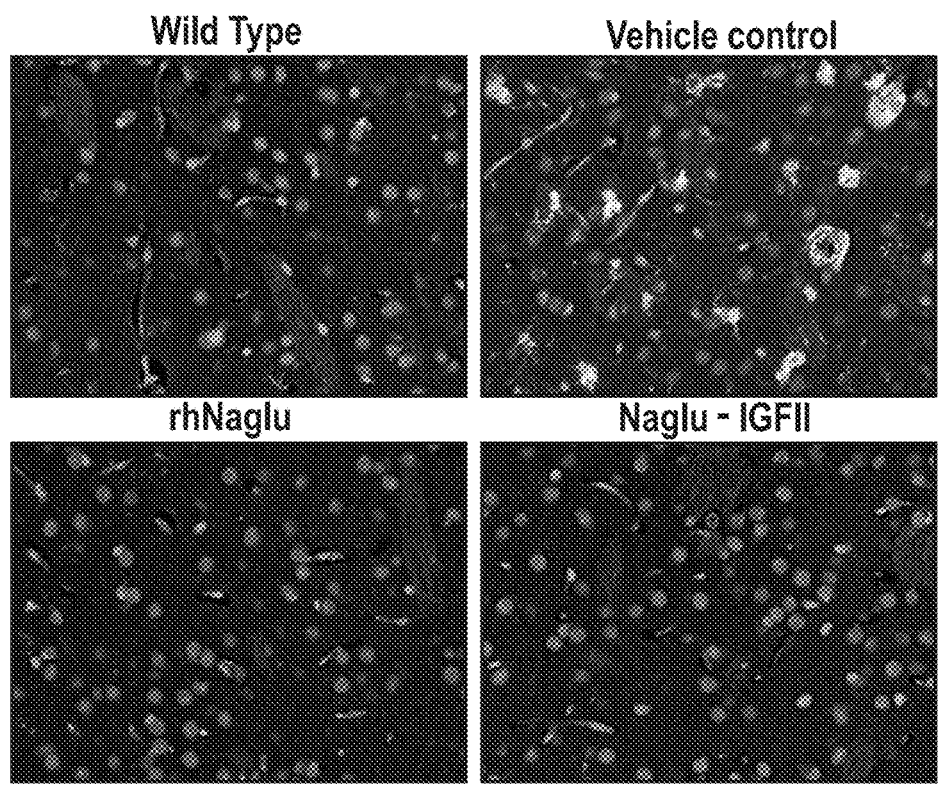
FIG. 16.

IC injection was done by direct injection through the skull of the Sanfilippo B mouse into the right cerebrum cortex. Two microliters, or 35 μg of Naglu protein was injected into each animal. Sacrifices of the animals took place 7-days after injection. The time of sacrifice was pre-determined in a pilot study where sacrifices of the animal took place 3, 7, and 14 day after injection. From the pilot study, it was determined that 7 days post injection is the optimum time for immunohistochemical study. Brain sections were cut transversally (FIG. 14), and Naglu and Lamp-1 immunostaining were performed. Cellular uptake into both the neurons and the glial cells in rhNaglu and Naglu-IGFII treated Sanfilippo B mouse was demonstrated by immunohistochemistry using an anti-human Naglu antibody (FIGS. 14-16). There was no significant difference between rhNaglu and Naglu-IGFII treated Sanfilippo B mouse in regards to the cellular uptake was observed. Additionally, LAMP-1 immunostaining of the brain tissue of both the rhNaglu and the Naglu-IGFII treated mouse indicates significant level of reduction of lysosomal storage. The level of lysosomal storage reduction in both rhNaglu and Naglu-IGFII treated groups was almost at the same level of normal wt mouse.

Reduction of lysosomal storage was also observed in Naglu-TAT, Naglu-Kif and PerT-Naglu tested Sanfilippo B mice after IC injection (data not shown). This study demonstrated the in vivo biological activity of all of the variants of Naglu.

In a separate study, Naglu-deficient mice were IT-administered a vehicle or alternatively one, two or three weekly doses of a recombinant Naglu-IgF-II fusion protein construct (Naglu) in PBS. An untreated wild-type group of mice served as an untreated wild-type control and were administered a vehicle without Naglu. Mice were sacrificed after 24 hours following the final injection, followed by tissue preparation for immunohistochemistry (IHC) and histopathological analysis.

Figure 17A:
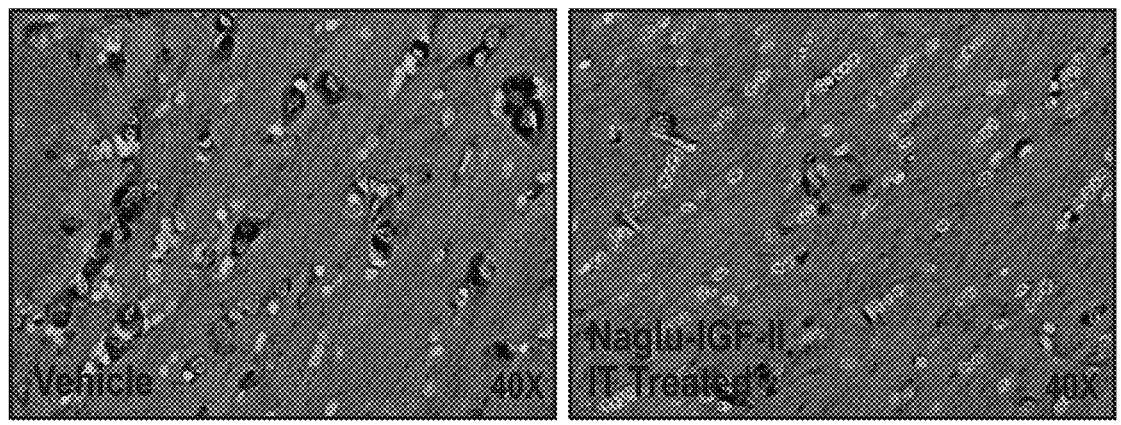
FIGS. 17A and 17B.
Figure 17B:
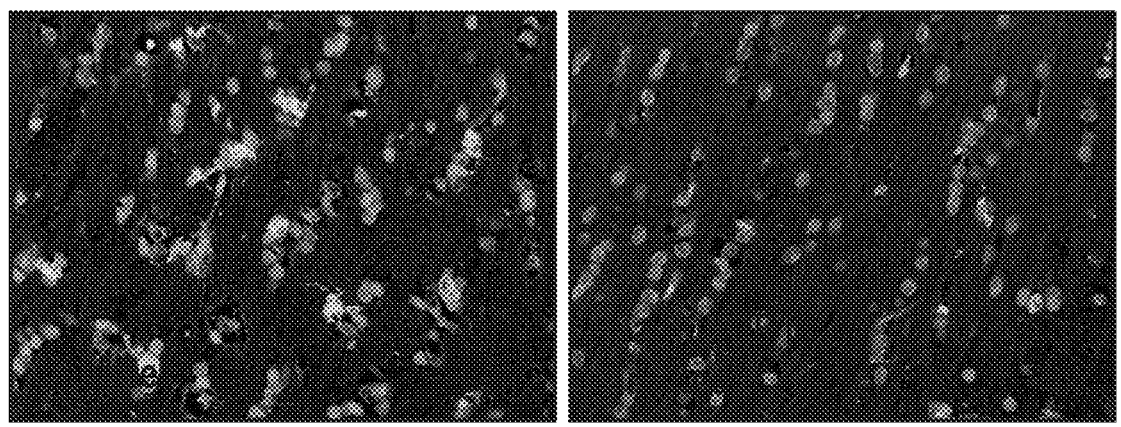

Distribution of Naglu to the brain tissues of the Naglu-deficient mice was evident following IT-administration of the recombinant Naglu. As illustrated in FIG. 17A, IT-administration of the recombinant Naglu to the Naglu-deficient mice resulted in the widespread reduction of cellular vacuolation in the white matter tissues compared to Naglu-deficient mice which were IT-administered the vehicle. Similarly, and as illustrated in FIG. 17B, morphometrical analysis revealed a marked reduction in LAMP1 immunostaining in the white matter tissues of the treated mice relative to the untreated Naglu-deficient mice, thereby reflecting an improvement in disease pathology.

Figure 18A:
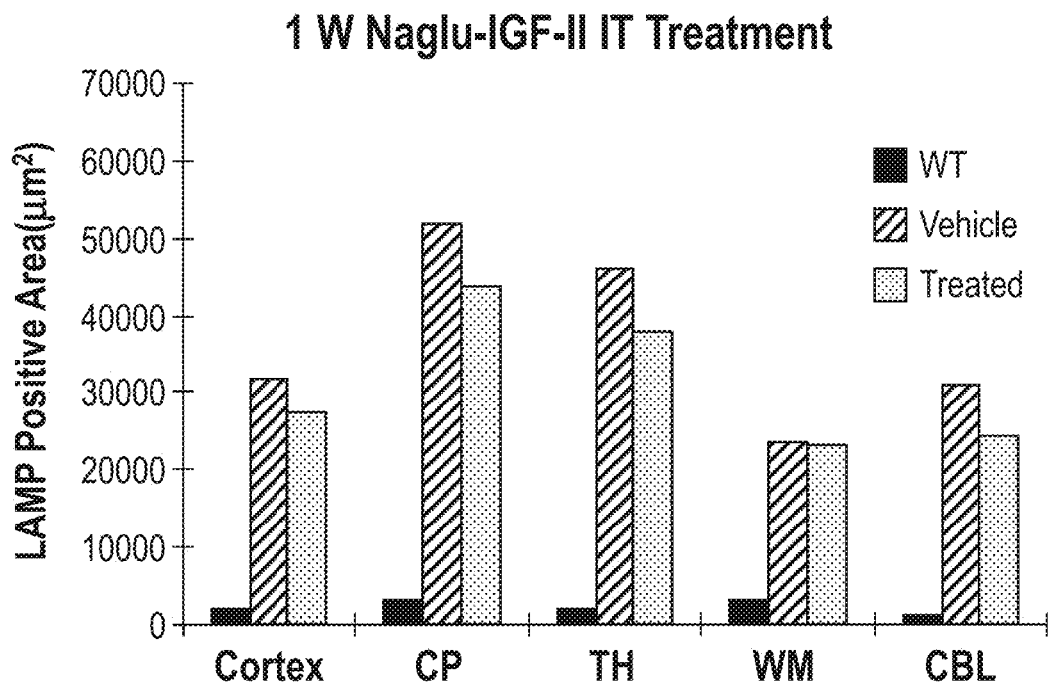
FIGS. 18A and 18B.
Figure 18B:
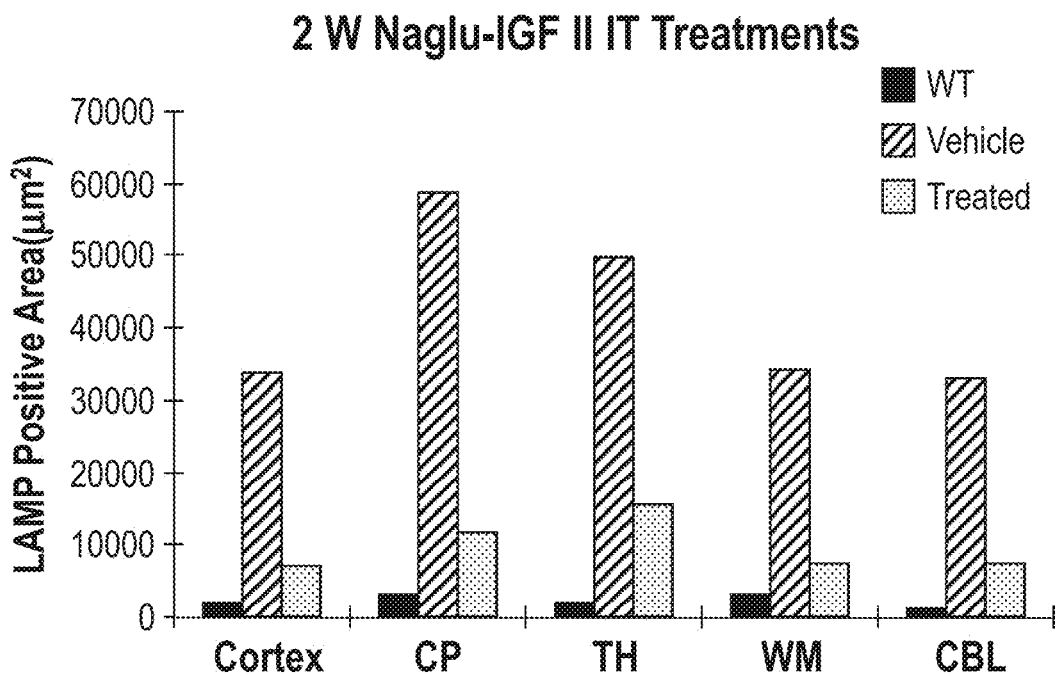

As shown in FIGS. 18A-18B, in each area of brain tissue evaluated (the cortex, caudate nucleus and putamen (CP), thalamus (TH), cerebellum (CBL) and white matter (WM)) the LAMP-positive area was reduced in the Naglu-treated mice relative to the untreated Naglu-deficient control mice, and approached the LAMP-positive area of the wild-type mice. Particularly notable is that the LAMP-positive areas in each area of brain tissue analyzed were further reduced following the IT-administration of two or three doses (FIG. 18B) relative to a single dose (FIG. 18A) of Naglu.

These results also confirm that IT-administered Naglu is capable of altering progression of lysosomal storage diseases such as Sanfilippo syndrome type B in the Naglu-deficient mouse model, further confirming the ability of IT-administered enzymes such as Naglu to treat the CNS manifestations associated with lysosomal storage diseases, such as Sanfilippo syndrome type B.

Molecule Screening by Intrathecal (IT) Injection into Wt Cannulated Rat

This study directly mimics a port-mediated approach for drug administration. Naglu protein was administered via IT injections into wt cannulated rats to determine biodistribution into the parenchyma of the brain.

Figure 19:
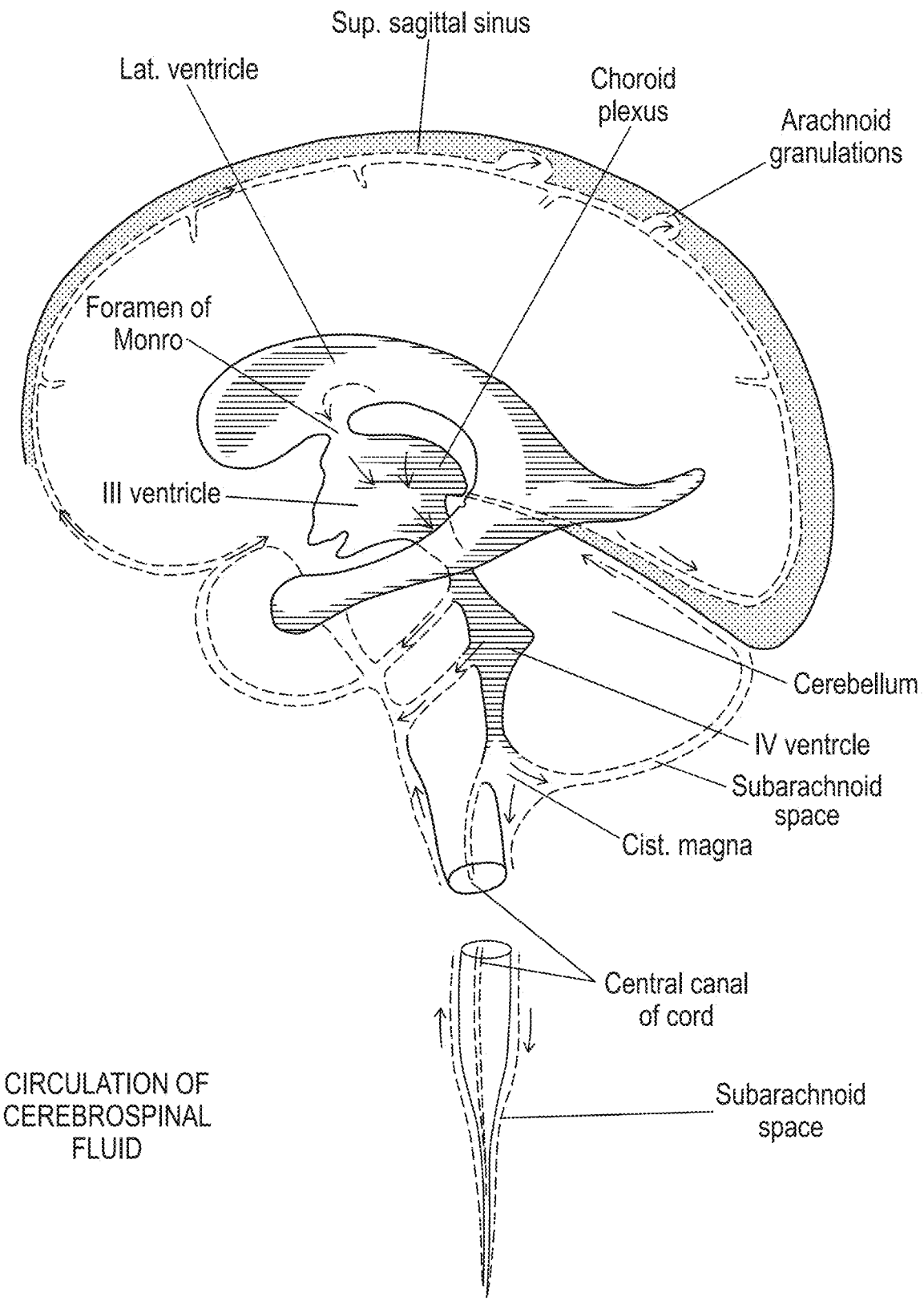
FIG. 19.

The cannula in these animals was placed in the upper lumbar and lower thoracic portion of the spinal cord (FIG. 19). Animals were injected with 35 µl, or 385 µg of rhNaglu, Naglu-TAT, Naglu-IGFII and PerT-Naglu, through the cannula (due to the solubility limitation, Naglu Kif was injected with only 38.5 ug, which is 10 fold less than the rest of the Naglu). Sacrifices happened 4 hr and 24 hr after injections.

Figure 20:
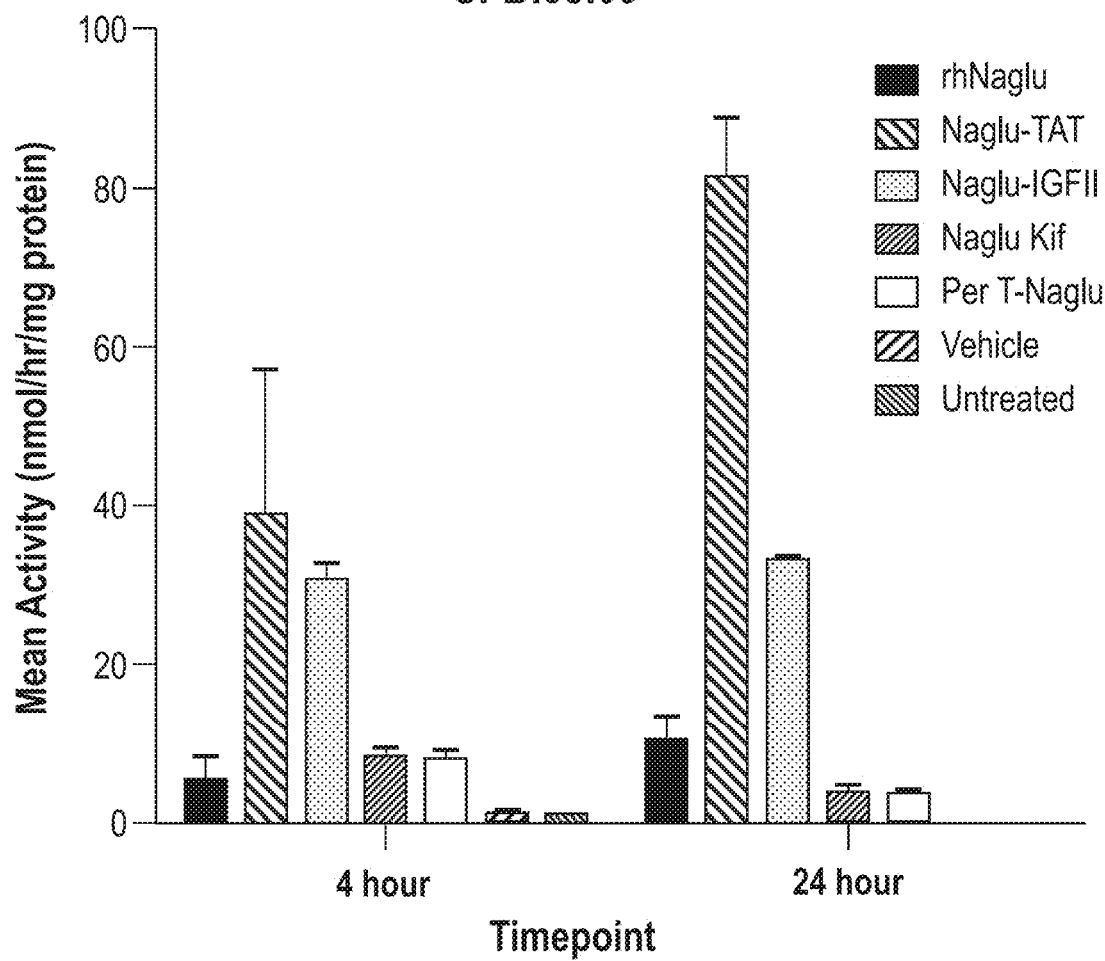
FIG. 20.

Brain and spinal cord tissues were collected and measured by the Naglu activity assay. In the brain of treated animals, Naglu-TAT and Naglu-IGFII treated animals exhibited higher activity than the rhNaglu and all other Naglu variants treated animals (FIG. 20). As a general trend, the Naglu activity was significantly higher in the spinal cord than in the brain for all treated animals (data not shown). This phenomenon may indicate that proteins were taken up more at the site closer to the IT injection.

Figure 21:
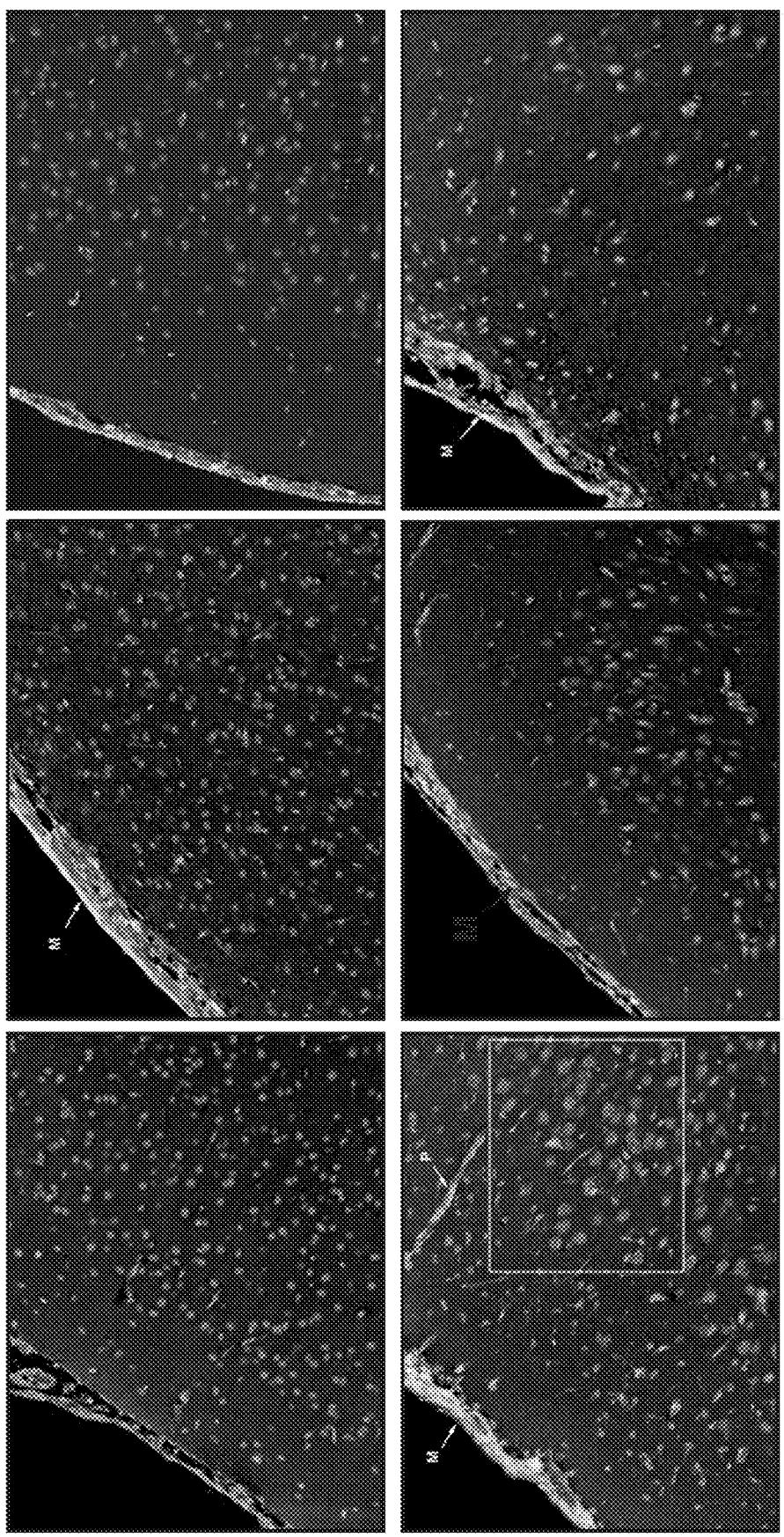
FIG. 21.
Figure 22:
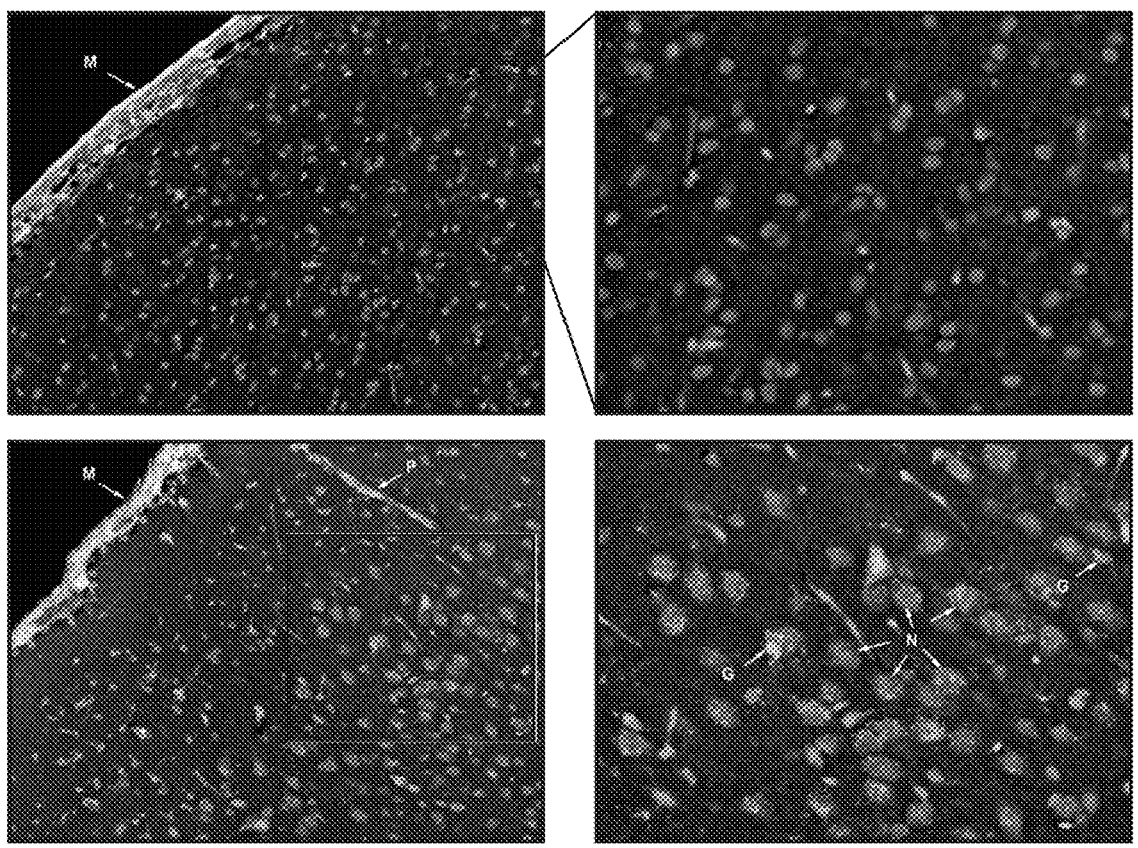
FIG. 22.

Immunohistochemistry analysis indicated that the biodistribution of the Naglu-IGFII treated group was more extensive in the brain than all other Naglu variants treated group 24 hr after IT injections (FIGS. 21 and 22). In the rhNaglu treated animals the protein was observed in the meninges of the brain only. In the spinal cord section, IHC indicated some cellular uptake of rhNaglu in the neurons of the grey matter, but to a much lesser extent than Naglu-IGFII uptake in the neurons of spinal cord (data not shown).

In Naglu-TAT IT injected group, even though highest Naglu activity was observed in brain tissue by biochemical analysis, but IHC failed to indicate any Naglu-TAT penetration into the parenchyma of the brain, other than remaining on the meninges. Besides from Naglu-IGFII, all of the other Naglu variants failed to show biodistribution beyond the meninges, a strong testimony of the dependency on M6P/IGFII receptors for the cellular uptake of Naglu in the brain after IT injection. This study pointed to Naglu-IGFII as the lead molecule for drug development for Sanfilippo B.

Example 4: Proof of Concept Study Using Naglu-IGFII

Experimental Design

The proof of concept study was designed to show both biodistribution and the reversal of lysosomal storage after IT injection of Naglu-IGFII in Sanfilippo B mouse. For this study, three groups of Sanfilippo B mice at 8 weeks of age were treated with an IT injection of Naglu-IGFII. Each IT injection constituted a 10 ul volume or 260 ug of Naglu-IGFII. There were three treated groups, 1× injection, 2× injection and 3× injections group. For the 1× injection group, a single dose of protein was administered at day 0. Animals were sacrificed 24 hr after injection. For the 2× injection group, two IT injections were administered at day 0 and day 7, and animals were sacrificed 24 hr after the last injection. For the 3× injection group, IT injections were administrated at day 0, day 7 and day 14, and animals were sacrificed 24 hr after the last injection. Three groups of vehicle treated mouse were also included. For the vehicle control groups, Sanfilippo B mice were injected with vehicle at the same time interval as the treated groups and sacrificed the same way as the treated groups.

Figure 23:
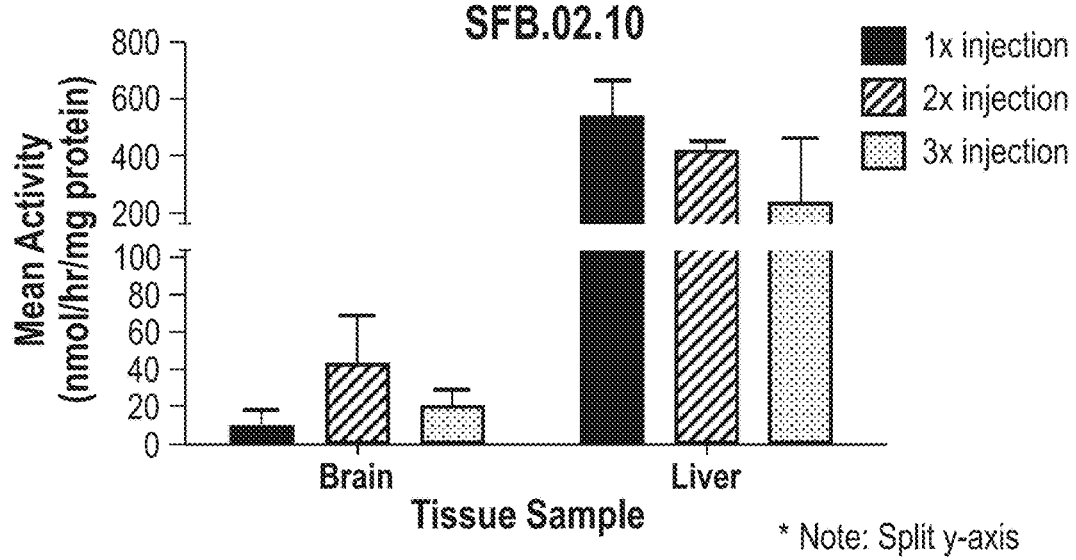
FIG. 23.
Figure 24:
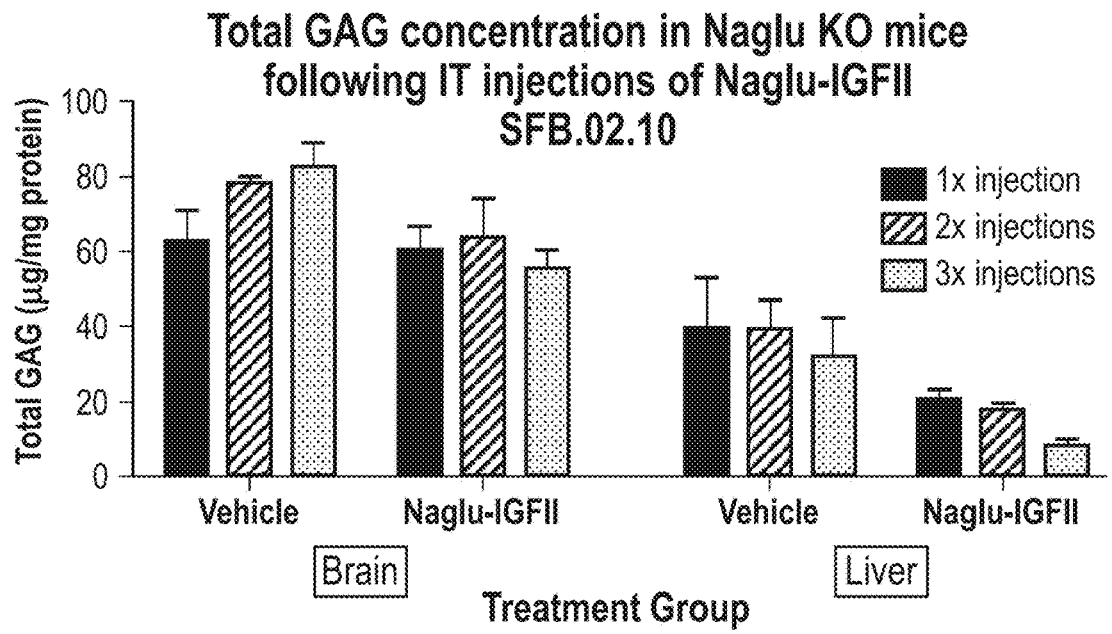
FIG. 24.

Both biochemical and histological analyses were applied to evaluate the outcome of the study. The biochemical analyses include a Naglu activity assay to measure the amount of enzymes in the tissue and a total GAG assay to evaluate the reduction of lysosomal storage. Liver and brain were the two subjected tissue for biochemical analyses (FIGS. 23 and 24). The histological analyses include H&E staining of the tissues for morphological evaluation (data not shown), and immunohistochemical staining with anti-human Naglu antibody, LAMP, Iba and GFAP (data for Iba and GFAP staining not shown).

The anti-human Naglu antibody used for this study was a mouse monoclonal antibody that doesn't bind endogenous murine Naglu in wt mouse or the mutated Naglu in Sanfilippo B mouse. LAMP-1 immunostaining used an antibody binds to lysosomal associated membrane protein. Iba-1 staining used an antibody binds to ionized calcium-binding adaptor protein that is specific for microglial and macrophage cells. GFAP staining used an antibody that binds to glial fibrillary acidic protein which is specific for astrocytes.

Figure 25:
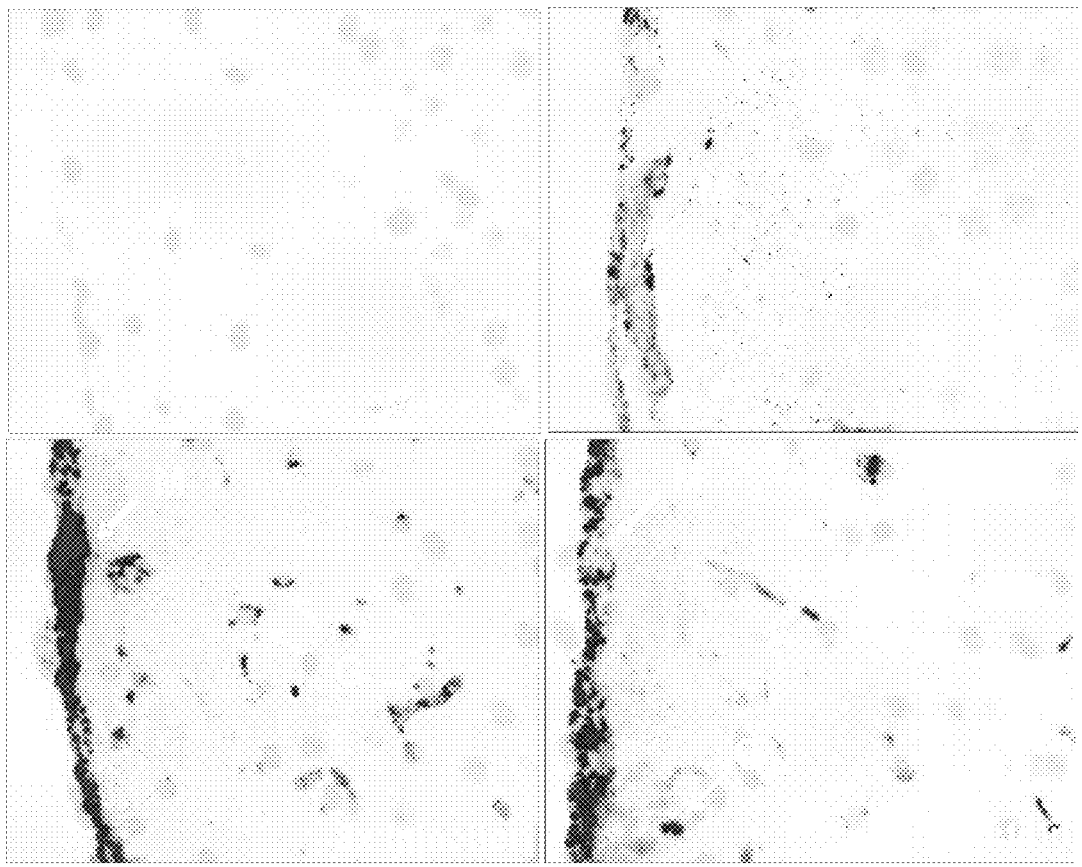
FIG. 25.
Figure 26:
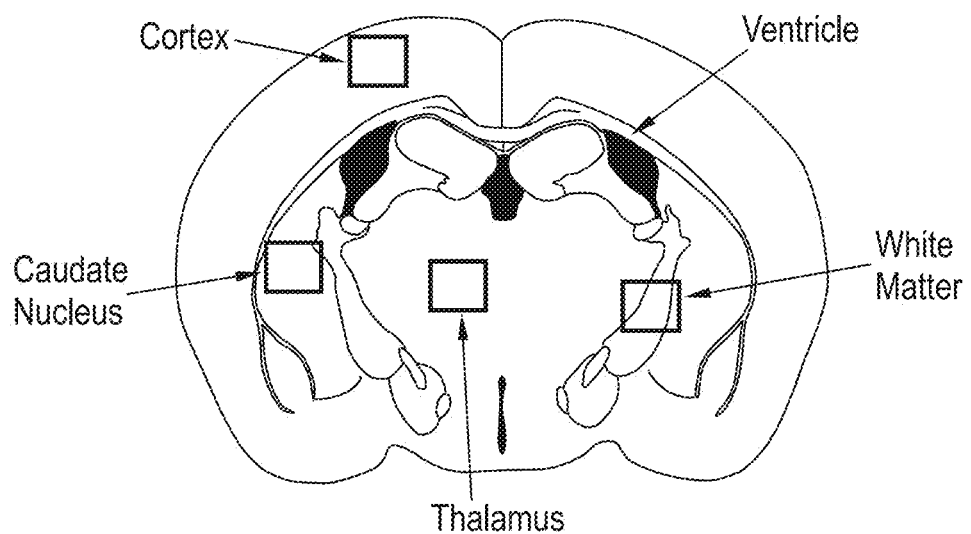
FIG. 26.

Representative microscopic pictures of Naglu immunofluorescence are shown in FIG. 25. Exemplary areas of the brain are depicted in FIG. 26. Even though Naglu-IGFII was detected into the cerebral cortex which is closer to the meninges, it was not found in the subcortical region such as the caudate nucleus, the thalamus and the white matter (data not shown). Since the immunostaining of LAMP-1, Iba-1 and GFAP of the same subcortical areas did demonstrate reversal of lysosomal storage, it was believed that the negative immunostaining of Naglu in the deep brain areas was probably due to the sensitivity of the Naglu immunofluorescence.

Representative microscopic pictures of Lamp-1 immunostaining are shown in FIGS. 27-31. To demonstrate the extent of protein distribution and efficacy, cerebral cortex and subcortical regions, such as caudate nucleus, thalamus and white matter, and cerebellar cortex were selected for immunohistological analysis. The result from Iba-1 and GFAP immunostaining (data not shown) indicated that what was seen in the LAMP-1 immunostaining was the combined effect of the changes of microglial cells and astrocytes, the two cell types that were reported to be affected in Sanfilippo B mouse model (Li 2002, Ohmi 2002) in addition to neurons. Due to technical limitations, LAMP-1 immunostaining was not able to reveal lysosomal storage in neurons. To best observe the lysosomal accumulation in neurons, such vacuoles and inclusions, electron microscopy is usually utilized (EM was not included in current study).

It will be appreciated that the identification of cell types was limited to neurons and glial cells. The neurons were typically identified by the relatively large and pale nucleus that contains one or more densely stained nucleoli, and the frequently detectable cytoplasm. The glial cells were generally identified by the small dense nucleus and the inconspicuous cytoplasm. The distinction between the different types of glial cells, such as astrocytes, microglial cells, ependymal cells and oligodendrocytes, is typically best done by staining with cell type specific markers.

In addition to the reduction of lysosomal storage exhibited by the LAMP-1 immunostaining, the Iba-1 immunostaining indicated the reduction of cell size and number of processes in microgial cells, and GFAP immunostaining indicated the reduction of cell size and length/number of processes in astrocytes, in the cerebral cortex, caudate nucleate, thalamus, white matter and cerebellum after IT injections of Naglu-IGFII (data not shown). Furthermore, histopathological analysis by H&E staining (hematoxylin and eosin) of the brain tissues from the same areas as examined for immunohistochemistry, demonstrated the reduction of vacuoles in glial cell after 3× IT injection of Naglu-IGFII. All of the result mentioned above also suggested the dose-related effect of Naglu-IGFII IT injections.

The biochemical analyses of Sanfilippo B mice after IT injection of Naglu-IGFII detected Naglu activity in the brain and liver. Efficacy of the Naglu-IGFII was demonstrated by total GAG reduction in the brain and liver Immunohistochemistry demonstrated the biodistribution of Naglu-IGFII in the parenchyma of the brain. Immunostaining of LAMP-1, Iba-1, GFAP and histopathological analysis by H&E staining exhibited reduction of lysosomal storage, the reduction of size and process by microglial and astrocytes in not only the cerebral cortical area of the brain, but also in the subcortical areas, white matter and cerebellar cortex of the brain.

Conclusions

Among other things, it has been demonstrated that the fusion protein, Naglu-IGFII, exhibited enzymatic activity in vitro toward a substrate that has similar structure to the native substrate of Naglu. In vitro cellular uptake study demonstrated that the molecule was taken up to cells by the M6P/IGFII receptor in a manner that was independent of M6P glycosylation. Internalized Naglu-IGFII was shown to co-localize with lysosomes. Naglu-IGFII was shown to reduce lysosomal storage in vivo after IC injection into the Sanfilippo B mouse. In comparison to rhNaglu and other Naglu fusions and modifications, Naglu-IGFII surpassed them all in penetrating into the parenchyma of the brain of wt cannulated rat after IT injection. Finally, IT injection of the Naglu-IGFII fusion into Sanfilippo B mice demonstrated extensive distribution well beyond the meninges, and observed reversal of lysosomal storage in the cerebral cortex as well as in the subcortical regions. Taken together, these data indicate that Naglu-IGFII is a candidate drug for treatment of Sanfilippo B disease.

Example 5: Toxicity, Pharmacokinetics (PK) and Tissue Biodistribution Studies of Naglu-IGFII Proof of Concept Studies in Mouse Three groups (n=3) of Naglu (−/−) mice were injected with 10 uL containing 260 ug of Naglu-IGFII given as a single bolus IT lumbar injection. The 260 ug dose translates into a 520 mg/kg brain weight dose (mouse brain=0.0005 kg). One group was injected at Day 0 and sacrificed 24 hr post injection. A second group was injected on Days 0 and 7, and sacrificed 24 hr after the last injection. The third group was injected on Days 0, 7, and 14, and sacrificed 24 hr after the last injection. Each Naglu-IGFII-dosed group was paired with a vehicle control group in order to control for age/disease severity.

Naglu enzyme activity in the brain and the liver was similar for the three Naglu-IGFII-dosed groups. Comparing rhNaglu enzyme activity in the liver to brain, more than 10-fold rhNaglu enzyme activity was found in the liver. It was contemplated that since levels of rhNAGLU enzyme activity were comparable in the brain and liver after 1-, 3-, and 6-months of dosing in the pivotal toxicity studies in rats and juvenile monkeys, some portion of rhNaglu dose given to the Naglu (−/−) mice may not have been delivered IT, but rather systemically. Nevertheless, the total GAG level in the brain showed a statistically-significant reduction (p<0.05) after 3 IT injections. A dose-related trend for total GAG level reduction was seen in the livers, which was statistically-significant (p<0.05) in the groups receiving 2 or 3 doses.

The biodistribution of Naglu-IGFII after IT injection was observed well beyond meninges into the parenchyma of the brain, but deep subcortical regions were negative for anti-Naglu antibody immunostaining. A reduction of lysosomal activity by lysosomal-associated membrane protein (LAMP) immunostaining was observed in the groups given 2 or 3 doses only. Areas of lysosomal activity reduction included cerebral cortex and deep subcortical regions of caudate nucleus, thalamus, and white matter. Thus, the reduction of various immunostaining parameters in Naglu-IGFII-dosed animals suggested that therapeutic levels of NAGLU might be present despite the absence of anti-NAGLU immunostaining. An attenuated inflammatory response was evidenced by reduction of glial fibrillary acidic protein (GFAP) immunostaining of astrocytes and reduction of ionized calcium-binding adaptor molecule (Iba) staining of microglia/macrophages in groups given 2 or 3 doses only. Areas of analysis included cerebral cortex and deep subcortical regions of caudate nucleus, thalamus, and white matter.

Studies in Rat

The S-D rat was selected as the rodent species for toxicological evaluation of IT-administered Naglu-IGFII. As a result, sixteen rats (eight per sex) are dosed with recombinant Naglu-IGFII at the maximal feasible dose (MFD), and at approximately ¼ and ½ the MFD (low- and mid-dose levels, respectively) every 4 days for a total of 8 doses.

Single-dose PK/biodistribution study in S-D rats is performed to determine CSF and serum concentration, or tissue distribution, respectively, following IT-L administration to male and female animals.

Toxicology studies are designed to evaluate IT-L administration of Naglu-IGFII from a toxicology and safety pharmacology (neurologic, respiratory, and cardiovascular safety) perspective in both male and female animals. Toxicological evaluation in these studies includes clinical observations, body weights, food consumption, clinical pathology, appropriate safety pharmacology assessments (by physical examination or electrocardiography), gross tissue and microscopic evaluation. A limited number of CSF and serum samples are collected and analyzed for Naglu-IGFII, and for antibodies to the test article. Naglu-IGFII tissue distribution and subcellular localization are quantified by enzyme activity assay and immunohistochemistry, respectively. Additionally, selected studies include a recovery period to assess the reversibility, or potential delayed appearance, of any noted significant toxicological findings.

Studies in Monkeys

The cynomolgus monkey was been selected as the non-rodent species for toxicological evaluations of IT-administered Naglu-IGFII due to their genetic and anatomical similarity to humans and hence is thought to be the more relevant species. Given that the planned patient population for the Sanfilippo B clinical trials is pediatric, a chronic 6-month toxicology study in juvenile cynomolgus monkeys featuring intrathecal drug deliver device (IDDD) administration of Naglu-IGFII is performed. Juvenile cynomolgus monkeys are generally less than 1 year of age at initiation of study (approximately 7-9 months of age) and weigh between 900 g to 1,500 g at study initiation. The data obtained from a 1-month repeated-dose juvenile cynomolgus monkey toxicity study guide the dose level selection and design of the 6-month juvenile monkey study. The repeated-dose toxicology studies are designed to mimic the expected clinical route (IT-L bolus) and frequency of administration (every other week; EOW) over a period of 1 through 6 months.

As described above, toxicology studies are designed to evaluate IT-L administration of Naglu-IGFII from a toxicology and safety pharmacology (neurologic, respiratory, and cardiovascular safety) perspective in both male and female animals. Toxicological evaluation in these studies includes clinical observations, body weights, food consumption, clinical pathology, appropriate safety pharmacology assessments (by physical examination or electrocardiography), gross tissue and microscopic evaluation. A limited number of CSF and serum samples are collected and analyzed for Naglu-IGFII, and for antibodies to the test article. Naglu-IGFII tissue distribution and subcellular localization are quantified by enzyme activity assay and immunohistochemistry, respectively. Additionally, selected studies include a recovery period to assess the reversibility, or potential delayed appearance, of any noted significant toxicological findings.

Example 6. EOW Intrathecal Administration of Naglu-IGFII

This example was designed to determine the feasibility of IT-lumbar dosing EOW for 6 injections (3 month study) in the Naglu −/− mouse model. This dosing regimen may be more clinically relevant as compared to weekly dosing.

Eight week old Naglu −/− male and female mice were studied according to the following experimental design:

TABLE 10

Experimental Design for EOW IT Delivery of Naglu-IGFII

| Group | N | Treatment | Dose | Frequency | Sacrifice |
|---|---|---|---|---|---|
| A | 3 | Vehicle | N/A | IT injection EOW for 3 months (total of 6 injections) | 24 h after last injection |
| B | 6 | Naglu-IGFII | 60 mg/kg brain weight (30 ug) | IT injection EOW for 3 months (total last of 6 injections) | 24 h after injection |

Physiological studies, including Naglu activity assay on liver, brain and serum, anti-Naglu antibody assay on serum, and BCA assay on liver and brain, were performed. Histological studies, including Naglu IHC on brain, spinal cord and liver, and Lamp staining on brain and spinal cord, were performed.

Brain, spinal cord and liver were collected and fixed in 10% NBF. Five μm paraffin sections were prepared for histological staining Immunohistochemical (IHC) staining of Naglu was used to detect cellular uptake of the injected protein. H&E staining was used to observe morphological changes. LAMP, an indicator of lysosomal activity and disease state, GFAP and Iba-1, two CNS pathological markers for activated astrocytes and microglial cells, were used for histopathological improvement evaluation.

Figure 32:
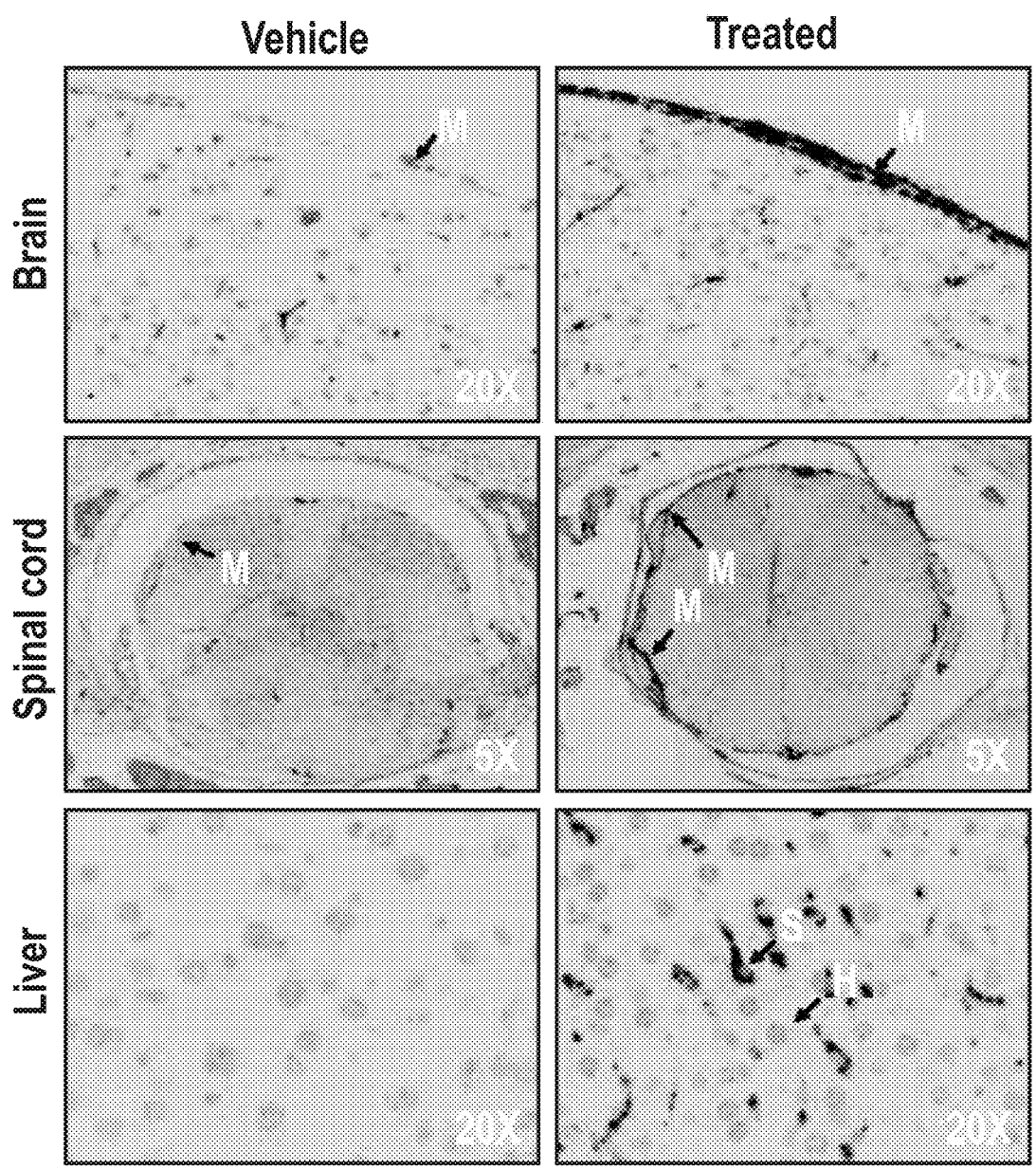
FIG. 32.

Naglu immunostaining of brain, spinal cord and liver of vehicle and Naglu-IGFII treated mice demonstrated that, in the brain and spinal cord, injected Naglu was detected in meninges (M) only by IHC and no Naglu positive staining was detected in any other regions (FIG. 32). In the liver, sinunoidal cells (S) were Naglu positive and no Naglu uptake was found in hepatocytes (H).

Figure 33:
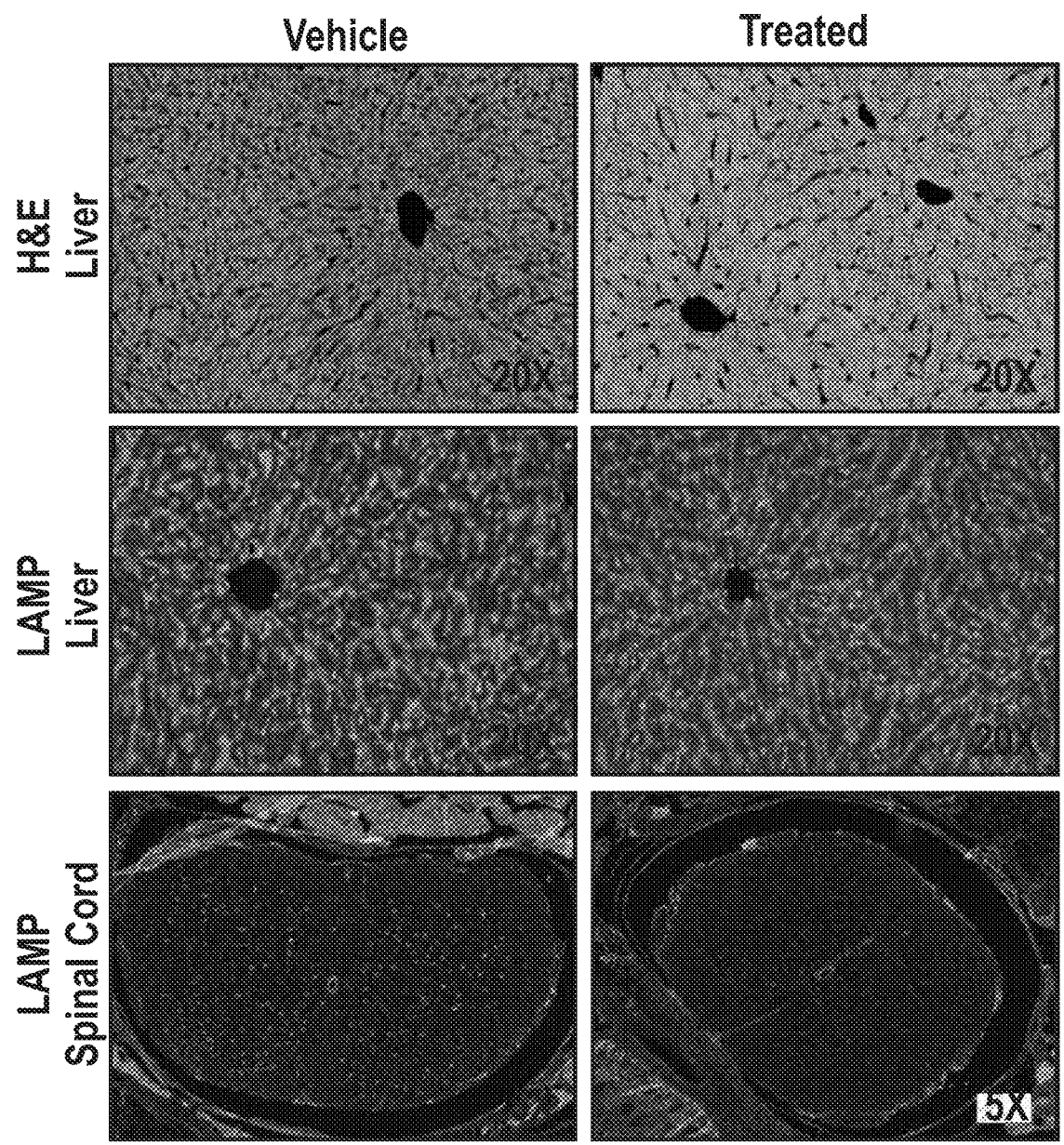
FIG. 33.
Figure 34A:
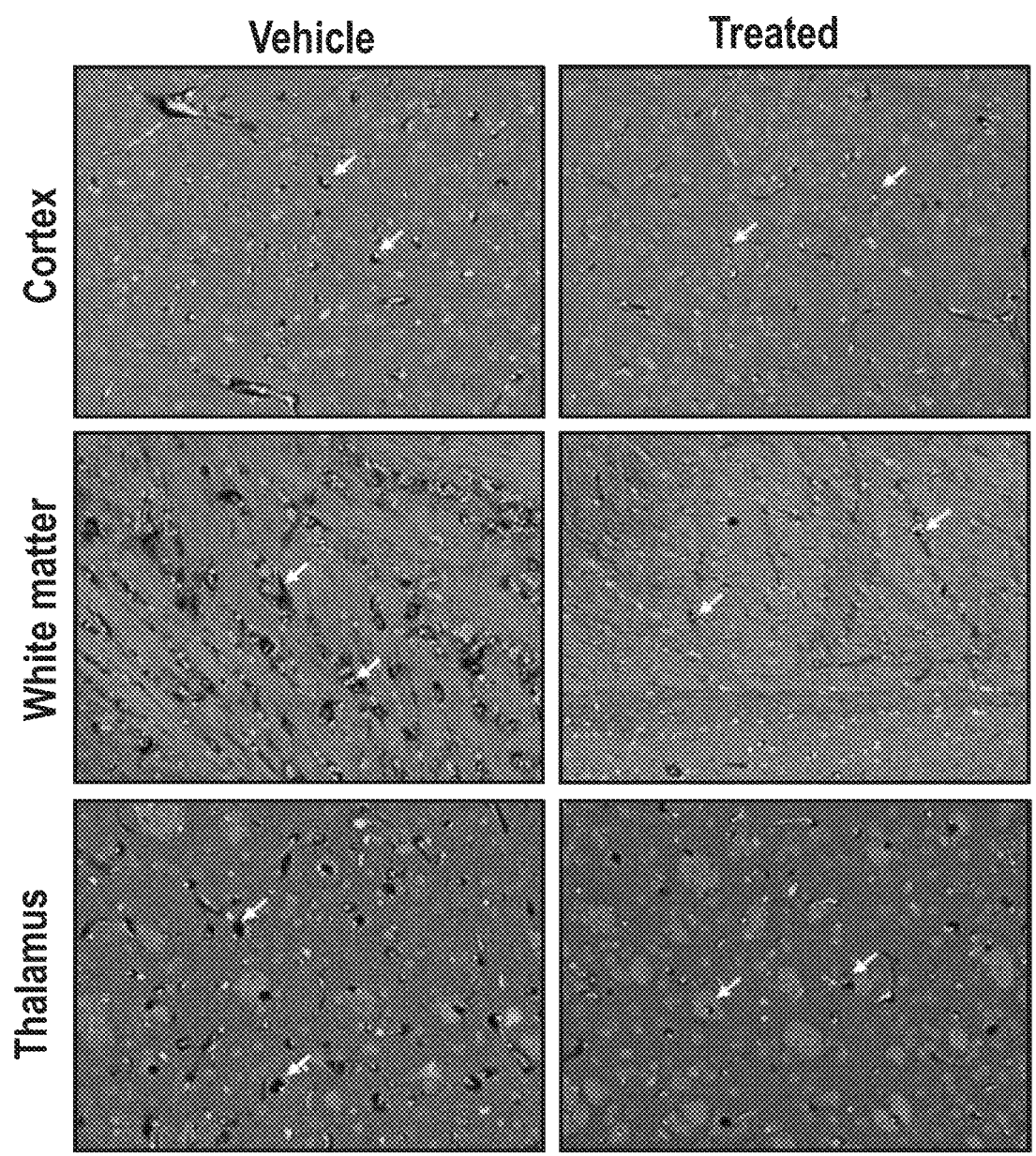
FIGS. 34A and 34B.
Figure 34B:
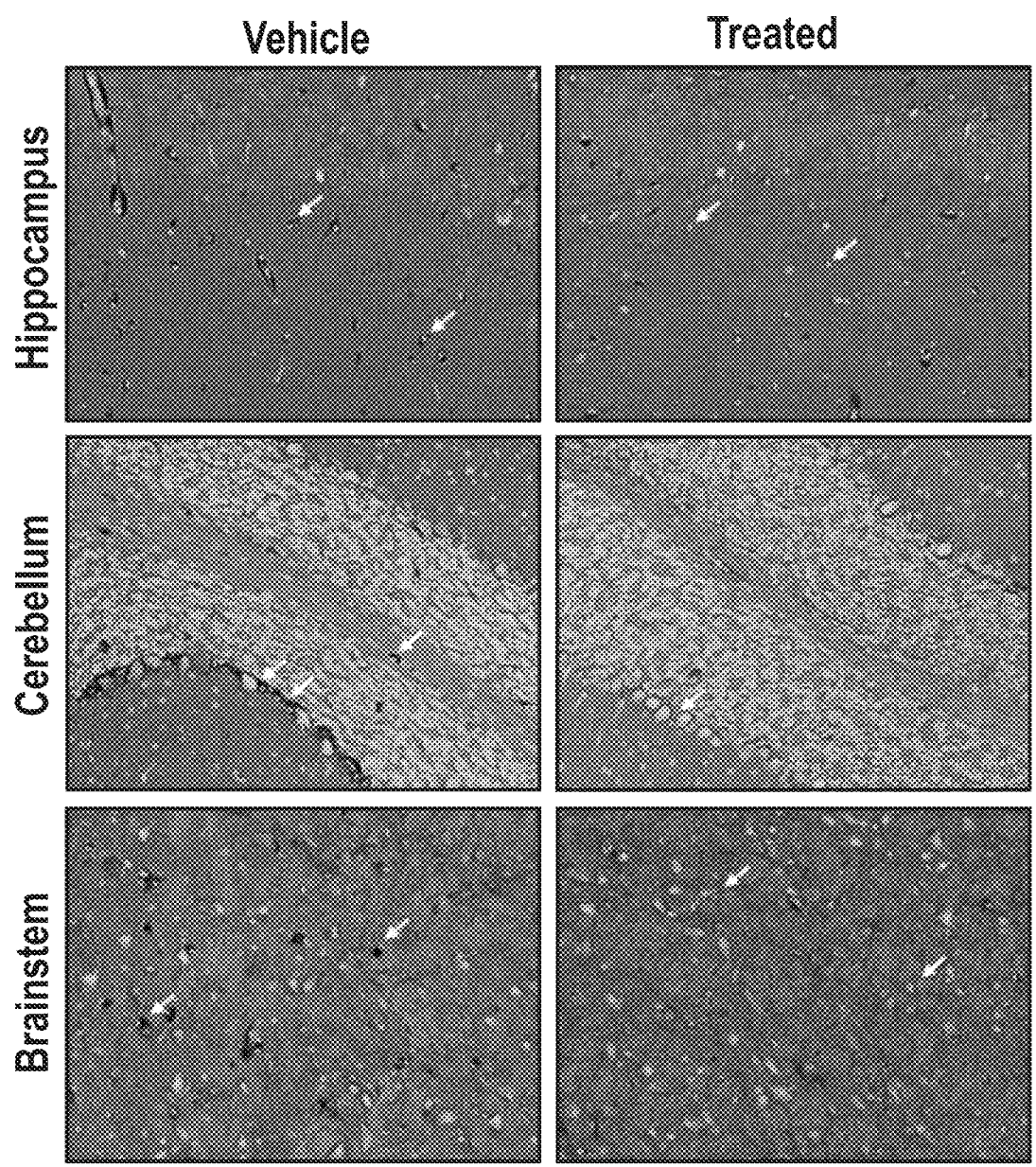

LAMP immunostaining and H & E staining of the liver and spinal cord of vehicle and Naglu-IGFII treated mice demonstrated that, compared with the vehicle animals, LAMP staining was decreased throughout in both livers and spinal cords treated with Naglu. H&E staining showed cellular vacuolation in hepatocytes was evidently reduced in the treated group compared with vehicle treated animals (FIGS. 33, 34A, and 34B).

H & E staining of the brain of vehicle and Naglu-IGFII treated mice demonstrated a morphology improvement in the brain after 6 every other week IT injection of Naglu-IGFII for 3 months. In the treated brain, the cellular vacuolation (arrows) in all examined regions decreased compared with the vehicle group (FIGS. 35A and 35B).

Figure 35A:
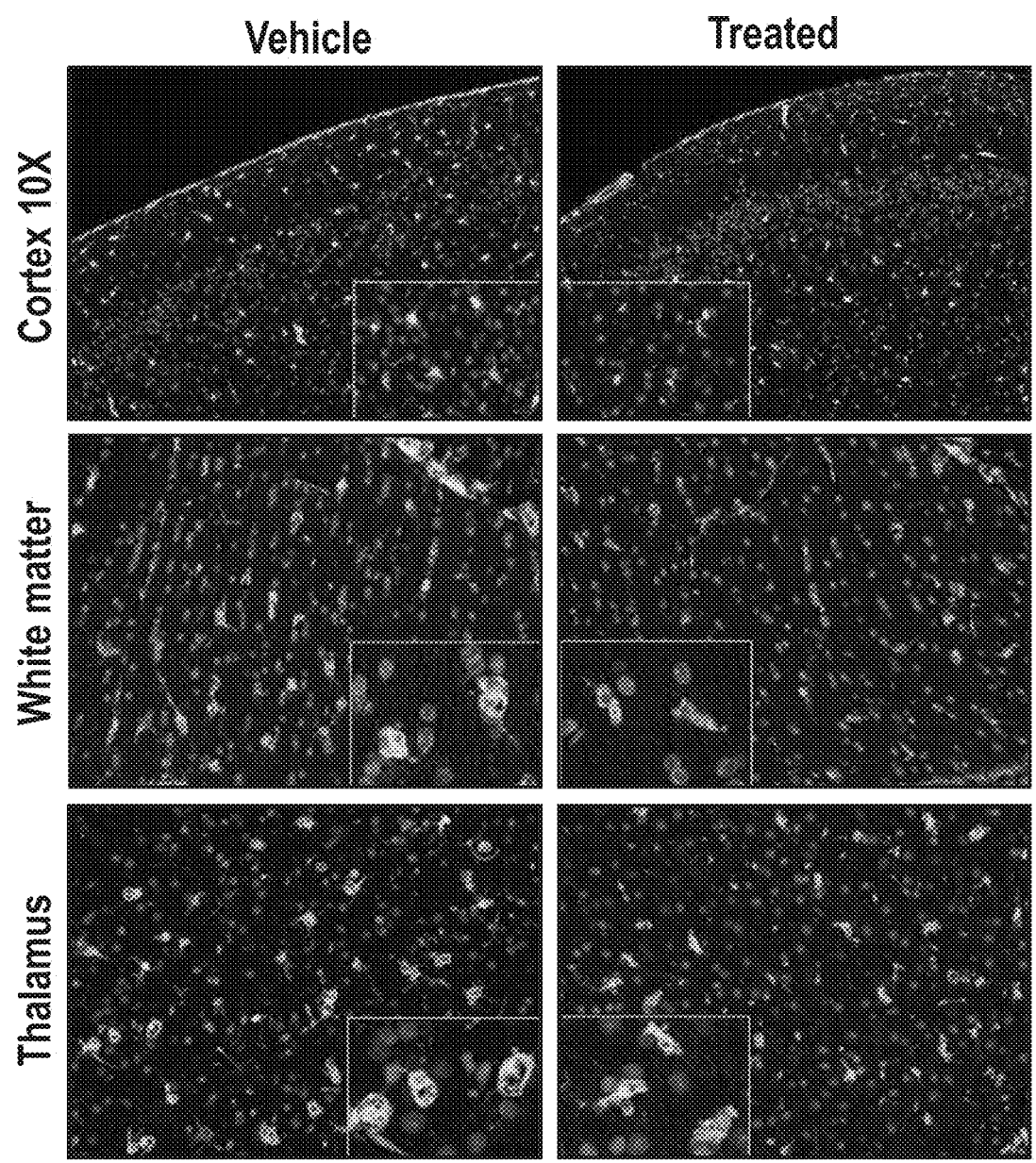
FIGS. 35A and 35B.
Figure 35B:
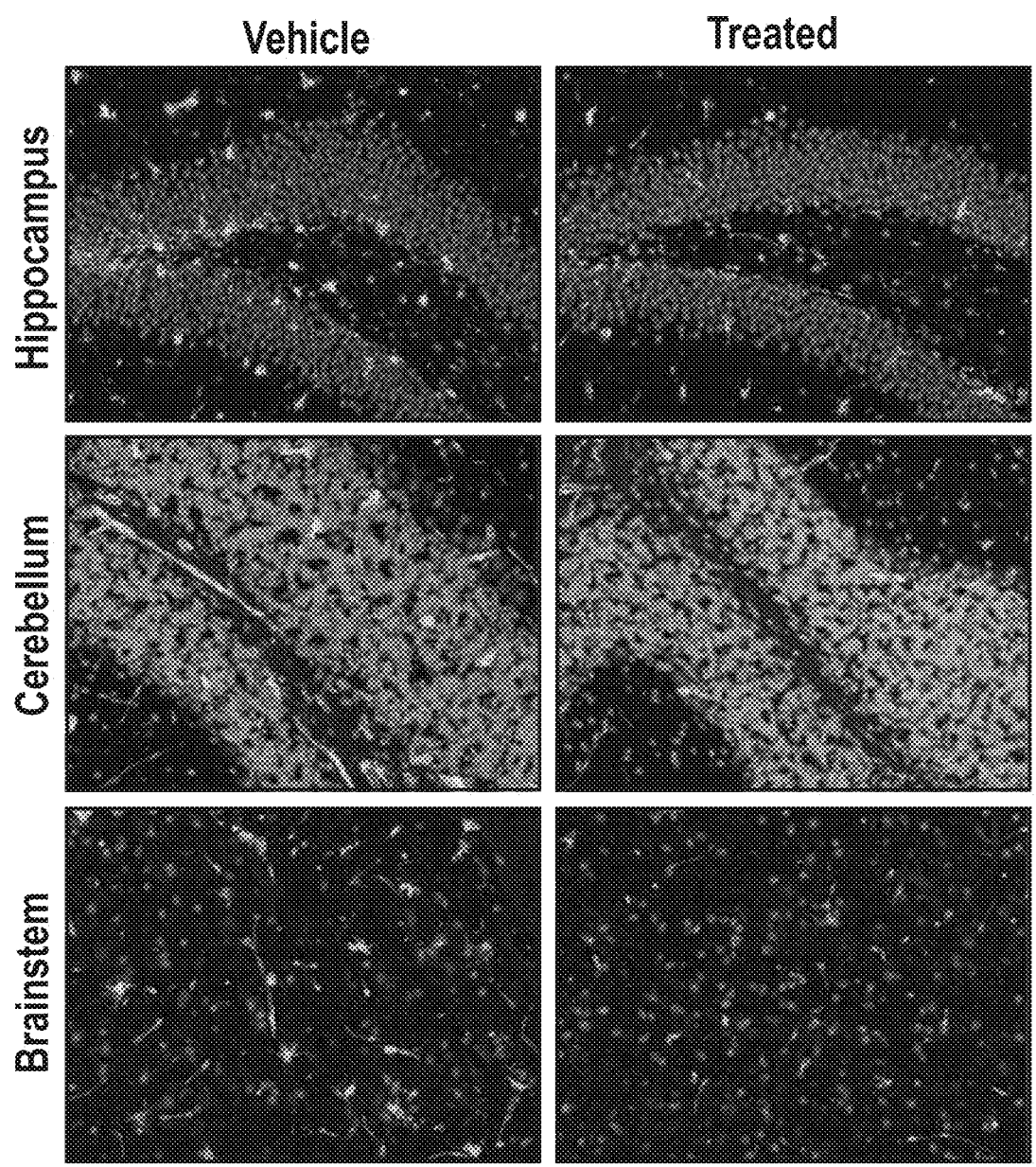

LAMP IHC in various brain regions after 6 IT Naglu injections for 3 months demonstrated that, compared with the vehicle treated group, Naglu IT administration to SFB mice resulted in a reduction of lysosomal activity in all examined regions revealed by LAMP immunostaining (FIGS. 35A and 35B). This reduction was characterized by the decrease in the number of LAMP positive cells, smaller cell size and lighter staining. A marked reduction was found in the cerebellum and brainstem, which are located in the caudate part of the brain close to the spinal cord, compared with other brain regions. A clear reduction was also found in the deep brain regions, including the white matter, hippocampus and thalamus.

Iba IHC in various brain regions after 6 IT Naglu injections for 3 months revealed activation of microglial cells (FIGS. 36A and 36B). Compared with vehicle treated group, no decease in the number of positive cells and staining intensity was observed in Naglu treated group. However, the cellular morphology of positive microglial cells changed with reduced cell size in all examined brain regions compared to large and vacuolated one in the vehicle group (inserts).

GFAP IHC in various brain regions after 6 IT Naglu injections for 3 months revealed astrocytic activation (FIGS. 37A and 37B). Compared with the vehicle treated group, GFAP positive staining was decreased in the cerebellum and brainstem, and slightly decreased in other examined regions.

With respect to cellular uptake, these data demonstrate that in the brain and spinal cord, Naglu was detected in meningial cells only after 6 time every other week Naglu IGFII IT injection for 3 month. Naglu was undetectable by IHC in any other regions of the brain and spinal cord. In the liver, Naglu positive staining was found in sinusoidal cells.

In the brain and spinal cord, after 6 every other week IT injection of Naglu-IGFII for 3 months, histopathological improvement was seen throughout the brain and spinal cord even though injected Naglu was undetectable by IHC. H&E staining demonstrated cellular vacuolation reduction in all examined brain regions. LAMP staining decreased throughout treated spinal cords and in all evaluated brain regions including the white matter, hippocampus and thalamus which are deep brain areas, with marked decrease in the cerebellum and brainstem in the Naglu-IGFII treated group.

The decreased staining pattern of GFAP staining for astrocytes was consistent with LAMP staining while not dramatically decreased as LAMP. Iba-1 staining showed reduction of the cell size of microglial cells in all examines brain regions. In the liver, H&E staining demonstrated cellular vacuolation reduction with marked reduction in LAMP staining in the Naglu treated group.

Example 7: Treatment of Sanfilippo B Patients

Direct CNS administration through, e.g., IT delivery can be used to effectively treat Sanfilippo syndrome type B (Sanfilippo B) patients. This example illustrates a multi-center dose escalation study designed to evaluate the safety of up to 3 dose levels every other week (EOW) for a total of 40 weeks of Naglu-IGFII and/or rhNaglu administered via an intrathecal drug delivery device (IDDD) to patients with Sanfilippo B Syndrome. Various exemplary intrathecal drug delivery devices suitable for human treatment are depicted in FIGS. 38-41.

Up to 20 patients will be enrolled:
Cohort 1: 5 patients (Lowest Dose)
Cohort 2: 5 patients (Intermediate Dose)
Cohort 3: 5 patients (Highest Dose)
5 patients will be randomized to no treatment.
Patients are selected for the study based on inclusion of the following criteria:
Safety of ascending doses of Naglu administered by IT injection for 40 weeks in patients with San A is determined. In addition, the clinical activity of Naglu-IGFII and/or rhNaglu on cognitive function, and single and repeated-dose pharmacokinetics in serum and concentrations in cerebrospinal fluid (CSF) are assessed.

While certain compounds, compositions and methods described herein have been described with specificity in accordance with certain embodiments, the following examples serve only to illustrate the compounds of the invention and are not intended to limit the same.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

We claim:

1. A therapeutic fusion protein comprising
   an alpha-N-acetylglucosaminidase (Naglu) domain;
   a lysosomal targeting moiety, and
   a linker between the lysosomal targeting moiety and the Naglu domain;
     wherein the lysosomal targeting moiety is a peptide that binds cation-independent mannose-6-phosphate receptor (CI-MPR) or bis-phosphorylated oligosaccharides;
   wherein the Naglu domain has alpha-N-acetylglucosaminidase activity and comprises an amino acid sequence having at least 95% sequence identity to the amino acid sequence of SEQ ID NO: 1;
   wherein the linker comprises the amino acid sequence of residues 721-777 of SEQ ID NO: 6;
   wherein once administered intrathecally, the therapeutic fusion protein is targeted to lysosomes.

2. The therapeutic fusion protein of claim 1, wherein the lysosomal targeting moiety is an insulin-like growth factor-II (IGF-II) moiety.

3. The therapeutic fusion protein of claim 1 wherein the lysosomal targeting moiety is fused via the linker to the C-terminus of the Naglu domain.

4. A pharmaceutical composition comprising the therapeutic fusion protein of claim 1 and a surfactant.

5. The pharmaceutical composition of claim 4, wherein the surfactant is present in the pharmaceutical composition at a concentration from 0.001-0.5%.

6. The pharmaceutical composition of claim 4, wherein the surfactant is present in the pharmaceutical composition at a concentration of 0.2%.

7. The pharmaceutical composition of claim 4, wherein the surfactant is a poloxamer.

8. The pharmaceutical composition of claim 7, wherein the poloxamer is poloxamer 188.

* * * * *